United States Patent
Blom et al.

(10) Patent No.: US 9,586,975 B2
(45) Date of Patent: *Mar. 7, 2017

(54) MACROCYCLIC SALT-INDUCIBLE KINASE INHIBITORS

(71) Applicant: ONCODESIGN S.A., Dijon (FR)

(72) Inventors: Petra Marcella Francoise Blom, Destelbergen (BE); Jan Marie Cyriel Jozef Hoflack, Westmalle (BE); Pascal Andre Rene Benderitter, Apollinaire (FR)

(73) Assignee: ONCODESIGN S.A., Dijon (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,798

(22) PCT Filed: Mar. 14, 2014

(86) PCT No.: PCT/EP2014/055168
§ 371 (c)(1),
(2) Date: Sep. 15, 2015

(87) PCT Pub. No.: WO2014/140313
PCT Pub. Date: Sep. 18, 2014

(65) Prior Publication Data
US 2016/0024113 A1    Jan. 28, 2016

(30) Foreign Application Priority Data

Mar. 15, 2013   (WO) ................ PCT/2013/055389

(51) Int. Cl.

| | | |
|---|---|---|
| *C07D 498/16* | (2006.01) | |
| *A61K 31/519* | (2006.01) | |
| *A61K 31/5025* | (2006.01) | |
| *C07D 487/18* | (2006.01) | |
| *C07D 487/22* | (2006.01) | |
| *C07D 498/18* | (2006.01) | |
| *C07D 498/22* | (2006.01) | |
| *C07D 513/18* | (2006.01) | |
| *C07D 515/18* | (2006.01) | |
| *C07D 491/18* | (2006.01) | |
| *C07D 513/16* | (2006.01) | |

(52) U.S. Cl.
CPC ........ *C07D 498/16* (2013.01); *A61K 31/5025* (2013.01); *A61K 31/519* (2013.01); *C07D 487/18* (2013.01); *C07D 487/22* (2013.01); *C07D 491/18* (2013.01); *C07D 498/18* (2013.01); *C07D 498/22* (2013.01); *C07D 513/16* (2013.01); *C07D 513/18* (2013.01); *C07D 515/18* (2013.01)

(58) Field of Classification Search
CPC ........................... C07D 498/16; A61K 31/519
See application file for complete search history.

(56) References Cited

U.S. PATENT DOCUMENTS

| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |
| 9,090,630 B2 * | 7/2015 | Blom ................. C07D 471/22 |
| 9,096,609 B2 * | 8/2015 | Hoflack ............. C07D 487/18 |

FOREIGN PATENT DOCUMENTS

| EP | 0 721 331 B1 | 12/2001 |
| WO | 2013/045653 A1 | 4/2013 |
| WO | 2013/046029 A1 | 4/2013 |

OTHER PUBLICATIONS

International Search Report/Written Opinion pertaining to Application No. PCT/EP2014/055168 with a filing date of Mar. 14, 2014.
Kumagai, et al., A Potent Inhibitor of SIK2, 3, 3', 7-Trihydroxy-4'-Methoxyflavon (4'-O-Methylfisetin), Promotes Melanogenesis in B16F10 Melanoma Cells, www.plosone.org, vol. 6, Issue 10, Oct. 2011, pp. 1-10, Japan.
Sasaki et al., SIK2 Is a Key Regulator for Neuronal Survival after Ischemia via TORC1-CREB, Neuron 2011, 69 : 106-119.
Horike et al., Downregulation of SIK2 expression promotes the melanogenic program in mice, Pigment Cell Melanoma Res. 2010, 23 : 809-819.
Ahmed et al., SIK2 Is a Centrosome Kinase Required for Bipolar Mitotic Spindle Formation that Provides a Potential Target for Therapy in Ovarian Cancer, Cancer Cell 2010, 18 : 109-121.
Nagel et al., Amplification at 11q23 targets protein kinase SIK2 in diffuse large B-cell lymphoma, Leukemia & Lymphoma 2010, 51(5) : 881-891.
Kumagai et al., A Potent Inhibitor of SIK2, 3, 3', 7-Trihydroxy-4'-Methoxyflavon (4'-O-Methylfisetin), Promotes Melanogenesis in B16F10 Melanoma Cells, PLoS ONE 2011, 6(10) : 1-10.
Imielinski et al., Mapping the Hallmarks of Lung Adenocarcinoma with Massively Parallel Sequencing, Cell 2012, 150 : 1107-1120.
Gallo et al., Balancing life and death in the ischemic brain : SIK and TORC weigh in, Neuron 2011, 69(1) : 3-6.
Popov et al., Relevance of the salt-inducible kinase network for the development of high blood pressure and cardiac hypertrophy, Atherosclerosis Research Unit Department of Medicine, Karolinska Institute, 2012: 1-45.
Horike et al., Adipose-specific Expression, Phosphorylation of Ser794 in Insulin Receptor Substrate-1, and Activation in Diabetic Animals of Salt-inducible Kinase-2, The Journal of Biological Chemistry 2003: 278(20) : 18440-18447.
Clark et al., Phosphorylation of CRTC3 by the salt-inducible kinases controls the interconversion of classically activated and regulatory macrophages, PNAS 2012: 109(42) : 16986-16991.

* cited by examiner

*Primary Examiner* — Golam M M Shameem
(74) *Attorney, Agent, or Firm* — Dinsmore & Shohl LLP

(57) ABSTRACT

The present invention relates to macrocyclic compounds and compositions containing said compounds acting as kinase inhibitors, in particular as inhibitors of SIK kinase, more in particular SIK1, SIK2 and/or SIK3 and/or mutants thereof, for use in the diagnosis, prevention and/or treatment of SIK-kinase associated diseases. Moreover, the present invention provides methods of using said compounds, for instance as a medicine or diagnostic agent.

9 Claims, No Drawings

MACROCYCLIC SALT-INDUCIBLE KINASE INHIBITORS

FIELD OF THE INVENTION

The present invention relates to macrocyclic compounds and compositions containing said compounds acting as kinase inhibitors, in particular as inhibitors of SIK kinase, more in particular SIK1, SIK2 and/or SIK3 and/or mutants thereof, for use in the diagnosis, prevention and/or treatment of SIK-kinase associated diseases. Moreover, the present invention provides methods of using said compounds, for instance as a medicine or diagnostic agent.

BACKGROUND OF THE INVENTION

Protein kinases constitute a large family of structurally related enzymes that are responsible for the control of a wide variety of signal transduction processes in the cell. They have been shown to be key regulators in most cellular functions including proliferation, cell metabolism, cell survival, apoptosis, DNA damage repair, cell motility . . . . Uncontrolled signalling due to defective control of protein phosphorylation has been implicated in a number of diseases, including, for example, cancer, inflammation, allergies, immune diseases, CNS disorders, angiogenesis . . . .

Amongst the families of protein kinases, one particular example is the Adenosine Monophosphate-activated Protein Kinase (AMPK) family. Salt-Inducible Kinases (SIK) are part of the AMPKs, a family of serine/threonine protein kinases involved in highly conserved cascades that control these processes, and in particular play a role in cellular energy homeostasis. Three SIK isoforms have been identified, named SIK1 (also referred as SNF1-Like Kinase (SNF1LK) or Myocardial Snf1-like Kinase (MSK)), SIK2 (SNF1LK2 or KIAA0781) and SIK3 (KIAA0999) (Trends Endocrinol. Metab. (2004) 15: 21-26).

The cloning of SIK1 that was specifically expressed in the adrenal glands of high-salt diet-fed rats led to subsequent cloning of adipose-specific SIK2 and rather ubiquitous SIK3. SIK1 has a role in the fine-tuning of steroidogenic enzyme production during the initial phase of steroidogenesis (Mol. Endocrinol. (2001) 15: 1264-1276). SIK2 is induced by insulin, hormones, and differentiation factors in multiples cell types (adipocytes, neurons, macrophages, myocytes) and promotes cellular differentiation. This is related to the inhibition of CREB (cAMP Responsive Element Binding protein)-mediated gene expression, phosphorylation of Insulin Receptor Substrate-1 (IRS1), and activation of MEF2 (Myocyte Enhancer Factor 2)-mediated gene expression (J. Biol. Chem. (2003) 278: 18440-18447; Nature (2007) 449: 366-369; Proc Natl Acad Sci USA. (2012) 109: 16986-16991). SIK2 modulates the gene transcription through the phosphorylation of substrates leading to their nuclear export, such as the transcriptional activator complexes TORC (Transducer Of Regulated CREB activity) or the transcriptional inhibitor HDAC4 (Histone Deacetylase 4). Through a similar mechanism SIK3 induced chondrocyte differentiation (Development (2012) 139: 1153-1163). In drosophila, it was shown that SIK3 was upregulated in response to insulin and SIK3 mutant flies were sensitive to starvation, suggesting that SIK3 contributes to maintain energy balance being involved in the shift from glucose to fat burning under fasting conditions (Cell (2011) 145:596-606). SIK3 is also induced in the murine liver after the consumption of a diet rich in fat, sucrose, and cholesterol (PLoS ONE (2012) 7: e37803). On the other hand, overexpression of SIK1 reduced hepatic triacylglycerol levels and lipogenic gene expression (The Journal of Biological Chemistry (2009) 284: 10446-10452). Thus, members of the SIK family are emerging as hormones and nutrients sensors, which modulate key transcriptional processes such as steroid hormone biosynthesis by the adrenal cortex, insulin signalling in adipocytes, or inflammatory cytokines in macrophages.

In context of cellular stresses associated with ATP-depletion, UV exposure, refeeding after starvation/ischemia, degradation of SIK kinases is rapidly induced after cAMP or calcium intracellular elevation. In respect to the cell types and SIK expressed proteins, these stresses activate the TORC-CREB-mediated gene expression and lead to a rapid stress cellular response. Hence, it was shown that inhibition of SIK2 after oxygen-glucose deprivation enhances neuron survival (Neuron (2011) 69:106-119) or promotes melanogenesis in melanoma cells (PLoS One (2011) 6:e26148).

Therapeutic strategies are needed to modulate the stress cellular response, such as during ischaemia and post reperfusion of tissue, in the chronic phase of cardiac remodelling, in diabetes and neurodegenerative conditions. The rapid activation or degradation of the SIK proteins, following multiple kinds of stresses, makes them interesting targets in inflammatory, cardiac or metabolic diseases and neurodegenerative disorders. SIK inhibition might also have application in cosmetology or pigmentation-related diseases to induce melanogenesis.

Besides the pivotal function in cellular energy homeostasis, the SIK proteins have also been involved in the regulation of the cell cycle. Inducible overexpression of SIK1 kinase domain in Chinese hamster ovary cells lead to cellular endoreplication (Genomics (2004) 83: 1105-1115). SIK2 plays a key role in the initiation of mitosis. It localizes at the centrosome where it phosphorylates the centrosome linker protein, C-Nap1, and its depletion blocked centrosome separation in mitosis (Cancer Cell (2010) 18: 109-121). Depletion of SIK2 also delayed G1/S transition and reduced the phosphorylation of AKT, a major protein associated with cell survival. This depletion blocked centrosome separation in mitosis, sensitizing ovarian cancers to paclitaxel in culture and in xenografts. Higher expression of SIK2 significantly correlated with poor survival in patients with high-grade serous ovarian cancers. We believe these data identify SIK2 as a plausible target for therapy in ovarian cancers. Moreover, expression of SIK3 was elevated in ovarian cancers, particularly in the serous subtype and at later stages. Overexpression of SIK3 in OVCAR3 cells promoted cell proliferation in culture and tumorigenicity following injection into nude mice (Oncogene (2011) 30: 3570-3584).

Taking into consideration the role of SIK proteins in the signalling pathways of nutrients and hormone sensors and of stress response, it was therefore an object of the present invention to provide a potent, selective, small molecule inhibitor of one or more of the SIK1, SIK2 or SIK3 which can block specifically SIK-dependent stress response or sensitize tumour cells to chemo or targeted therapies. By this means, it provides a therapeutic benefit in neurodegenerative disorders, pigmentation-related diseases and cancer as well as in cardiac, metabolic, autoimmune and inflammatory diseases characterized in increased stress responses and/or dysregulated SIK kinase activity; hereinafter referred to as 'disorders associated with SIK kinase activity'.

We have now found that the macrocyclic pyrazolopyrimidines and imidazopyridazines and pharmaceutically acceptable compositions according to this invention are useful for the diagnosis, prevention and/or treatment of several disorders associated with SIK kinase activity (i.e. SIK-kinase associated diseases).

SUMMARY OF THE INVENTION

We have surprisingly found that the macrocyclic compounds described herein act as SIK kinase inhibitors, in particular SIK1, SIK2 and/or SIK3 kinase inhibitors, and are thus very useful in the prevention and/or treatment of SIK-kinase associated diseases.

In a first objective the present invention provides a compound of Formula I or a stereoisomer, tautomer, racemic, metabolite, pro- or predrug, salt, hydrate, N-oxide form, or solvate thereof,

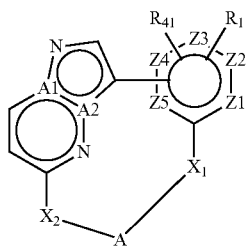

I

Wherein $A_1$ and $A_2$ are selected from C and N; wherein when $A_1$ is C, then $A_2$ is N; and wherein when $A_2$ is C, then $A_1$ is N;

$R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;

$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{29}R_{30}$, —(C=S)—$NR_{29}R_{30}$, —$C_{3-6}$cycloalkyl -$Het_2$, —$Ar_3$, —(C=O)-$Het_2$, —(C=S)-$Het_2$, —(C=O)—$Ar_3$, —(C=S)—$Ar_3$, —(C=O)—$C_{3-6}$cycloalkyl, —(C=S)—$C_{3-6}$cycloalkyl and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_2$, —$Ar_3$, and —$NR_{15}R_{16}$;

$R_4$ is independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —$Ar_8$ and -$Het_4$;

$R_5$ and $R_7$ are each independently selected from —H, —OH, -halo, —$C_{1-6}$alkyl, —O—$C_{1-6}$alkyl, —S—$C_{1-6}$alkyl, -$Het_9$, —$Ar_1$, —$C_{3-6}$cycloalkyl, —$SO_2$—$Ar_1$, —$SO_2$, —$SO_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$ alkyl, —O—(C=S)—$C_{1-6}$alkyl, —(C=O)—O—$C_{1-6}$ alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —$Ar_1$, -$Het_9$, and —$NR_{23}R_{24}$;

$R_6$ is selected from —$C_{1-6}$alkyl, —$SO_2$, —$SO_2$—$C_{1-6}$alkyl, —$SO_2$—$C_{3-6}$cycloalkyl, —(C=O), —(C=O)—$C_{1-6}$ alkyl, —(C=O)—$C_{2-6}$alkenyl, —(C=O)—O—$C_{1-6}$ alkyl, —(C=O)-$Het_6$, —(C=O)—$Ar_6$, —(C=O)—$C_{3-6}$ cycloalkyl, —(C=O)—$NR_{31}R_{32}$, —(C=O)—$NR_{31}$—(C=O)—$R_{32}$, —(C=S), —(C=S)—$C_{1-6}$alkyl, —(C=S)—$C_{2-6}$alkenyl, —(C=S)—O—$C_{1-6}$alkyl, —(C=S)-$Het_6$, —(C=S)—$Ar_6$, —(C=S)—$C_{3-6}$cycloalkyl, —(C=S)—$NR_{31}R_{32}$, —(C=S)—$NR_{31}$—(C=S)—$R_{32}$, -$Het_6$, —$Ar_6$, and —$C_{3-6}$cycloalkyl; wherein each of said —$C_{1-6}$alkyl is optionally and independently substituted with from 1 to 3 substituents selected from =O, -halo, —OH, —O—$C_{1-6}$alkyl, —S—$C_{1-6}$alkyl, —$C_{3-6}$cycloalkyl, -$Het_6$, —$Ar_6$, —$NR_{25}R_{26}$, —(C=O)—$NR_{25}R_{26}$, —$NR_{33}$(C=O)—$NR_{25}R_{26}$, —(C=S)—$NR_{25}R_{26}$, and —$NR_{33}$(C=S)—$NR_{25}R_{26}$; and
wherein each of said —$C_{3-6}$cycloalkyl is optionally and independently substituted with from 1 to 3 substituents selected from —$C_{1-6}$alkyl, =O, -halo, —OH, —O—$C_{1-6}$ alkyl, —S—$C_{1-6}$alkyl, -$Het_{12}$, —$Ar_{11}$, and —$NR_{53}R_{54}$, —(C=O)—$NR_{53}R_{54}$, —$NR_{55}$(C=O)—$NR_{53}R_{54}$, —(C=S)—$NR_{53}R_{54}$, and —$NR_{55}$(C=S)—$NR_{53}R_{54}$;

$R_8$ is selected from —$NR_{34}$—(C=O)—$R_{35}$, —$NR_{34}$—(C=S)—$R_{35}$, —$NR_{36}$—(C=O)—$NR_{34}R_{35}$, —$NR_{36}$—(C=S)—$NR_{34}R_{35}$, —$NR_{34}$—($SO_2$)—$R_{35}$, —$NR_{34}$—(C=O)—O—$R_{35}$, —$NR_{34}$—(C=S)—O—$R_{35}$, —O—(C=O)—$NR_{34}R_{35}$, and —O—(C=S)—$NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_5$ and -$Het_7$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_7$, —$Ar_5$ and —$NR_{51}R_{52}$;

$R_{51}$ and $R_{52}$ are each independently selected from —H, -halo, —OH, —$C_{1-6}$alkyl, —O—$C_{1-6}$alkyl, —S—$C_{1-6}$ alkyl, —$C_{3-6}$cycloalkyl, —$Ar_{10}$ and -$Het_{10}$;

$R_{42}$ is selected from —H, —OH, -halo, —$C_{1-6}$alkyl, —O—$C_{1-6}$alkyl, —S—$C_{1-6}$alkyl, —$NR_{46}R_{47}$, —$C_{3-6}$cycloalkyl, —$Ar_9$ and -$Het_8$;

$R_{43}$ is selected from —H —$C_{1-6}$alkyl, and —$C_{3-6}$cycloalkyl; wherein each of said —$C_{1-6}$alkyl is optionally and independently substituted with from 1 to 3 substituents selected from -halo, —OH, —O—$C_{1-6}$alkyl, —S—$C_{1-6}$ alkyl, -$Het_5$, —$C_{3-6}$cycloalkyl —$Ar_4$, and —$NR_{44}R_{45}$;

A is selected from —$(CH_2)_n$—Y—$(CH_2)_m$—, —(C=O)—, —(C=S)—, —(C=N)—$R_{49}$—, —($SO_2$)—, —$SO_2$—$NR_5$—, —(C=O)—$NR_5$—, —(C=S)—$NR_5$—, —$NR_5$—(C=O)—$NR_7$—, —$NR_5$—(C=S)—$NR_7$—, —$NR_6$—, —$NR_5$—(C=O)—O—, —$NR_5$—(C=S)—O—, and —$CHR_8$—;

$X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$alkyl-$NR_3$—, —$NR_3$—, —(C=O)—, —$NR_3$—(C=O)—$NR_{48}$—, —$NR_3$—$C_{1-6}$alkyl-, —$NR_3$—$SO_2$—, —$NR_3$—(C=O)—$C_{1-6}$alkyl-, —(C=O)—$NR_3$—$C_{1-6}$alkyl-, —O—$C_{1-6}$alkyl-O—$C_{1-6}$alkyl- and —$C_{1-6}$alkyl-$NR_3$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{37}R_{38}$;

$X_2$ is selected from —$C_{1-6}$alkyl-, —O—$C_{1-6}$alkyl-, —S—$C_{1-6}$alkyl-, —(C=O)—, —$NR_2$—(C=O)—, —$C_{1-6}$alkyl-$NR_2$—, —$NR_2$—, —(C=O)—, —$NR_2$—(C=O)—$NR_{50}$—, —$NR_2$—$C_{1-6}$alkyl-, —$NR_2$—$SO_2$—, —$NR_2$—(C=O)—$C_{1-6}$alkyl-, —(C=O)—$NR_2$—$C_{1-6}$alkyl-, —O—$C_{1-6}$alkyl-O—$C_{1-6}$alkyl- and —$C_{1-6}$alkyl-$NR_2$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{39}R_{40}$;

Y is selected from a direct bond, —$CHR_{42}$—, —O—, —S—, and —$NR_{43}$—;

$Ar_1$, $Ar_2$, $Ar_3$, $Ar_4$, $Ar_5$, $Ar_6$, $Ar_7$, $Ar_8$, $Ar_9$, $Ar_{10}$ and $Ar_{11}$ are each independently a 5- to 10-membered aromatic heterocycle optionally comprising 1 or 2 heteroatoms selected from O, N and S; each of said $Ar_1$, $Ar_2$, $Ar_3$, $Ar_4$, $Ar_5$, $Ar_6$, $Ar_7$, $Ar_8$, $Ar_9$, and $Ar_{10}$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_3$, $Het_4$, $Het_5$, $Het_6$, $Het_7$, $Het_8$, $Het_9$, $Het_{10}$, and $Het_{12}$ are each independently a 4- to 10-membered heterocycle having from 1 to 3 heteroatoms selected from O, N and S, wherein each of said $Het_1$, $Het_2$, $Het_3$, $Het_4$, $Het_5$, $Het_6$, $Het_7$, $Het_8$, $Het_9$, $Het_{10}$, and $Het_{12}$ is optionally and independently substituted with from 1 to 3 substituents selected from -halo, —OH, —$C_{1-6}$alkyl, —$OC_{1-6}$alkyl, —$SC_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and m and n are each independently 1, 2, 3, or 4;

for use in the diagnosis, prevention and/or treatment of a SIK-kinase associated disease.

In a first embodiment the present invention provides a compound of Formula I or a stereoisomer, tautomer, racemic, metabolite, pro- or predrug, salt, hydrate, N-oxide form, or solvate thereof, wherein $A_1$ is C and $A_2$ is N;

$R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;

$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{29}R_{30}$, —(C=S)—$NR_{29}R_{30}$, —$C_{3-6}$cycloalkyl -$Het_2$, —$Ar_3$, —(C=O)-$Het_2$, —(C=S)-$Het_2$, —(C=O)—$Ar_3$, —(C=S)—$Ar_3$, —(C=O)—$C_{3-6}$cycloalkyl, —(C=S)—$C_{3-6}$cycloalkyl and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_2$, —$Ar_3$, and —$NR_{15}R_{16}$;

$R_4$ is independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —$Ar_8$ and -$Het_4$;

$R_5$ and $R_7$ are each independently selected from —H, —OH, -halo, —$C_{1-6}$alkyl, —O—$C_{1-6}$alkyl, —S—$C_{1-6}$alkyl, -$Het_9$, —$Ar_1$, —$C_{3-6}$cycloalkyl, —$SO_2$—$Ar_1$, —$SO_2$, —$SO_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$alkyl, —O—(C=S)—$C_{1-6}$alkyl, —(C=O)—O—$C_{1-6}$alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —$Ar_1$, -$Het_9$, and —$NR_{23}R_{24}$;

$R_6$ is selected from —$C_{1-6}$alkyl, —$SO_2$, —$SO_2$—$C_{1-6}$alkyl, —$SO_2$—$C_{3-6}$cycloalkyl, —(C=O), —(C=O)—$C_{1-6}$alkyl, —(C=O)—$C_{2-6}$alkenyl, —(C=O)—O—$C_{1-6}$alkyl, —(C=O)-$Het_6$, —(C=O)—$Ar_6$, —(C=O)—$C_{3-6}$cycloalkyl, —(C=O)—$NR_{31}R_{32}$, —(C=O)—$NR_{31}$—(C=O)—$R_{32}$, —(C=S), —(C=S)—$C_{1-6}$alkyl, —(C=S)—$C_{2-6}$alkenyl, —(C=S)—O—$C_{1-6}$alkyl, —(C=S)-$Het_6$, —(C=S)—$Ar_6$, —(C=S)—$C_{3-6}$cycloalkyl, —(C=S)—$NR_{31}R_{32}$, —(C=S)—$NR_{31}$—(C=S)—$R_{32}$, -$Het_6$, —$Ar_6$, and —$C_{3-6}$cycloalkyl; wherein each of said —$C_{1-6}$alkyl is optionally and independently substituted with from 1 to 3 substituents selected from =O, -halo, —OH, —O—$C_{1-6}$alkyl, —S—$C_{1-6}$alkyl, —$C_{3-6}$cycloalkyl, -$Het_6$, —$Ar_6$, —$NR_{25}R_{26}$, —(C=O)—$NR_{25}R_{26}$, —$NR_{33}$(C=O)—$NR_{25}R_{26}$, —(C=S)—$NR_{25}R_{26}$, and —$NR_{33}$(C=S)—$NR_{25}R_{26}$; and wherein each of said —$C_{3-6}$cycloalkyl is optionally and independently substituted with from 1 to 3 substituents selected from —$C_{1-6}$alkyl, =O, -halo, —OH, —O—$C_{1-6}$alkyl, —S—$C_{1-6}$alkyl, -$Het_{12}$, —$Ar_{11}$, and —$NR_{53}R_{54}$, —(C=O)—$NR_{53}R_{54}$, —$NR_{55}$(C=O)—$NR_{53}R_{54}$, —(C=S)—$NR_{53}R_{54}$, and —$NR_{55}$(C=S)—$NR_{53}R_{54}$;

$R_8$ is selected from —$NR_{34}$—(C=O)—$R_{35}$, —$NR_{34}$—(C=S)—$R_{35}$, —$NR_{36}$—(C=O)—$NR_{34}R_{35}$, —$NR_{36}$—(C=S)—$NR_{34}R_{35}$, —$NR_{34}$—($SO_2$)—$R_{35}$, —$NR_{34}$—(C=O)—O—$R_{35}$, —$NR_{34}$—(C=S)—O—$R_{35}$, —O—(C=O)—$NR_{34}R_{35}$, and —O—(C=S)—$NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_5$ and -$Het_7$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_7$, —$Ar_5$ and —$NR_{51}R_{52}$;

$R_{51}$ and $R_{52}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_{10}$ and -$Het_{10}$;

$R_{42}$ is selected from —H, —OH, -halo, —$C_{1-6}$alkyl, —O—$C_{1-6}$alkyl, —S—$C_{1-6}$alkyl, —$NR_{46}R_{47}$, —$C_{3-6}$cycloalkyl, —$Ar_9$ and -$Het_8$;

$R_{43}$ is selected from —H —$C_{1-6}$alkyl, and —$C_{3-6}$cycloalkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_5$, —$C_{3-6}$cycloalkyl —$Ar_4$, and —$NR_{44}R_{45}$;

A is selected from —$(CH_2)_n$—Y—$(CH_2)_m$—, —(C=O)—, —(C=S)—, —(C=N)—$R_{49}$—, —$(SO_2)$—, —$SO_2$—$NR_5$—, —(C=O)—$NR_5$—, —(C=S)—$NR_5$—, —$NR_5$—(C=O)—$NR_7$—, —$NR_5$—(C=S)—$NR_7$—, —$NR_6$—, —$NR_5$—(C=O)—O—, —$NR_5$—(C=S)—O—, and —$CHR_8$—;

$X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$alkyl-$NR_3$—, —$NR_3$—, —(C=O)—, —$NR_3$—(C=O)—$NR_{48}$—, —$NR_3$—$C_{1-6}$alkyl-, —$NR_3$—$SO_2$—, —$NR_3$—(C=O)—$C_{1-6}$alkyl-, —(C=O)—$NR_3$—$C_{1-6}$alkyl-, —O—$C_{1-6}$alkyl-O—$C_{1-6}$alkyl- and —$C_{1-6}$alkyl-$NR_3$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{37}R_{38}$;

$X_2$ is selected from —$C_{1-6}$alkyl-, —O—$C_{1-6}$alkyl-, —S—$C_{1-6}$alkyl-, —(C=O)—, —$NR_2$—(C=O)—, —$C_{1-6}$alkyl-$NR_2$—, —$NR_2$—, —(C=O)—, —$NR_2$—(C=O)—$NR_{50}$—, —$NR_2$—$C_{1-6}$alkyl-, —$NR_2$—$SO_2$—, —$NR_2$—(C=O)—$C_{1-6}$alkyl-, —(C=O)—$NR_2$—$C_{1-6}$alkyl-, —O—$C_{1-6}$alkyl-O—$C_{1-6}$alkyl- and —$C_{1-6}$alkyl-$NR_2$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{39}R_{40}$;

Y is selected from a direct bond, —$CHR_{42}$—, —O—, —S—, and —$NR_{43}$—;

$Ar_1, Ar_2, Ar_3, Ar_4, Ar_5, Ar_6, Ar_7, Ar_8, Ar_9, Ar_{10}$ and $Ar_{11}$ are each independently a 5- to 10-membered aromatic heterocycle optionally comprising 1 or 2 heteroatoms selected from O, N and S; each of said $Ar_1, Ar_2, Ar_3, Ar_4, Ar_5, Ar_6, Ar_7, Ar_8, Ar_9$, and $Ar_{10}$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1, Het_2, Het_3, Het_4, Het_5, Het_6, Het_7, Het_8, Het_9, Het_{10}$, and $Het_{12}$ are each independently a 4- to 10-membered heterocycle having from 1 to 3 heteroatoms selected from O, N and S, wherein each of said $Het_1, Het_2, Het_3, Het_4, Het_5, Het_6, Het_7, Het_8, Het_9, Het_{10}$, and $Het_{12}$ is optionally and independently substituted with from 1 to 3 substituents selected from -halo, —OH, —$C_{1-6}$alkyl, —O$C_{1-6}$alkyl, —S$C_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Z_1, Z_2, Z_3, Z_4$ and $Z_5$ are each independently selected from C and N; and m and n are each independently 1, 2, 3, or 4;

for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, wherein $A_1$ is N and $A_2$ is C $R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;

$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{29}R_{30}$, —(C=S)—$NR_{29}R_{30}$, —$C_{3-6}$cycloalkyl -$Het_2$, —$Ar_3$, —(C=O)-$Het_2$, —(C=S)-$Het_2$, —(C=O)—$Ar_3$, —(C=S)—$Ar_3$, —(C=O)—$C_{3-6}$cycloalkyl, —(C=S)—$C_{3-6}$cycloalkyl and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_2$, —$Ar_3$, and —$NR_{15}R_{16}$;

$R_4$ is independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —$Ar_8$ and -$Het_4$;

$R_5$ and $R_7$ are each independently selected from —H, —OH, -halo, —$C_{1-6}$alkyl, —O—$C_{1-6}$alkyl, —S—$C_{1-6}$alkyl, -$Het_9$, —$Ar_1$, —$C_{3-6}$cycloalkyl, —$SO_2$—$Ar_1$, —$SO_2$, —$SO_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$alkyl, —O—(C=S)—$C_{1-6}$alkyl, —(C=O)—O—$C_{1-6}$alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —$Ar_1$, -$Het_9$, and —$NR_{23}R_{24}$;

$R_6$ is selected from —$C_{1-6}$alkyl, —$SO_2$, —$SO_2$—$C_{1-6}$alkyl, —$SO_2$—$C_{3-6}$cycloalkyl, —(C=O), —(C=O)—$C_{1-6}$alkyl, —(C=O)—$C_{2-6}$alkenyl, —(C=O)—O—$C_{1-6}$alkyl, —(C=O)-$Het_6$, —(C=O)—$Ar_6$, —(C=O)—$C_{3-6}$cycloalkyl, —(C=O)—$NR_{31}R_{32}$, —(C=O)—$NR_{31}$—(C=O)—$R_{32}$, —(C=S), —(C=S)—$C_{1-6}$alkyl, —(C=S)—$C_{2-6}$alkenyl, —(C=S)—O—$C_{1-6}$alkyl, —(C=S)-$Het_6$, —(C=S)—$Ar_6$, —(C=S)—$C_{3-6}$cycloalkyl, —(C=S)—NR$_{31}$R$_{32}$, —(C=S)—NR$_{31}$—(C=S)—R$_{32}$, -Het$_6$, —Ar$_6$, and —C$_{3-6}$cycloalkyl;
wherein each of said —C$_{1-6}$alkyl is optionally and independently substituted with from 1 to 3 substituents selected from =O, -halo, —OH, —O—C$_{1-6}$alkyl, —S—C$_{1-6}$alkyl, —C$_{3-6}$cycloalkyl, -Het$_6$, —Ar$_6$, —NR$_{25}$R$_{26}$, —(C=O)—NR$_{25}$R$_{26}$, —NR$_{33}$(C=O)—NR$_{25}$R$_{26}$, —(C=S)—NR$_{25}$R$_{26}$, and —NR$_{33}$(C=S)—NR$_{25}$R$_{26}$; and
wherein each of said —C$_{3-6}$cycloalkyl is optionally and independently substituted with from 1 to 3 substituents selected from —C$_{1-6}$alkyl, =O, -halo, —OH, —O—C$_{1-6}$alkyl, —S—C$_{1-6}$alkyl, -Het$_{12}$, —Ar$_{11}$, and —NR$_{53}$R$_{54}$, —(C=O)—NR$_{53}$R$_{54}$, —NR$_{55}$(C=O)—NR$_{53}$R$_{54}$, —(C=S)—NR$_{53}$R$_{54}$, and —NR$_{55}$(C=S)—NR$_{53}$R$_{54}$;

R$_8$ is selected from —NR$_{34}$—(C=O)—R$_{35}$, —NR$_{34}$—(C=S)—R$_{35}$, —NR$_{36}$—(C=O)—NR$_{34}$R$_{35}$, —NR$_{36}$—(C=S)—NR$_{34}$R$_{35}$, —NR$_{34}$—(SO$_2$)—R$_{35}$, —NR$_{34}$—(C=O)—O—R$_{35}$, —NR$_{34}$—(C=S)—O—R$_{35}$, —O—(C=O)—NR$_{34}$R$_{35}$, and —O—(C=S)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$, R$_{40}$, R$_{44}$, R$_{45}$, R$_{46}$, R$_{47}$, R$_{48}$, R$_{49}$, R$_{50}$, R$_{53}$, R$_{54}$ and R$_{55}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_5$ and -Het$_7$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_7$, —Ar$_5$ and —NR$_{51}$R$_{52}$;

R$_{51}$ and R$_{52}$ are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_{10}$ and -Het$_{10}$;

R$_{42}$ is selected from —H, —OH, -halo, —C$_{1-6}$alkyl, —O—C$_{1-6}$alkyl, —S—C$_{1-6}$alkyl, —NR$_{46}$R$_{47}$, —C$_{3-6}$cycloalkyl, —Ar$_9$ and -Het$_8$;

R$_{43}$ is selected from —H —C$_{1-6}$alkyl, and —C$_{3-6}$cycloalkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, -Het$_5$, —C$_{3-6}$cycloalkyl —Ar$_4$, and —NR$_{44}$R$_{45}$;

A is selected from —(CH$_2$)$_n$—Y—(CH$_2$)$_m$—, —(C=O)—, —(C=S)—, —(C=N)—R$_{49}$—, —(SO$_2$)—, —SO$_2$—NR$_5$—, —(C=O)—NR$_5$—, —(C=S)—NR$_5$—, —NR$_5$—(C=O)—NR$_7$—, —NR$_5$—(C=S)—NR$_7$—, —NR$_6$—, —NR$_5$—(C=O)—O—, —NR$_5$—(C=S)—O—, and —CHR$_8$—;

X$_1$ is selected from —C$_{1-6}$alkyl-, —O—C$_{1-6}$alkyl-, —S—C$_{1-6}$alkyl-, —(C=O)—, —NR$_3$—(C=O)—, —C$_{1-6}$alkyl-NR$_3$—, —NR$_3$—, —(C=O)—, —NR$_3$—(C=O)—NR$_{48}$—, —NR$_3$—C$_{1-6}$alkyl-, —NR$_3$—SO$_2$—, —NR$_3$—(C=O)—C$_{1-6}$alkyl-, —(C=O)—NR$_3$—C$_{1-6}$alkyl-, —O—C$_{1-6}$alkyl-O—C$_{1-6}$alkyl- and —C$_{1-6}$alkyl-NR$_3$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{37}$R$_{38}$;

X$_2$ is selected from —C$_{1-6}$alkyl-, —O—C$_{1-6}$alkyl-, —S—C$_{1-6}$alkyl-, —(C=O)—, —NR$_2$—(C=O)—, —C$_{1-6}$alkyl-NR$_2$—, —NR$_2$—, —(C=O)—, —NR$_2$—(C=O)—NR$_{50}$—, —NR$_2$—C$_{1-6}$alkyl-, —NR$_2$—SO$_2$—, —NR$_2$—(C=O)—C$_{1-6}$alkyl-, —(C=O)—NR$_2$—C$_{1-6}$alkyl-, —O—C$_{1-6}$alkyl-O—C$_{1-6}$alkyl- and —C$_{1-6}$alkyl-NR$_2$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{39}$R$_{40}$;

Y is selected from a direct bond, —CHR$_{42}$—, —O—, —S—, and —NR$_{43}$—;

Ar$_1$, Ar$_2$, Ar$_3$, Ar$_4$, Ar$_5$, Ar$_6$, Ar$_7$, Ar$_8$, Ar$_9$, Ar$_{10}$ and Ar$_{11}$ are each independently a 5- to 10-membered aromatic heterocycle optionally comprising 1 or 2 heteroatoms selected from O, N and S; each of said Ar$_1$, Ar$_2$, Ar$_3$, Ar$_4$, Ar$_5$, Ar$_6$, Ar$_7$, Ar$_8$, Ar$_9$, and Ar$_{10}$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, —OH, —C$_{1-6}$alkyl, —OC$_{1-6}$alkyl, —SC$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N; and m and n are each independently 1, 2, 3, or 4;

for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, wherein A$_1$ and A$_2$ are selected from C and N; wherein when A$_1$ is C, then A$_2$ is N; and wherein when A$_2$ is C, then A$_1$ is N;

R$_1$ and R$_{41}$ are each independently selected from —H, -halo, —OH, —C$_{1-6}$alkyl, and —(C=O)—R$_4$; wherein each of said —C$_{1-6}$alkyl is optionally and independently substituted with from 1 to 3 substituents selected from -halo, —OH, and —O—C$_{1-6}$alkyl;

R$_2$ is selected from —H and —(C=O)—NR$_{27}$R$_{28}$;

R$_3$ is —H;

R$_4$ is —NR$_{17}$R$_{18}$;

R$_6$ is selected from —C$_{1-6}$alkyl, —(C=O)—C$_{3-6}$cycloalkyl, -Het$_6$, and —C$_{3-6}$cycloalkyl;
wherein each of said —C$_{1-6}$alkyl is optionally and independently substituted with from 1 to 3 substituents selected from —OH, —C$_{3-6}$cycloalkyl, -Het$_6$, —NR$_{25}$R$_{26}$, and —(C=O)—NR$_{25}$R$_{26}$;
and wherein each of said —C$_{3-6}$cycloalkyl is optionally and independently substituted with from 1 to 3 substituents selected from =O R$_{17}$, R$_{18}$, R$_{25}$, R$_{26}$, R$_{27}$, and R$_{28}$ are each independently selected from —H, and —C$_{1-6}$alkyl; wherein each of said —C$_{1-6}$alkyl is optionally and independently substituted with from 1 to 3 substituents selected from -Het$_7$, and —NR$_{51}$R$_{52}$;

R$_{51}$ and R$_{52}$ are each —C$_{1-6}$alkyl;

R$_{43}$ is —H;

A is selected from —(CH$_2$)$_n$—Y—(CH$_2$)$_m$—, and —NR$_6$—;

X$_1$ is selected from —O—C$_{1-6}$alkyl-, —S—C$_{1-6}$alkyl- and —C$_{1-6}$alkyl-NR$_3$—;

X$_2$ is selected from —O—C$_{1-6}$alkyl-, —S—C$_{1-6}$alkyl-, and —C$_{1-6}$alkyl-NR$_2$;

Y is —NR$_{43}$—;
Het$_6$ and Het$_7$ are each independently selected from a 5- to 10-membered heterocycle having from 1 to 3 heteroatoms selected from O, N and S;
Z$_1$, Z$_2$, Z$_3$, Z$_4$ and Z$_5$ are each independently selected from C and N; and
m and n are each independently 1, 2, 3, or 4;
for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, wherein
A$_1$ is C and A$_2$ is N;
R$_1$ and R$_{41}$ are each independently selected from —H, -halo, —OH, —C$_{1-6}$alkyl, and —(C=O)—R$_4$; wherein each of said —C$_{1-6}$alkyl is optionally and independently substituted with from 1 to 3 substituents selected from -halo, —OH, and —O—C$_{1-6}$alkyl;
R$_2$ is selected from —H and —(C=O)—NR$_{27}$R$_{28}$;
R$_3$ is —H;
R$_4$ is —NR$_{17}$R$_{18}$;
R$_6$ is selected from —C$_{1-6}$alkyl, —(C=O)—C$_{3-6}$cycloalkyl, -Het$_6$, and —C$_{3-6}$cycloalkyl;
wherein each of said —C$_{1-6}$alkyl is optionally and independently substituted with from 1 to 3 substituents selected from —OH, —C$_{3-6}$cycloalkyl, -Het$_6$, —NR$_{25}$R$_{26}$, and —(C=O)—NR$_{25}$R$_{26}$;
and wherein each of said —C$_{3-6}$cycloalkyl is optionally and independently substituted with from 1 to 3 substituents selected from =O
R$_{17}$, R$_{18}$, R$_{25}$, R$_{26}$, R$_{27}$, and R$_{28}$ are each independently selected from —H, and —C$_{1-6}$alkyl; wherein each of said —C$_{1-6}$alkyl is optionally and independently substituted with from 1 to 3 substituents selected from -Het$_7$, and —NR$_{51}$R$_{52}$;
R$_{51}$ and R$_{52}$ are each —C$_{1-6}$alkyl;
R$_{43}$ is —H;
A is selected from —(CH$_2$)$_n$—Y—(CH$_2$)$_m$—, and —NR$_6$—;
X$_1$ is selected from —O—C$_{1-6}$alkyl-, —S—C$_{1-6}$alkyl- and —C$_{1-6}$alkyl-NR$_3$—;
X$_2$ is selected from —O—C$_{1-6}$alkyl-, —S—C$_{1-6}$alkyl-, and —C$_{1-6}$alkyl-NR$_2$;
Y is —NR$_{43}$—;
Het$_6$ and Het$_7$ are each independently selected from a 5- to 10-membered heterocycle having from 1 to 3 heteroatoms selected from O, N and S;
Z$_1$, Z$_2$, Z$_3$, Z$_4$ and Z$_5$ are each independently selected from C and N; and
m and n are each independently 1, 2, 3, or 4;
for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, wherein
A$_1$ is N and A$_2$ is C;
R$_1$ and R$_{41}$ are each independently selected from —H, -halo, —OH, —C$_{1-6}$alkyl, and —(C=O)—R$_4$; wherein each of said —C$_{1-6}$alkyl is optionally and independently substituted with from 1 to 3 substituents selected from -halo, —OH, and —O—C$_{1-6}$alkyl;
R$_2$ is selected from —H and —(C=O)—NR$_{27}$R$_{28}$;
R$_3$ is —H;
R$_4$ is —NR$_{17}$R$_{18}$;
R$_6$ is selected from —C$_{1-6}$alkyl, —(C=O)—C$_{3-6}$cycloalkyl, -Het$_6$, and —C$_{3-6}$cycloalkyl;
wherein each of said —C$_{1-6}$alkyl is optionally and independently substituted with from 1 to 3 substituents selected from —OH, —C$_{3-6}$cycloalkyl, -Het$_6$, —NR$_{25}$R$_{26}$, and —(C=O)—NR$_{25}$R$_{26}$;
and wherein each of said —C$_{3-6}$cycloalkyl is optionally and independently substituted with from 1 to 3 substituents selected from =O
R$_{17}$, R$_{18}$, R$_{25}$, R$_{26}$, R$_{27}$, and R$_{28}$ are each independently selected from —H, and —C$_{1-6}$alkyl; wherein each of said —C$_{1-6}$alkyl is optionally and independently substituted with from 1 to 3 substituents selected from -Het$_7$, and —NR$_{51}$R$_{52}$;
R$_{51}$ and R$_{52}$ are each —C$_{1-6}$alkyl;
R$_{43}$ is —H;
A is selected from —(CH$_2$)$_n$—Y—(CH$_2$)$_m$—, and —NR$_6$—;
X$_1$ is selected from —O—C$_{1-6}$alkyl-, —S—C$_{1-6}$alkyl- and —C$_{1-6}$alkyl-NR$_3$—;
X$_2$ is selected from —O—C$_{1-6}$alkyl-, —S—C$_{1-6}$alkyl-, and —C$_{1-6}$alkyl-NR$_2$;
Y is —NR$_{43}$—;
Het$_6$ and Het$_7$ are each independently selected from a 5- to 10-membered heterocycle having from 1 to 3 heteroatoms selected from O, N and S;
Z$_1$, Z$_2$, Z$_3$, Z$_4$ and Z$_5$ are each independently selected from C and N; and
m and n are each independently 1, 2, 3, or 4;
for use in the diagnosis, prevention and/or treatment of a SIK-kinase associated disease.

In a further aspect, the present invention provides a compound according to the present invention for use in the diagnosis, prevention and/or treatment of a SIK-kinase associated disease; wherein the pyrazolopyrimidine or the imidazopyridazine moiety is linked to the aryl or heteroaryl moiety at position Z$_4$ or Z$_5$, in accordance with the numbering as provided in Formula I.

In yet a further aspect, the present invention provides a compound according to the present invention for use in the diagnosis, prevention and/or treatment of a SIK-kinase associated disease; wherein R$_1$ is linked to the aryl or heteroaryl moiety at position Z$_1$, Z$_2$ or Z$_3$, in accordance with the numbering as provided in Formula I.

In a particular embodiment, the present invention provides a compound selected from the list comprising:

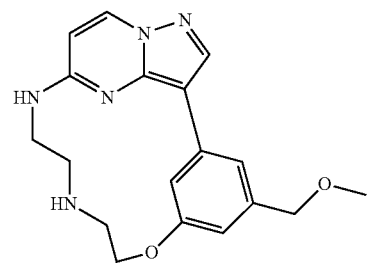

-continued
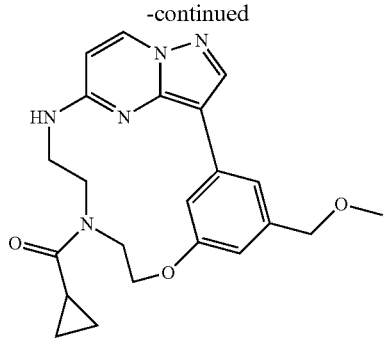
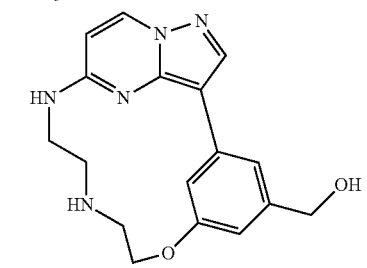
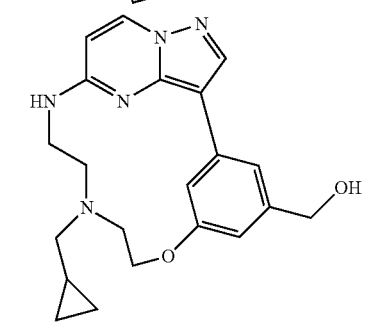
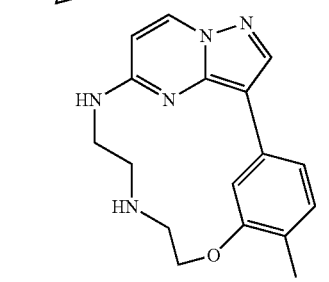
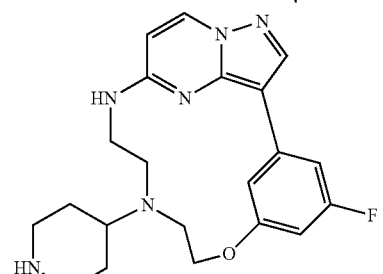
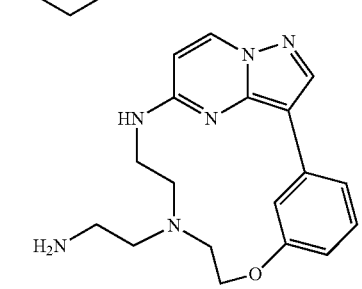
-continued
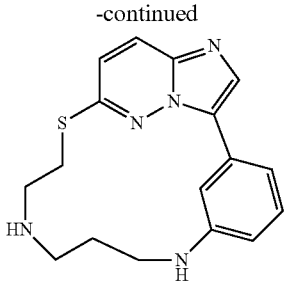
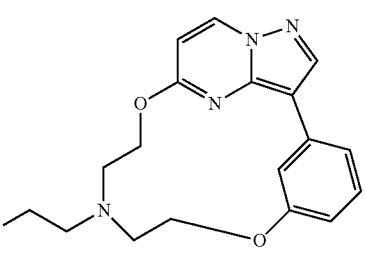
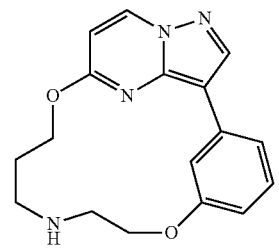
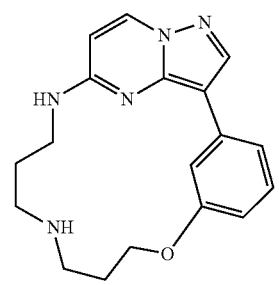
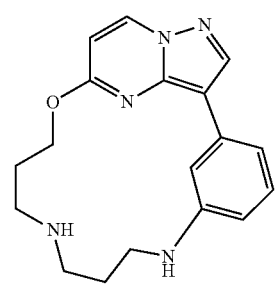
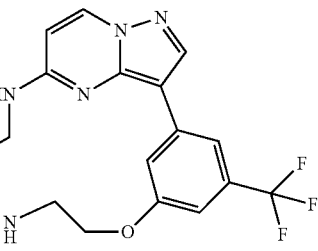

-continued

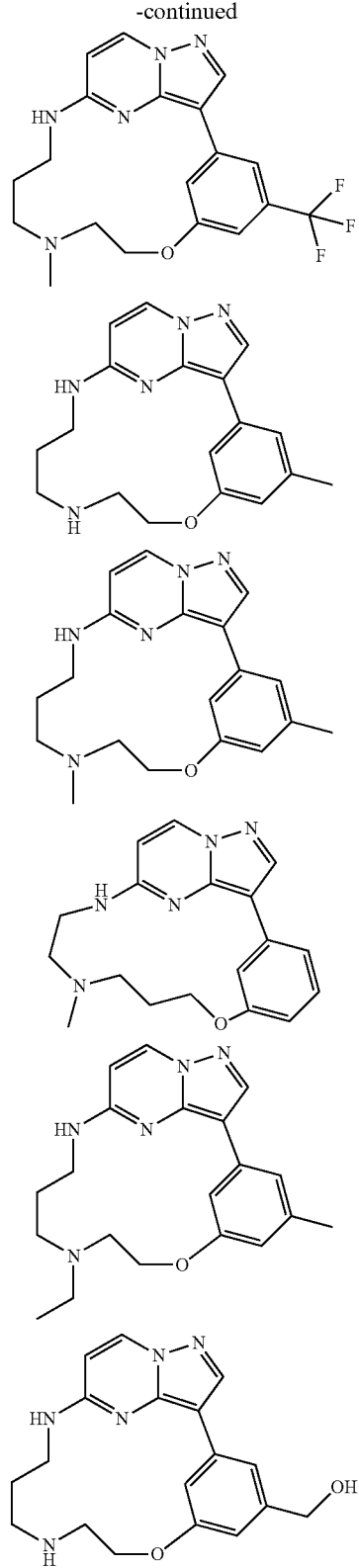

In a particular embodiment, the SIK-kinase associated disease is selected from the list comprising neurodegenerative disorders, pigmentation-related diseases and cancer, as well as cardiac, metabolic, autoimmune and inflammatory diseases.

The present invention further provides a pharmaceutical composition for use in the prevention and/or treatment of a SIK-kinase associated disease comprising a compound according to this invention.

Furthermore, the present invention provides the use of a compound or composition according to this invention, suitable for inhibiting the activity of a kinase; in particular a SIK kinase; or for the diagnosis, prevention and/or treatment of a SIK-kinase associated disease.

Finally, the present invention provides a method for prevention and/or treatment of a SIK-kinase associated disease; said method comprising administering to a subject in need thereof a compound or a composition according to the present invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides a compound of Formula I or a stereoisomer, tautomer, racemic, metabolite, pro- or pre-drug, salt, hydrate, N-oxide form, or solvate thereof,

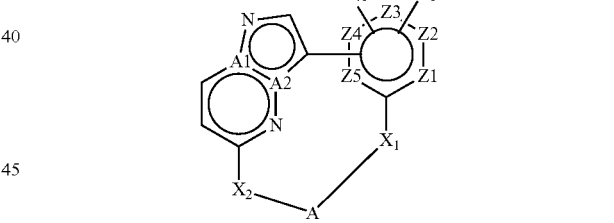

I

Wherein $R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, and —NR$_{13}$R$_{14}$;

R$_3$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=S)—C$_{1-6}$alkyl, —(C=O)—O—C$_{1-6}$alkyl, —(C=S)—O—C$_{1-6}$alkyl, —(C=O)—NR$_{29}$R$_{30}$, —(C=S)—NR$_{29}$R$_{30}$, —C$_{3-6}$cycloalkyl -Het$_2$, —Ar$_3$, —(C=O)-Het$_2$, —(C=S)-Het$_2$, —(C=O)—Ar$_3$, —(C=S)—Ar$_3$, —(C=O)—C$_{3-6}$cycloalkyl, —(C=S)—C$_{3-6}$cycloalkyl and —SO$_2$—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_2$, —Ar$_3$, and —NR$_{15}$R$_{16}$;

R$_4$ is independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —Ar$_8$ and -Het$_4$;

R$_5$ and R$_7$ are each independently selected from —H, —OH, -halo, —C$_{1-6}$alkyl, —O—C$_{1-6}$alkyl, —S—C$_{1-6}$alkyl, -Het$_9$, —Ar$_1$, —C$_{3-6}$cycloalkyl, —SO$_2$—Ar$_1$, —SO$_2$—SO$_2$—C$_{1-6}$alkyl, —(C=O), —(C=O)—C$_{1-6}$alkyl, —(C=S), —(C=S)—C$_{1-6}$alkyl, —O—(C=O)—C$_{1-6}$alkyl, —O—(C=S)—C$_{1-6}$alkyl, —(C=O)—O—C$_{1-6}$alkyl, and —(C=S)—O—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, —Ar$_1$, -Het$_9$, and —NR$_{23}$R$_{24}$;

R$_6$ is selected from —C$_{1-6}$alkyl, —SO$_2$, —SO$_2$—C$_{1-6}$alkyl, —SO$_2$—C$_{3-6}$cycloalkyl, —(C=O), —(C=O)—C$_{1-6}$alkyl, —(C=O)—C$_{2-6}$alkenyl, —(C=O)—O—C$_{1-6}$alkyl, —(C=O)-Het$_6$, —(C=O)—Ar$_6$, —(C=O)—C$_{3-6}$cycloalkyl, —(C=O)—NR$_{31}$R$_{32}$, —(C=O)—NR$_{31}$—(C=O)—R$_{32}$, —(C=S), —(C=S)—C$_{1-6}$alkyl, —(C=S)—C$_{2-6}$alkenyl, —(C=S)—O—C$_{1-6}$alkyl, —(C=S)-Het$_6$, —(C=S)—Ar$_6$, —(C=S)—C$_{3-6}$cycloalkyl, —(C=S)—NR$_{31}$R$_{32}$, —(C=S)—NR$_{31}$—(C=S)—R$_{32}$, -Het$_6$, —Ar$_6$, and —C$_{3-6}$cycloalkyl; wherein each of said —C$_{1-6}$alkyl is optionally and independently substituted with from 1 to 3 substituents selected from =O, -halo, —OH, —O—C$_{1-6}$alkyl, —S—C$_{1-6}$alkyl, —C$_{3-6}$cycloalkyl, -Het$_6$, —Ar$_6$, —NR$_{25}$R$_{26}$, —(C=O)—NR$_{25}$R$_{26}$, —NR$_{33}$(C=O)—NR$_{25}$R$_{26}$, —(C=S)—NR$_{25}$R$_{26}$, and —NR$_{33}$(C=S)—NR$_{25}$R$_{26}$; and
wherein each of said —C$_{3-6}$cycloalkyl is optionally and independently substituted with from 1 to 3 substituents selected from —C$_{1-6}$alkyl, =O, -halo, —OH, —O—C$_{1-6}$alkyl, —S—C$_{1-6}$alkyl, -Het$_{12}$, —Ar$_{11}$, and —NR$_{53}$R$_{54}$, —(C=O)—NR$_{53}$R$_{54}$, —NR$_{55}$(C=O)—NR$_{53}$R$_{54}$, —(C=S)—NR$_{53}$R$_{54}$, and —NR$_{55}$(C=S)—NR$_{53}$R$_{54}$;

R$_8$ is selected from —NR$_{34}$—(C=O)—R$_{35}$, —NR$_{34}$—(C=S)—R$_{35}$, —NR$_{36}$—(C=O)—NR$_{34}$R$_{35}$, —NR$_{36}$—(C=S)—NR$_{34}$R$_{35}$, —NR$_{34}$—(SO$_2$)—R$_{35}$, —NR$_{34}$—(C=O)—O—R$_{35}$, —NR$_{34}$—(C=S)—O—R$_{35}$, —O—(C=O)—NR$_{34}$R$_{35}$, and —O—(C=S)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$, R$_{40}$, R$_{44}$, R$_{45}$, R$_{46}$, R$_{47}$, R$_{48}$, R$_{49}$, R$_{50}$, R$_{53}$, R$_{54}$ and R$_{55}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_5$ and -Het$_7$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_7$, —Ar$_5$ and —NR$_{51}$R$_{52}$;

R$_{51}$ and R$_{52}$ are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_{10}$ and -Het$_{10}$;

R$_{42}$ is selected from —H, —OH, -halo, —C$_{1-6}$alkyl, —O—C$_{1-6}$alkyl, —S—C$_{1-6}$alkyl, —NR$_{46}$R$_{47}$, —C$_{3-6}$cycloalkyl, —Ar$_9$ and -Het$_8$;

R$_{43}$ is selected from —H —C$_{1-6}$alkyl, and —C$_{3-6}$cycloalkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, -Het$_5$, —C$_{3-6}$cycloalkyl —Ar$_4$, and —NR$_{44}$R$_{45}$;

A is selected from —(CH$_2$)$_n$—Y—(CH$_2$)$_m$—, —(C=O)—, —(C=S)—, —(C=N)—R$_{49}$—, —(SO$_2$)—, —SO$_2$—NR$_5$—, —(C=O)—NR$_5$—, —(C=S)—NR$_5$—, —NR$_5$—(C=O)—NR$_7$—, —NR$_5$—(C=S)—NR$_7$—, —NR$_6$—, —NR$_5$—(C=O)—O—, —NR$_5$—(C=S)—O—, and —CHR$_8$—;

X$_1$ is selected from —C$_{1-6}$alkyl-, —O—C$_{1-6}$alkyl-, —S—C$_{1-6}$alkyl-, —(C=O)—, —NR$_3$—(C=O)—, —C$_{1-6}$alkyl-NR$_3$—, —NR$_3$—, —(C=O)—, —NR$_3$—(C=O)—NR$_{48}$—, —NR$_3$—C$_{1-6}$alkyl-, —NR$_3$—SO$_2$—, —NR$_3$—(C=O)—C$_{1-6}$alkyl-, —(C=O)—NR$_3$—C$_{1-6}$alkyl-, —O—C$_{1-6}$alkyl-O—C$_{1-6}$alkyl- and —C$_{1-6}$alkyl-NR$_3$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{37}$R$_{38}$;

X$_2$ is selected from —C$_{1-6}$alkyl-, —O—C$_{1-6}$alkyl-, —S—C$_{1-6}$alkyl-, —(C=O)—, —NR$_2$—(C=O)—, —C$_{1-6}$alkyl-NR$_2$—, —NR$_2$—, —(C=O)—, —NR$_2$—(C=O)—NR$_{50}$—, —NR$_2$—C$_{1-6}$alkyl-, —NR$_2$—SO$_2$—, —NR$_2$—(C=O)—C$_{1-6}$alkyl-, —(C=O)—NR$_2$—C$_{1-6}$alkyl-, —O—C$_{1-6}$alkyl-O—C$_{1-6}$alkyl- and —C$_{1-6}$alkyl-NR$_2$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{39}$R$_{40}$;

Y is selected from a direct bond, —CHR$_{42}$—, —O—, —S—, and —NR$_{43}$—;

Ar$_1$, Ar$_2$, Ar$_3$, Ar$_4$, Ar$_5$, Ar$_6$, Ar$_7$, Ar$_8$, Ar$_9$, Ar$_{10}$ and Ar$_{11}$ are each independently a 5- to 10-membered aromatic heterocycle optionally comprising 1 or 2 heteroatoms selected from O, N and S; each of said Ar$_1$, Ar$_2$, Ar$_3$, Ar$_4$, Ar$_5$, Ar$_6$, Ar$_7$, Ar$_8$, Ar$_9$, and Ar$_{10}$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, —OH, —C$_{1-6}$alkyl, —OC$_{1-6}$alkyl, —SC$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N; and m and n are each independently 1, 2, 3, or 4;

for use in the diagnosis, prevention and/or treatment of a SIK-kinase associated disease.

Unless indicated otherwise, all of the above radicals can be read both ways. For example, when A is —(C=O)—NR$_5$—, the —(C=O)— may be attached to X$_2$ and —NR$_5$— attached to X$_1$. Alternatively, the —(C=O)— may be attached to X$_1$ and —NR$_5$— attached to X$_1$.

What is called "left part" of a radical is for example when A is —(C=O)—NR$_5$—, —(C=O)—, and the "right part" is —NR$_5$—.

Preferably, A is such as the left part of the possible values of A (i.e. in particular —(C=N) from —(C=N)—R$_{49}$, —(C=O) from —(C=O)—NR$_5$, —(C=S) from —(C=S)—NR$_5$, —SO$_2$ from —SO$_2$—NR$_5$—, etc) is attached to X$_1$. Alternatively, A is such as the right part of the possible values of A (i.e. in particular (R$_{49}$)— from —(C=N)R$_{49}$, (NR$_5$)— from —(C=O)—NR$_5$, —NR$_5$ from —(C=S)—NR$_5$, —NR$_5$— from —SO$_2$—NR$_5$—, etc) is attached to X$_1$.

Preferably, X$_1$ is such as the left part of the possible values of X$_1$ (i.e. in particular —O from —O—C$_{1-6}$alkyl, —S from —S—C$_{1-6}$alkyl, —NR$_3$ from —NR$_3$—(C=O) and —NR$_3$—C$_{1-6}$alkyl, —SO$_2$ from —SO$_2$—NR$_3$, etc) is attached to the Z$_1$-Z$_5$ aryl or heteroaryl moiety. Alternatively, X$_1$ is such as the right part of the possible values of X$_1$ (i.e. in particular (C$_{1-6}$alkyl)- from —O—C$_{1-6}$alkyl, —S—C$_{1-6}$alkyl and —NR$_3$—C$_{1-6}$alkyl, —(C=O) from —NR$_3$—(C=O), (NR$_3$)— from —SO$_2$—NR$_3$, etc) is attached to the Z$_1$-Z$_5$ aryl or heteroaryl moiety.

Preferably, X$_2$ is such as the left part of the possible values of X$_2$ (i.e. in particular —O from —O—C$_{1-6}$alkyl, —S from —S—C$_{1-6}$alkyl, —(C=O) from —(C=O)—NR$_2$, —NR$_2$ from —NR$_2$—C$_{1-6}$alkyl, —SO$_2$ from —SO$_2$—NR$_2$, etc) is attached to the pyrazolopyrimidine moiety. Alternatively, X$_2$ is such as the right part of the possible values of X$_2$ (i.e. in particular (C$_{1-6}$alkyl)- from —O—C$_{1-6}$alkyl, —S—C$_{1-6}$alkyl and —NR$_2$—C$_{1-6}$alkyl, (NR$_2$)— from —(C=O)—NR$_2$ and —SO$_2$—NR$_2$, etc) is attached to the pyrazolopyrimidine moiety. The same principle applies to all the radicals of the invention unless specified otherwise.

When describing the compounds of the invention, the terms used are to be construed in accordance with the following definitions, unless a context dictates otherwise:

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, C$_{1-6}$alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. C$_1$-C$_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopropyl, cyclobutyl, cyclopentyl, and cyclohexyl.

The term "optionally substituted alkyl" refers to an alkyl group optionally substituted with one or more substituents (for example 1 to 3 substituents, for example 1, 2 or 3 substituents or 1 to 2 substituents) at any available point of attachment. Non-limiting examples of such substituents include -halo, —OH, primary and secondary amides, —O—C$_{1-6}$alkyl, —S—C$_{1-6}$alkyl, heteroaryl, aryl, and the like.

The term "cycloalkyl" by itself or as part of another substituent is a cyclic alkyl group, that is to say, a monovalent, saturated, or unsaturated hydrocarbyl group having a cyclic structure. Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms. Examples of cycloalkyl groups include but are not limited to cyclopropyl, cyclobutyl, cyclopentyl, cyclohexyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom. To illustrate this applying the asterisk nomenclature of this invention, a C$_3$ alkylene group may be for example *—CH$_2$CH$_2$CH$_2$—*, *—CH(—CH$_2$CH$_3$)—*, or *—CH$_2$CH(—CH$_3$)—*. Likewise a C$_3$ cycloalkylene group may be

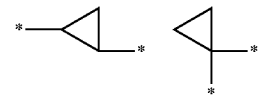

The terms "heterocycle" as used herein by itself or as part of another group refer to non-aromatic, fully saturated or partially unsaturated cyclic groups (for example, 3 to 6 membered monocyclic ring systems, or 8-10 membered bicyclic rings) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, and tetrahydrofuranyl.

8-10 membered heterocyclic groups are also meant to include spiro-groups, which are bicyclic compounds with both rings connected through a single atom, such as for example spiro[4.5]decane, which is a spiro compound consisting of a cyclohexane ring and a cyclopentane ring.

The term "aryl" as used herein refers to a polyunsaturated, aromatic hydrocarbyl group having from 5-10 atoms. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl; in particular phenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment, selected from those defined above for substituted alkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 10 carbon-atom aromatic rings in which one or more carbon atoms can be replaced by oxygen, nitrogen or sulfur atoms. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted alkyl.

The term "halo" or "halogen" as a group or part of a group is generic for fluoro, chloro, bromo, or iodo, as well as any suitable isotope thereof.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent.

Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

In addition, the invention includes isotopically-labelled compounds and salts, which are identical to compounds of formula (I), but for the fact that one or more atoms are replaced by an atom having an atomic mass or mass number different from the atomic mass or mass number most commonly found in nature. Examples of isotopes that can be incorporated into compounds of formula (I) are isotopes of hydrogen, carbon, nitrogen, fluorine, such as $^3$H, $^{11}$C, $^{13}$N, $^{14}$C, $^{15}$O and $^{18}$F. Such isotopically-labelled compounds of formula (I) are useful in drug and/or substrate tissue distribution assays. For example $^{11}$C and $^{18}$F isotopes are particularly useful in PET (Positron Emission Tomography). PET is useful as a diagnostic or treatment follow-up tool that can be applied in a translational manner in a preclinical and clinical setting. It also has applications in PK determination of compounds, including biodistribution. Isotopically labeled compounds of formula (I) can generally be prepared by carrying out the procedures disclosed below, by substituting a readily available non-isotopically labeled reagent with an isotopically labeled reagent.

Whenever used in the present invention the term "compounds of the invention" or a similar term is meant to include the compounds of general Formula I and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a particular embodiment, the present invention provides compounds of Formula I or a stereoisomer, tautomer, racemic, metabolite, pro- or predrug, salt, hydrate, N-oxide form, or solvate thereof; for use in the diagnosis prevention and/or treatment of a SIK-kinase associated disease; wherein one or more of the following applies $A_1$ and $A_2$ are selected from C and N; wherein when $A_1$ is C, then $A_2$ is N; and wherein when $A_2$ is C, then $A_1$ is N;

$R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;

$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{29}R_{30}$, —(C=S)—$NR_{29}R_{30}$, —$C_{3-6}$cycloalkyl -$Het_2$, —$Ar_3$, —(C=O)-$Het_2$, —(C=S)-$Het_2$, —(C=O)—$Ar_3$, —(C=S)—$Ar_3$, —(C=O)—$C_{3-6}$cycloalkyl, —(C=S)—$C_{3-6}$cycloalkyl and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_2$, —$Ar_3$, and —$NR_{15}R_{16}$;

$R_4$ is independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —$Ar_8$ and -$Het_4$;

$R_5$ and $R_7$ are each independently selected from —H, —OH, -halo, —$C_{1-6}$alkyl, —O—$C_{1-6}$alkyl, —S—$C_{1-6}$alkyl, -$Het_9$, —$Ar_1$, —$C_{3-6}$cycloalkyl, —$SO_2$—$Ar_1$, —$SO_2$—$SO_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$alkyl, —O—(C=S)—$C_{1-6}$alkyl, —(C=O)—O—$C_{1-6}$alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —$Ar_1$, -$Het_9$, and —$NR_{23}R_{24}$;

$R_6$ is selected from —$C_{1-6}$alkyl, —$SO_2$, —$SO_2$—$C_{1-6}$alkyl, —$SO_2$—$C_{3-6}$cycloalkyl, —(C=O), —(C=O)—$C_{1-6}$alkyl, —(C=O)—$C_{2-6}$alkenyl, —(C=O)—O—$C_{1-6}$alkyl, —(C=O)-$Het_6$, —(C=O)—$Ar_6$, —(C=O)—$C_{3-6}$cycloalkyl, —(C=O)—$NR_{31}R_{32}$, —(C=O)—$NR_{31}$—(C=O)—$R_{32}$, —(C=S), —(C=S)—$C_{1-6}$alkyl, —(C=S)—$C_{2-6}$alkenyl, —(C=S)—O—$C_{1-6}$alkyl, —(C=S)-$Het_6$, —(C=S)—$Ar_6$, —(C=S)—$C_{3-6}$cycloalkyl, —(C=S)—$NR_{31}R_{32}$, —(C=S)—$NR_{31}$—(C=S)—$R_{32}$, -$Het_6$, —$Ar_6$, and —$C_{3-6}$cycloalkyl; wherein each of said —$C_{1-6}$alkyl is optionally and independently substituted with from 1 to 3 substituents selected from =O, -halo, —OH, —O—$C_{1-6}$alkyl, —S—$C_{1-6}$alkyl, —$C_{3-6}$cycloalkyl, -$Het_6$, —$Ar_6$, —$NR_{25}R_{26}$, —(C=O)—$NR_{25}R_{26}$, —$NR_{33}$(C=O)—$NR_{25}R_{26}$, —(C=S)—$NR_{25}R_{26}$, and —$NR_{33}$(C=S)—$NR_{25}R_{26}$; and wherein each of said —$C_{3-6}$cycloalkyl is optionally and independently substituted with from 1 to 3 substituents selected from —$C_{1-6}$alkyl, =O, -halo, —OH, —O—$C_{1-6}$alkyl, —S—$C_{1-6}$alkyl, -$Het_{12}$, —$Ar_{11}$, and —$NR_{53}R_{54}$, —(C=O)—$NR_{53}R_{54}$, —$NR_{55}$(C=O)—$NR_{53}R_{54}$, —(C=S)—$NR_{53}R_{54}$, and —$NR_{55}$(C=S)—$NR_{53}R_{54}$;

$R_8$ is selected from —$NR_{34}$—(C=O)—$R_{35}$, —$NR_{34}$—(C=S)—$R_{35}$, —$NR_{36}$—(C=O)—$NR_{34}R_{35}$, —$NR_{36}$—(C=S)—$NR_{34}R_{35}$, —$NR_{34}$—($SO_2$)—$R_{35}$, —$NR_{34}$—(C=O)—O—$R_{35}$, —$NR_{34}$—(C=S)—O—$R_{35}$, —O—(C=O)—$NR_{34}R_{35}$, and —O—(C=S)—$NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_5$ and -$Het_7$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_7$, —$Ar_5$ and —$NR_{51}R_{52}$;

$R_{51}$ and $R_{52}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar^{10}$ and -$Het_{10}$;

$R_{42}$ is selected from —H, —OH, -halo, —$C_{1-6}$alkyl, —O—$C_{1-6}$alkyl, —S—$C_{1-6}$alkyl, —$NR_{46}R_{47}$, —$C_{3-6}$cycloalkyl, —$Ar_9$ and -$Het_8$;

$R_{43}$ is selected from —H —$C_{1-6}$alkyl, and —$C_{3-6}$cycloalkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_5$, —$C_{3-6}$cycloalkyl —$Ar_4$, and —$NR_{44}R_{45}$;

A is selected from —$(CH_2)_n$—Y—$(CH_2)_m$—, —(C=O)—, —(C=S)—, —(C=N)—$R_{49}$—, —($SO_2$)—, —$SO_2$—$NR_5$—, —(C=O)—$NR_5$—, —(C=S)—$NR_5$—, —$NR_5$—(C=O)—$NR_7$—, —$NR_5$—(C=S)—$NR_7$—, —$NR_6$—, —$NR_5$—(C=O)—O—, —$NR_5$—(C=S)—O—, and —$CHR_8$—;

$X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$alkyl-$NR_3$—, —$NR_3$—, —(C=O)—, —$NR_3$—(C=O)—$NR_{48}$—, —$NR_3$—$C_{1-6}$alkyl-, —$NR_3$—$SO_2$—, —$NR_3$—(C=O)—$C_{1-6}$alkyl-, —(C=O)—$NR_3$—$C_{1-6}$alkyl-, —O—$C_{1-6}$alkyl-O—$C_{1-6}$alkyl- and —$C_{1-6}$alkyl-$NR_3$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{37}R_{38}$;

$X_2$ is selected from —$C_{1-6}$alkyl-, —O—$C_{1-6}$alkyl-, —S—$C_{1-6}$alkyl-, —(C=O)—, —$NR_2$—(C=O)—, —$C_{1-6}$alkyl-$NR_2$—, —$NR_2$—, —(C=O)—, —$NR_2$—(C=O)—$NR_{50}$—, —$NR_2$—$C_{1-6}$alkyl-, —$NR_2$—$SO_2$—, —$NR_2$—(C=O)—$C_{1-6}$alkyl-, —(C=O)—$NR_2$—$C_{1-6}$alkyl-, —O—$C_{1-6}$alkyl-O—$C_{1-6}$alkyl- and —$C_{1-6}$alkyl-$NR_2$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{39}R_{40}$;

Y is selected from a direct bond, —$CHR_{42}$—, —O—, —S—, and —$NR_{43}$—;

$Ar_1$, $Ar_2$, $Ar_3$, $Ar_4$, $Ar_5$, $Ar_6$, $Ar_7$, $Ar_8$, $Ar_9$, $Ar_{10}$ and $Ar_{11}$ are each independently a 5- to 10-membered aromatic heterocycle optionally comprising 1 or 2 heteroatoms selected from O, N and S; each of said $Ar_1$, $Ar_2$, $Ar_3$, $Ar_4$, $Ar_5$, $Ar_6$, $Ar_7$, $Ar_8$, $Ar_9$, and $Ar_{10}$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, —OH, —$C_{1-6}$alkyl, —O$C_{1-6}$alkyl, —S$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and m and n are each independently 1, 2, 3, or 4.

In particular, $X_1$, and $X_2$ as used herein, represent biradicals, which taken together with the radicals to which they are attached form a macrocyclic pyrazolopyrimidine compound. Said biradicals may be present in either of both directions in the macrocyclic pyrazolopyrimidine, but are preferably present in the direction as described below:

Referring to formula I:

$X_1$ is selected from the list comprising *—$C_{1-6}$alkyl-, *—O—$C_{1-6}$alkyl-, *—S—$C_{1-6}$alkyl-, *—(C=O)—, —NR$_3$—(C=O)—, *—$C_{1-6}$alkyl-NR$_3$—, *—NR$_3$—, *—(C=O)—, *—NR$_3$—(C=O)—NR$_{48}$—, *—NR$_3$—$C_{1-6}$alkyl-, *—NR$_3$—SO$_2$—, *—NR$_3$—(C=O)—$C_{1-6}$alkyl-, *—(C=O)—NR$_3$—$C_{1-6}$alkyl-, *—O—$C_{1-6}$alkyl-O—$C_{1-6}$alkyl- and *—$C_{1-6}$alkyl-NR$_3$—$C_{1-6}$alkyl-; wherein said biradical is preferably attached to the aryl or heteroaryl moiety via *;

$X_2$ is selected from the list comprising *—$C_{1-6}$alkyl-, *—O—$C_{1-6}$alkyl-, *—S—$C_{1-6}$alkyl-, *—(C=O)—, *—NR$_2$—(C=O)—, *—$C_{1-6}$alkyl-NR$_2$—, *—NR$_2$—, *—(C=O)—, *—NR$_2$—(C=O)—NR$_{50}$—, *—NR$_2$—$C_{1-6}$alkyl-, *—NR$_2$—SO$_2$—, *—NR$_2$—(C=O)—$C_{1-6}$alkyl-, *—(C=O)—NR$_2$—$C_{1-6}$alkyl-, *—O—$C_{1-6}$alkyl-O—$C_{1-6}$alkyl- and *—$C_{1-6}$alkyl-NR$_2$—$C_{1-6}$alkyl-; wherein said biradical is preferably attached to the pyrazolopyrimidine moiety via *;

In a preferred embodiment, the present invention provides compounds of formula I or a stereoisomer, tautomer, racemic, metabolite, pro- or predrug, salt, hydrate, N-oxide form, or solvate thereof, for use in the diagnosis, prevention and/or treatment of a SIK-kinase associated disease wherein $A_1$ is C and $A_2$ is N;

$R_1$ and $R_{41}$ are each independently selected from —H, -halo, —OH, —$C_{1-6}$alkyl, —O—$C_{1-6}$alkyl, —S—$C_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —$C_{3-6}$cycloalkyl, —Ar$_7$ and -Het$_1$; wherein each of said —$C_{1-6}$alkyl is optionally and independently substituted with from 1 to 3 substituents selected from -halo, —OH, —NR$_{11}$R$_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—NR$_{27}$R$_{28}$, —(C=S)—NR$_{27}$R$_{28}$, —$C_{3-6}$cycloalkyl, -Het$_3$, —Ar$_2$, —(C=O)-Het$_3$, —(C=S)-Het$_3$, —(C=O)—Ar$_2$, —(C=S)—Ar$_2$, —(C=O)—$C_{3-6}$cycloalkyl, —(C=S)—$C_{3-6}$cycloalkyl, and —SO$_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -Het$_3$, —Ar$_2$, and —NR$_{13}$R$_{14}$;

$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—NR$_{29}$R$_{30}$, —(C=S)—NR$_{29}$R$_{30}$, —$C_{3-6}$cycloalkyl -Het$_2$, —Ar$_3$, —(C=O)-Het$_2$, —(C=S)-Het$_2$, —(C=O)—Ar$_3$, —(C=S)—Ar$_3$, —(C=O)—$C_{3-6}$cycloalkyl, —(C=S)—$C_{3-6}$cycloalkyl and —SO$_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -Het$_2$, —Ar$_3$, and —NR$_{15}$R$_{16}$;

$R_4$ is independently selected from -halo, —OH, —$C_{1-6}$alkyl, —O—$C_{1-6}$alkyl, —S—$C_{1-6}$alkyl, —NR$_{17}$R$_{18}$, —$C_{3-6}$cycloalkyl, —Ar$_8$ and -Het$_4$;

$R_5$ and $R_7$ are each independently selected from —H, —OH, -halo, —$C_{1-6}$alkyl, —O—$C_{1-6}$alkyl, —S—$C_{1-6}$alkyl, -Het$_9$, —Ar$_1$, —$C_{3-6}$cycloalkyl, —SO$_2$—Ar$_1$, —SO$_2$, —SO$_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$alkyl, —O—(C=S)—$C_{1-6}$alkyl, —(C=O)—O—$C_{1-6}$alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —Ar$_1$, -Het$_9$, and —NR$_{23}$R$_{24}$;

$R_6$ is selected from —$C_{1-6}$alkyl, —SO$_2$, —SO$_2$—$C_{1-6}$alkyl, —SO$_2$—$C_{3-6}$cycloalkyl, —(C=O), —(C=O)—$C_{1-6}$alkyl, —(C=O)—$C_{2-6}$alkenyl, —(C=O)—O—$C_{1-6}$alkyl, —(C=O)-Het$_6$, —(C=O)—Ar$_6$, —(C=O)—$C_{3-6}$cycloalkyl, —(C=O)—NR$_{31}$R$_{32}$, —(C=O)—NR$_{31}$—(C=O)—R$_{32}$, —(C=S), —(C=S)—$C_{1-6}$alkyl, —(C=S)—$C_{2-6}$alkenyl, —(C=S)—O—$C_{1-6}$alkyl, —(C=S)-Het$_6$, —(C=S)—Ar$_6$, —(C=S)—$C_{3-6}$cycloalkyl, —(C=S)—NR$_{31}$R$_{32}$, —(C=S)—NR$_{31}$—(C=S)—R$_{32}$, -Het$_6$, —Ar$_6$, and —$C_{3-6}$cycloalkyl; wherein each of said —$C_{1-6}$alkyl is optionally and independently substituted with from 1 to 3 substituents selected from =O, -halo, —OH, —O—$C_{1-6}$alkyl, —S—$C_{1-6}$alkyl, —$C_{3-6}$cycloalkyl, -Het$_6$, —Ar$_6$, —NR$_{25}$R$_{26}$, —(C=O)—NR$_{25}$R$_{26}$, —NR$_{33}$(C=O)—NR$_{25}$R$_{26}$, —(C=S)—NR$_{25}$R$_{26}$, and —NR$_{33}$(C=S)—NR$_{25}$R$_{26}$; and wherein each of said —$C_{3-6}$cycloalkyl is optionally and independently substituted with from 1 to 3 substituents selected from —$C_{1-6}$alkyl, =O, -halo, —OH, —O—$C_{1-6}$alkyl, —S—$C_{1-6}$alkyl, -Het$_{12}$, —Ar$_{11}$, and —NR$_{53}$R$_{54}$, —(C=O)—NR$_{53}$R$_{54}$, —NR$_{55}$(C=O)—NR$_{53}$R$_{54}$, —(C=S)—NR$_{53}$R$_{54}$, and —NR$_{55}$(C=S)—NR$_{53}$R$_{54}$;

$R_8$ is selected from —NR$_{34}$—(C=O)—R$_{35}$, —NR$_{34}$—(C=S)—R$_{35}$, —NR$_{36}$—(C=O)—NR$_{34}$R$_{35}$, —NR$_{36}$—(C=S)—NR$_{34}$R$_{35}$, —NR$_{34}$—(SO$_2$)—R$_{35}$, —NR$_{34}$—(C=O)—O—R$_{35}$, —NR$_{34}$—(C=S)—O—R$_{35}$, —O—(C=O)—NR$_{34}$R$_{35}$, and —O—(C=S)—NR$_{34}$R$_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —Ar$_5$ and -Het$_7$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_7$, —$Ar_5$ and —$NR_{51}R_{52}$;

$R_{51}$ and $R_{52}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_{10}$ and -$Het_{10}$;

$R_{42}$ is selected from —H, —OH, -halo, —$C_{1-6}$alkyl, —O—$C_{1-6}$alkyl, —S—$C_{1-6}$alkyl, —$NR_{46}R_{47}$, —$C_{3-6}$cycloalkyl, —$Ar_9$ and -$Het_8$;

$R_{43}$ is selected from —H —$C_{1-6}$alkyl, and —$C_{3-6}$cycloalkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_5$, —$C_{3-6}$cycloalkyl —$Ar_4$, and —$NR_{44}R_{45}$;

A is selected from —$(CH_2)_n$—Y—$(CH_2)_m$—, —(C=O)—, —(C=S)—, —(C=N)—$R_{49}$—, —$(SO_2)$—, —$SO_2$—$NR_5$—, —(C=O)—$NR_5$—, —(C=S)—$NR_5$—, —$NR_5$—(C=O)—$NR_7$—, —$NR_5$—(C=S)—$NR_7$—, —$NR_6$—, —$NR_5$—(C=O)—O—, —$NR_5$—(C=S)—O—, and —$CHR_8$—;

$X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$alkyl-$NR_3$—, —$NR_3$—, —(C=O)—, —$NR_3$—(C=O)—$NR_{48}$—, —$NR_3$—$C_{1-6}$alkyl-, —$NR_3$—$SO_2$—, —$NR_3$—(C=O)—$C_{1-6}$alkyl-, —(C=O)—$NR_3$—$C_{1-6}$alkyl-, —O—$C_{1-6}$alkyl-O—$C_{1-6}$alkyl- and —$C_{1-6}$alkyl-$NR_3$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —$NR_{37}R_{38}$;

$X_2$ is selected from —$C_{1-6}$alkyl-, —O—$C_{1-6}$alkyl-, —S—$C_{1-6}$alkyl-, —(C=O)—, —$NR_2$—(C=O)—, —$C_{1-6}$alkyl-$NR_2$—, —$NR_2$—, —(C=O)—, —$NR_2$—(C=O)—$NR_{50}$—, —$NR_2$—$C_{1-6}$alkyl-, —$NR_2$—$SO_2$—, —$NR_2$—(C=O)—$C_{1-6}$alkyl-, —(C=O)—$NR_2$—$C_{1-6}$alkyl-, —O—$C_{1-6}$alkyl-O—$C_{1-6}$alkyl- and —$C_{1-6}$alkyl-$NR_2$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —$NR_{39}R_{40}$;

Y is selected from a direct bond, —$CHR_{42}$—, —O—, —S—, and —$NR_{43}$—;

$Ar_1$, $Ar_2$, $Ar_3$, $Ar_4$, $Ar_5$, $Ar_6$, $Ar_7$, $Ar_8$, $Ar_9$, $Ar_{10}$ and $Ar_{11}$ are each independently a 5- to 10-membered aromatic heterocycle optionally comprising 1 or 2 heteroatoms selected from O, N and S; each of said $Ar_1$, $Ar_2$, $Ar_3$, $Ar_4$, $Ar_5$, $Ar_6$, $Ar_7$, $Ar_8$, $Ar_9$, and $Ar_{10}$ being optionally and independently substituted with from 1 to 3 substituents selected from -halo, —OH, —$C_{1-6}$alkyl, —O—$C_{1-6}$alkyl, —S—$C_{1-6}$alkyl, and —$NR_{19}R_{20}$; wherein each of said —$C_{1-6}$alkyl is optionally and independently substituted with from 1 to 3 -halo;

$Het_1$, $Het_2$, $Het_3$, $Het_4$, $Het_5$, $Het_6$, $Het_7$, $Het_8$, $Het_9$, $Het_{10}$, and $Het_{12}$ are each independently a 4- to 10-membered heterocycle having from 1 to 3 heteroatoms selected from O, N and S, wherein each of said $Het_1$, $Het_2$, $Het_3$, $Het_4$, $Het_5$, $Het_6$, $Het_7$, $Het_8$, $Het_9$, $Het_{10}$, and $Het_{12}$ is optionally and independently substituted with from 1 to 3 substituents selected from -halo, —OH, —$C_{1-6}$alkyl, —$OC_{1-6}$alkyl, —$SC_{1-6}$alkyl, =O, —(C=O)—$C_{1-6}$alkyl, and —$NR_{21}R_{22}$; wherein each of said —$C_{1-6}$alkyl is optionally and independently substituted with from 1 to 3 -halo;

$Z_1$, $Z_2$, $Z_3$, $Z_4$ and $Z_5$ are each independently selected from C and N; and m and n are each independently 1, 2, 3, or 4;

for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, for use in the diagnosis, prevention and/or treatment of a SIK-kinase associated disease wherein $A_1$ is N and $A_2$ is C $R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;

$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;

$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{29}R_{30}$, —(C=S)—$NR_{29}R_{30}$, —$C_{3-6}$cycloalkyl -$Het_2$, —$Ar_3$, —(C=O)-$Het_2$, —(C=S)-$Het_2$, —(C=O)—$Ar_3$, —(C=S)—$Ar_3$, —(C=O)—$C_{3-6}$cycloalkyl, —(C=S)—$C_{3-6}$cycloalkyl and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_2$, —$Ar_3$, and —$NR_{15}R_{16}$;

$R_4$ is independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —$Ar_8$ and -$Het_4$;

$R_5$ and $R_7$ are each independently selected from —H, —OH, -halo, —$C_{1-6}$alkyl, —O—$C_{1-6}$alkyl, —S—$C_{1-6}$alkyl, -$Het_9$, —$Ar_1$, —$C_{3-6}$cycloalkyl, —$SO_2$—$Ar_1$, —$SO_2$, —$SO_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$alkyl, —O—(C=S)—$C_{1-6}$alkyl, —(C=O)—O—$C_{1-6}$alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —$Ar_1$, -$Het_9$, and —$NR_{23}R_{24}$;

$R_6$ is selected from —$C_{1-6}$alkyl, —$SO_2$, —$SO_2$—$C_{1-6}$alkyl, —$SO_2$—$C_{3-6}$cycloalkyl, —(C=O), —(C=O)—$C_{1-6}$alkyl, —(C=O)—$C_{2-6}$alkenyl, —(C=O)—O—$C_{1-6}$alkyl, —(C=O)-$Het_6$, —(C=O)—$Ar_6$, —(C=O)—$C_{3-6}$cycloalkyl, —(C=O)—$NR_{31}R_{32}$, —(C=O)—$NR_{31}$—(C=O)—$R_{32}$, —(C=S), —(C=S)—$C_{1-6}$alkyl, —(C=S)—$C_{2-6}$alkenyl, —(C=S)—O—$C_{1-6}$alkyl, —(C=S)-$Het_6$, —(C=S)—$Ar_6$, —(C=S)—$C_{3-6}$cycloalkyl, —(C=S)—$NR_{31}R_{32}$, —(C=S)—$NR_{31}$—(C=S)—$R_{32}$, -$Het_6$, —$Ar_6$, and —$C_{3-6}$cycloalkyl;

wherein each of said —$C_{1-6}$alkyl is optionally and independently substituted with from 1 to 3 substituents selected from =O, -halo, —OH, —O—$C_{1-6}$alkyl, —S—$C_{1-6}$alkyl, —$C_{3-6}$cycloalkyl, -Het$_6$, —Ar$_6$, —NR$_{25}$R$_{26}$, —(C=O)—NR$_{25}$R$_{26}$, —NR$_{33}$(C=O)—NR$_{25}$R$_{26}$, —(C=S)—NR$_{25}$R$_{26}$, and —NR$_{33}$(C=S)—NR$_{25}$R$_{26}$; and wherein each of said —$C_{3-6}$cycloalkyl is optionally and independently substituted with from 1 to 3 substituents selected from —$C_{1-6}$alkyl, =O, -halo, —OH, —O—$C_{1-6}$alkyl, —S—$C_{1-6}$alkyl, -Het$_{12}$, —Ar$_{11}$, and —NR$_{53}$R$_{54}$, —(C=O)—NR$_{53}$R$_{54}$, —NR$_{55}$(C=O)—NR$_{53}$R$_{54}$, —(C=S)—NR$_{53}$R$_{54}$, and —NR$_{55}$(C=S)—NR$_{53}$R$_{54}$;

R$_8$ is selected from —NR$_{34}$—(C=O)—R$_{35}$, —NR$_{34}$—(C=S)—R$_{35}$, —NR$_{36}$—(C=O)—NR$_{34}$R$_{35}$, —NR$_{36}$—(C=S)—NR$_{34}$R$_{35}$, —NR$_{34}$—(SO$_2$)—R$_{35}$, —NR$_{34}$—(C=O)—O—R$_{35}$, —NR$_{34}$—(C=S)—O—R$_{35}$, —O—(C=O)—NR$_{34}$R$_{35}$, and —O—(C=S)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$, R$_{40}$, R$_{44}$, R$_{45}$, R$_{46}$, R$_{47}$, R$_{48}$, R$_{49}$, R$_{50}$, R$_{53}$, R$_{54}$ and R$_{55}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —Ar$_5$ and -Het$_7$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -Het$_7$, —Ar$_5$ and —NR$_{51}$R$_{52}$;

R$_{51}$ and R$_{52}$ are each independently selected from —H, -halo, —OH, —$C_{1-6}$alkyl, —O—$C_{1-6}$alkyl, —S—$C_{1-6}$alkyl, —$C_{3-6}$cycloalkyl, —Ar$_{10}$ and -Het$_{10}$;

R$_{42}$ is selected from —H, —OH, -halo, —$C_{1-6}$alkyl, —O—$C_{1-6}$alkyl, —S—$C_{1-6}$alkyl, —NR$_{46}$R$_{47}$, —$C_{3-6}$cycloalkyl, —Ar$_9$ and -Het$_8$;

R$_{43}$ is selected from —H —$C_{1-6}$alkyl, and —$C_{3-6}$cycloalkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -Het$_5$, —$C_{3-6}$cycloalkyl —Ar$_4$, and —NR$_{44}$R$_{45}$;

A is selected from —(CH$_2$)$_n$—Y—(CH$_2$)$_m$—, —(C=O)—, —(C=S)—, —(C=N)—R$_{49}$—, —(SO$_2$)—, —SO$_2$—NR$_5$—, —(C=O)—NR$_5$—, —(C=S)—NR$_5$—, —NR$_5$—(C=O)—NR$_7$—, —NR$_5$—(C=S)—NR$_7$—, —NR$_6$—, —NR$_5$—(C=O)—O—, —NR$_5$—(C=S)—O—, and —CHR$_8$—;

X$_1$ is selected from —$C_{1-6}$alkyl-, —O—$C_{1-6}$alkyl-, —S—$C_{1-6}$alkyl-, —(C=O)—, —NR$_3$—(C=O)—, —$C_{1-6}$alkyl-NR$_3$—, —NR$_3$—, —(C=O)—, —NR$_3$—(C=O)—NR$_{48}$—, —NR$_3$—$C_{1-6}$alkyl-, —NR$_3$—SO$_2$—, —NR$_3$—(C=O)—$C_{1-6}$alkyl-, —(C=O)—NR$_3$—$C_{1-6}$alkyl-, —O—$C_{1-6}$alkyl-O—$C_{1-6}$alkyl- and —$C_{1-6}$alkyl-NR$_3$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl, and —NR$_{37}$R$_{38}$;

X$_2$ is selected from —$C_{1-6}$alkyl-, —O—$C_{1-6}$alkyl-, —S—$C_{1-6}$alkyl-, —(C=O)—, —NR$_2$—(C=O)—, —$C_{1-6}$alkyl-NR$_2$—, —NR$_2$—, —(C=O)—, —NR$_2$—(C=O)—NR$_{50}$—, —NR$_2$—$C_{1-6}$alkyl-, —NR$_2$—SO$_2$—, —NR$_2$—(C=O)—$C_{1-6}$alkyl-, —(C=O)—NR$_2$—$C_{1-6}$alkyl-, —O—$C_{1-6}$alkyl-O—$C_{1-6}$alkyl- and —$C_{1-6}$alkyl-NR$_2$—$C_{1-6}$alkyl-; wherein each of said —$C_{1-6}$alkyl- is optionally and independently substituted with from 1 to 3 substituents selected from -halo, —OH, —$C_{1-6}$alkyl, —O—$C_{1-6}$alkyl, —S—$C_{1-6}$alkyl, -phenyl and —NR$_{39}$R$_{40}$;

Y is selected from a direct bond, —CHR$_{42}$—, —O—, —S—, and —NR$_{43}$—;

Ar$_1$, Ar$_2$, Ar$_3$, Ar$_4$, Ar$_5$, Ar$_6$, Ar$_7$, Ar$_8$, Ar$_9$, Ar$_{10}$ and Ar$_{11}$ are each independently a 5- to 10-membered aromatic heterocycle optionally comprising 1 or 2 heteroatoms selected from O, N and S; each of said Ar$_1$, Ar$_2$, Ar$_3$, Ar$_4$, Ar$_5$, Ar$_6$, Ar$_7$, Ar$_8$, Ar$_9$, and Ar$_{10}$ being optionally and independently substituted with from 1 to 3 substituents selected from -halo, —OH, —$C_{1-6}$alkyl, —O—$C_{1-6}$alkyl, —S—$C_{1-6}$alkyl, and —NR$_{19}$R$_{20}$; wherein each of said —$C_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, —OH, —$C_{1-6}$alkyl, —O$C_{1-6}$alkyl, —S$C_{1-6}$alkyl, =O, —(C=O)—$C_{1-6}$alkyl, and —NR$_{21}$R$_{22}$; wherein each of said —$C_{1-6}$alkyl is optionally and independently substituted with from 1 to 3 -halo;

Z$_1$, Z$_2$, Z$_3$, Z$_4$ and Z$_5$ are each independently selected from C and N; and m and n are each independently 1, 2, 3, or 4.

In a further embodiment, the present invention provides a compound of Formula I or a stereoisomer, tautomer, racemic, metabolite, pro- or predrug, salt, hydrate, N-oxide form, or solvate thereof, wherein A$_1$ and A$_2$ are selected from C and N; wherein when A is C, then A$_2$ is N; and wherein when A$_2$ is C, then A$_1$ is N;

R$_1$ and R$_{41}$ are each independently selected from —H, -halo, —OH, —$C_{1-6}$alkyl, and —(C=O)—R$_4$; wherein each of said —$C_{1-6}$alkyl is optionally and independently substituted with from 1 to 3 substituents selected from -halo, —OH, and —O—$C_{1-6}$alkyl;

R$_2$ is selected from —H and —(C=O)—NR$_{27}$R$_{28}$;

R$_3$ is —H;

R$_4$ is —NR$_{17}$R$_{18}$;

R$_6$ is selected from —$C_{1-6}$alkyl, —(C=O)—$C_{3-6}$cycloalkyl, -Het$_6$, and —$C_{3-6}$cycloalkyl;

wherein each of said —$C_{1-6}$alkyl is optionally and independently substituted with from 1 to 3 substituents selected from —OH, —$C_{3-6}$cycloalkyl, -Het$_6$, —NR$_{25}$R$_{26}$, and —(C=O)—NR$_{25}$R$_{26}$;

and wherein each of said —$C_{3-6}$cycloalkyl is optionally and independently substituted with from 1 to 3 substituents selected from =O R$_{17}$, R$_{18}$, R$_{25}$, R$_{26}$, R$_{27}$, and R$_{28}$ are each independently selected from —H, and —$C_{1-6}$alkyl; wherein each of said —$C_{1-6}$alkyl is optionally and independently substituted with from 1 to 3 substituents selected from -Het$_7$, and —NR$_{51}$R$_{52}$;

R$_{51}$ and R$_{52}$ are each —$C_{1-6}$alkyl;

R$_{43}$ is —H;

A is selected from —(CH$_2$)$_n$—Y—(CH$_2$)$_m$—, and —NR$_6$—;

X$_1$ is selected from —O—$C_{1-6}$alkyl-, —S—$C_{1-6}$alkyl- and —$C_{1-6}$alkyl-NR$_3$—;

X$_2$ is selected from —O—$C_{1-6}$alkyl-, —S—$C_{1-6}$alkyl-, and —$C_{1-6}$alkyl-NR$_2$;

Y is —NR$_{43}$—;

Het$_6$ and Het$_7$ are each independently selected from a 5- to 10-membered heterocycle having from 1 to 3 heteroatoms selected from O, N and S;

$Z_1$, $Z_2$, $Z_3$, $Z_4$ and $Z_5$ are each independently selected from C and N; and m and n are each independently 1, 2, 3, or 4;

for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, wherein $A_1$ is C and $A_2$ is N;

$R_1$ and $R_{41}$ are each independently selected from —H, -halo, —OH, —$C_{1-6}$alkyl, and —(C=O)—$R_4$; wherein each of said —$C_{1-6}$alkyl is optionally and independently substituted with from 1 to 3 substituents selected from -halo, —OH, and —O—$C_{1-6}$alkyl;

$R_2$ is selected from —H and —(C=O)—$NR_{27}R_{28}$;

$R_3$ is —H;

$R_4$ is —$NR_{17}R_{18}$;

$R_6$ is selected from —$C_{1-6}$alkyl, —(C=O)—$C_{3-6}$cycloalkyl, -$Het_6$, and —$C_{3-6}$cycloalkyl;
wherein each of said —$C_{1-6}$alkyl is optionally and independently substituted with from 1 to 3 substituents selected from —OH, —$C_{3-6}$cycloalkyl, -$Het_6$, —$NR_{25}R_{26}$, and —(C=O)—$NR_{25}R_{26}$;
and wherein each of said —$C_{3-6}$cycloalkyl is optionally and independently substituted with from 1 to 3 substituents selected from =O $R_{17}$, $R_{18}$, $R_{25}$, $R_{26}$, $R_{27}$, and $R_{28}$ are each independently selected from —H, and —$C_{1-6}$alkyl; wherein each of said —$C_{1-6}$alkyl is optionally and independently substituted with from 1 to 3 substituents selected from -$Het_7$, and —$NR_{51}R_{52}$;

$R_{51}$ and $R_{52}$ are each —$C_{1-6}$alkyl;

$R_{43}$ is —H;

A is selected from —$(CH_2)_n$—Y—$(CH_2)_m$—, and —$NR_6$—;

$X_1$ is selected from —O—$C_{1-6}$alkyl-, —S—$C_{1-6}$alkyl- and —$C_{1-6}$alkyl-$NR_3$—;

$X_2$ is selected from —O—$C_{1-6}$alkyl-, —S—$C_{1-6}$alkyl-, and —$C_{1-6}$alkyl-$NR_2$;

Y is —$NR_{43}$—;

$Het_6$ and $Het_7$ are each independently selected from a 5- to 10-membered heterocycle having from 1 to 3 heteroatoms selected from O, N and S;

$Z_1$, $Z_2$, $Z_3$, $Z_4$ and $Z_5$ are each independently selected from C and N; and m and n are each independently 1, 2, 3, or 4;

for use in the diagnosis, prevention and/or treatment of a SIK-kinase associated disease.

In a further embodiment, the present invention provides a compound of Formula I or a stereoisomer, tautomer, racemic, metabolite, pro- or predrug, salt, hydrate, N-oxide form, or solvate thereof, wherein $A_1$ is N and $A_2$ is C;

$R_1$ and $R_{41}$ are each independently selected from —H, -halo, —OH, —$C_{1-6}$alkyl, and —(C=O)—$R_4$; wherein each of said —$C_{1-6}$alkyl is optionally and independently substituted with from 1 to 3 substituents selected from -halo, —OH, and —O—$C_{1-6}$alkyl;

$R_2$ is selected from —H and —(C=O)—$NR_{27}R_{28}$;

$R_3$ is —H;

$R_4$ is —$NR_{17}R_{18}$;

$R_6$ is selected from —$C_{1-6}$alkyl, —(C=O)—$C_{3-6}$cycloalkyl, -$Het_6$, and —$C_{3-6}$cycloalkyl;
wherein each of said —$C_{1-6}$alkyl is optionally and independently substituted with from 1 to 3 substituents selected from —OH, —$C_{3-6}$cycloalkyl, -$Het_6$, —$NR_{25}R_{26}$, and —(C=O)—$NR_{25}R_{26}$;
and wherein each of said —$C_{3-6}$cycloalkyl is optionally and independently substituted with from 1 to 3 substituents selected from =O $R_{17}$, $R_{18}$, $R_{25}$, $R_{26}$, $R_{27}$, and $R_{28}$ are each independently selected from —H, and —$C_{1-6}$alkyl; wherein each of said —$C_{1-6}$alkyl is optionally and independently substituted with from 1 to 3 substituents selected from -$Het_7$, and —$NR_{51}R_{52}$;

$R_{51}$ and $R_{52}$ are each —$C_{1-6}$alkyl;

$R_{43}$ is —H;

A is selected from —$(CH_2)_n$—Y—$(CH_2)_m$—, and —$NR_6$—;

$X_1$ is selected from —O—$C_{1-6}$alkyl-, —S—$C_{1-6}$alkyl- and —$C_{1-6}$alkyl-$NR_3$—;

$X_2$ is selected from —O—$C_{1-6}$alkyl-, —S—$C_{1-6}$alkyl-, and —$C_{1-6}$alkyl-$NR_2$;

Y is —$NR_{43}$—;

$Het_6$ and $Het_7$ are each independently selected from a 5- to 10-membered heterocycle having from 1 to 3 heteroatoms selected from O, N and S;

$Z_1$, $Z_2$, $Z_3$, $Z_4$ and $Z_5$ are each independently selected from C and N; and m and n are each independently 1, 2, 3, or 4;

for use in the diagnosis, prevention and/or treatment of a SIK-kinase associated disease.

In particular in the compounds according to this invention, the pyrazolopyrimidine or the imidazopyridazine moiety is linked to the aryl or heteroaryl moiety at position $Z_4$ or $Z_5$, in accordance with the numbering as provided in Formula I. Furthermore, the $R_1$ of the compounds according to this invention is preferably linked to the aryl or heteroaryl moiety at position $Z_1$, $Z_2$ or $Z_3$, in accordance with the numbering as provided in Formula I.

In a particular embodiment, the present invention provides a compound selected from the list comprising:

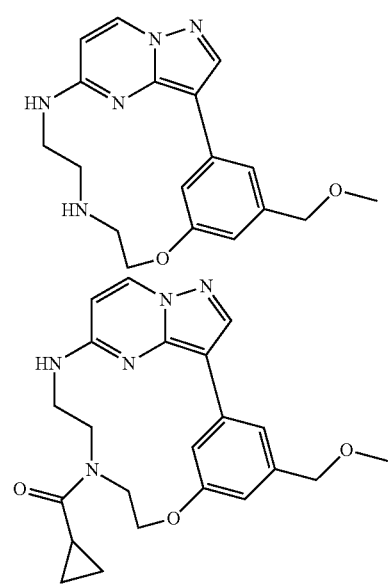

33
-continued
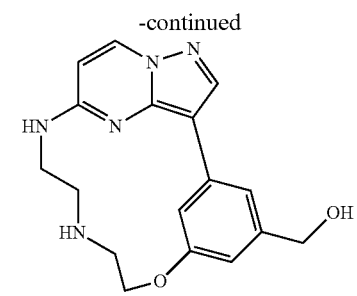
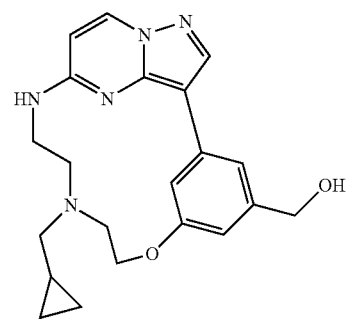
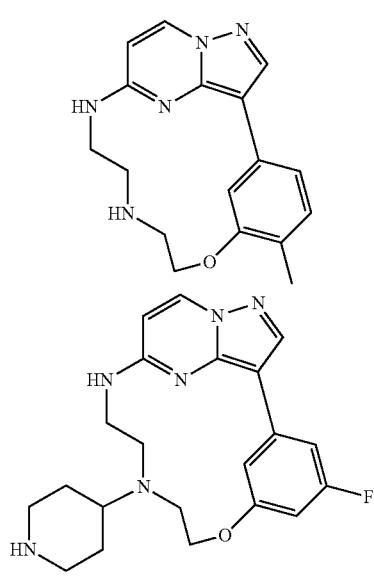
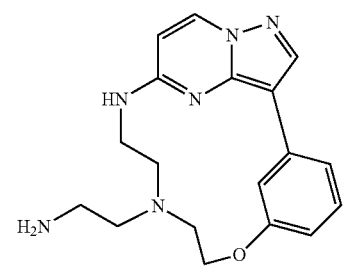
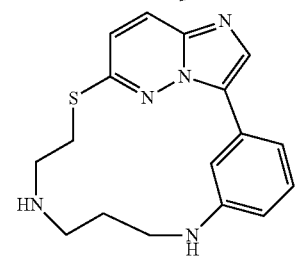
34
-continued
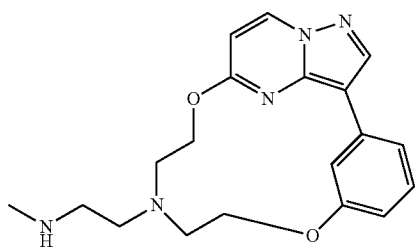
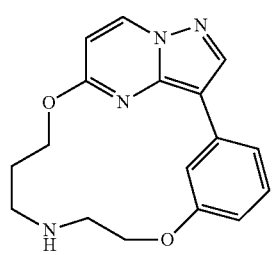
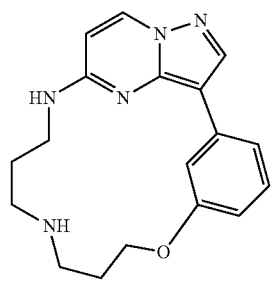
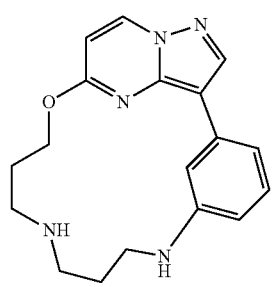
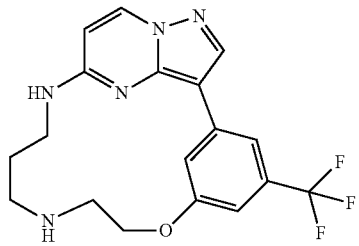
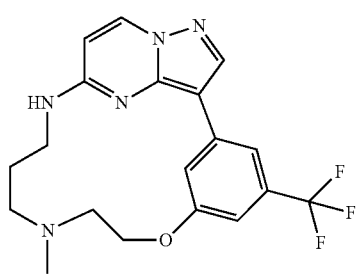

-continued

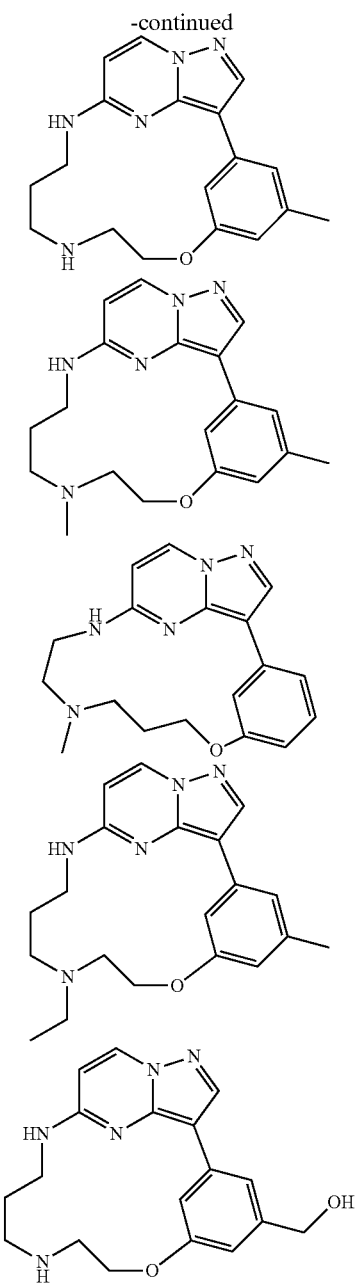

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Method of Treatment

Compounds of formula (I) a stereoisomer, tautomer, racemic, metabolite, pro- or predrug, salt, hydrate, N-oxide form, or solvate thereof, are inhibitors of SIK kinase activity, in particular SIK1, SIK2 and/or SIK3 kinase inhibitors, and are thus believed to be of potential use in the prevention and/or treatment of neurodegenerative disorders, pigmentation-related diseases and cancer, as well as cardiac, metabolic, autoimmune and inflammatory diseases.

In the invention, particular preference is given to compounds of Formula I or any subgroup thereof that in the inhibition assay for SIK described below inhibit kinase activity with an $IC_{50}$ value of less than 10 μM, preferably less than 1 μM, most preferably less than 100 nM.

Said inhibition may be effected in vitro and/or in vivo, and when effected in vivo, is preferably effected in a selective manner, as defined above.

The term "SIK kinase-mediated condition" or "disease", as used herein, means any disease or other deleterious condition in which the SIK kinase, in particular SIK1, SIK2 and/or SIK3 kinase and/or mutants thereof is/are known to play a role. The term "SIK kinase-mediated condition" or "disease" also means those diseases or conditions that are alleviated by treatment with a SIK kinase inhibitor, in particular a SIK1, SIK2 and/or SIK3 kinase inhibitor. Accordingly, another embodiment of the present invention relates to treating or lessening the severity of one or more diseases in which the SIK kinase is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

For local administration, the compounds may advantageously be used in the form of a spray, ointment or transdermal patch or another suitable form for topical, transdermal and/or intradermal administration.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of Formula or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used orally or parenterally.

The invention will now be illustrated by means of the following synthetic and biological examples, which do not limit the scope of the invention in any way.

EXAMPLES

A. Compound Synthesis and Physicochemical Properties

The compounds of this invention can be prepared by any of several standard synthetic processes commonly used by those skilled in the art of organic chemistry. The compounds are generally prepared from starting materials which are either commercially available or prepared by standard means obvious to those skilled in the art.

General Schemes:

As indicated herein before, the present invention provides compounds according to formula I, for use in the diagnosis, prevention and/or treatment of SIK-kinase associated diseases:

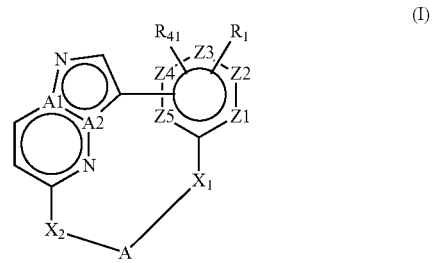

(I)

With reference to the general reaction schemes suitable for preparing said compounds, these compounds can be represented by formulas Ia or Ib respectively, for which the general reaction schemes can be found herein below.

In general the compounds of formula (I) can be prepared as shown in scheme 1 below wherein a pyrazolo[1,5-a]pyrimidine or a imidazo[2,1-f]pyridazine of formula (II) is converted by reaction with a compound of formula (III) into a compound of formula (IV), which is then reacted with a (hetero-)aryl of formula (V) to form a compound of formula (VI). The compound of formula (VI) can then be optionally deprotected if desired before cyclisation to form a compound of formula (VII). The compound of formula (VII) can be optionally converted into a compound of general formula (I).

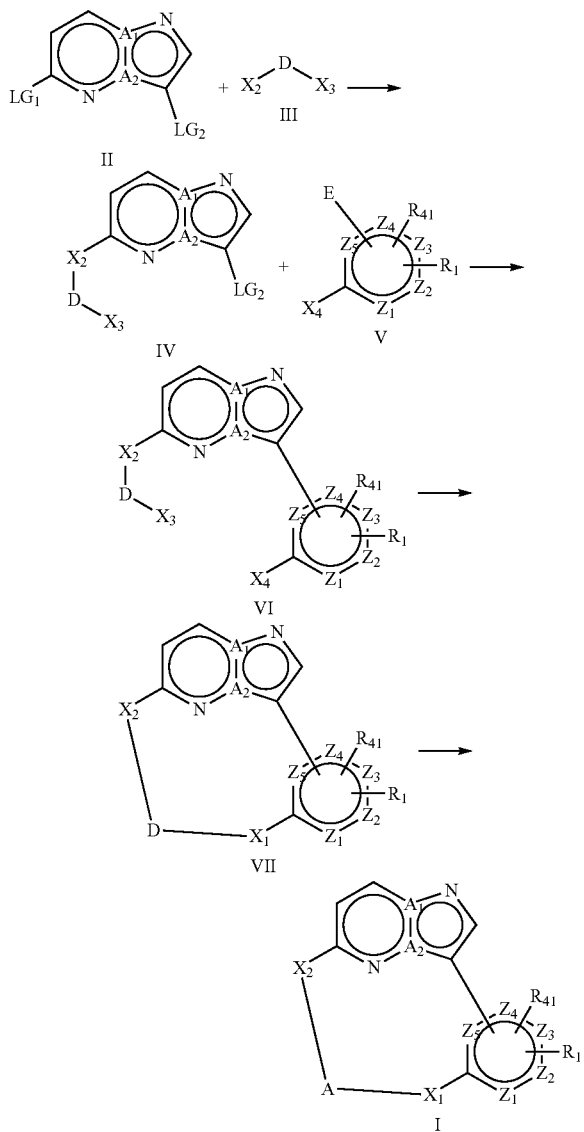

Scheme 1

In the above scheme:
LG$_1$ and LG$_2$ each independently represent suitable leaving or functional groups;
X$_3$ and X$_4$ together with the functional moiety to which they are attached represent an unprotected or a protected functional group which upon reaction (after deprotection) produce together X$_1$ as defined in formula I;
E represents a suitable functional group that can be used to form a direct bond between the (hetero-)aryl group and the scaffold.

D represents a functional group such as A or a protected functional group, which upon further reaction and/or deprotection produces a functional group such as A as defined in formula I;

In the above reaction of the compound of formula (II) with the compound of formula (III) the leaving groups LG$_1$ and LG$_2$ are advantageously a halo group such as a chlorine or a bromine group. The reaction can be affected by a substitution for example by treating the compound of formula (II) with the compound of formula (III) in an organic solvent such as acetonitrile with an appropriate base such as for example diisopropylethylamine at an elevated temperature for example under reflux.

Compounds of formula (III) can be obtained through various selective protection and deprotection steps.

The compound of formula (IV) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofurane at an elevated temperature such as under reflux.

The reaction of the resulting compound (IV) with a (hetero-)aryl compound of formula (V) is advantageously effected through the coupling of a boronic acid E or boronic ester E derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example under reflux.

The resulting compound of formula (VI) can optionally be treated to remove any desired protecting groups for example silyl ether groups such as tert-butyldimethylsilyl groups can be converted to the parent free hydroxy group. Such deprotection can be effected in a conventional manner for example using tetrabutylammonium fluoride in tetrahydrofuran at room temperature. The resulting compound of formula (VI) can also optionally be treated to remove any desired protecting groups for example benzyl groups can be removed in a conventional manner for example using hydrogen gas and palladium on activated charcoal (10%) in a solvent such as methanol at a temperature such as room temperature. The compound of formula (VI) can optionally be treated to remove any desired protecting groups for example tert-butyloxycarbonylamino groups can be converted to the parent free amino group. Such deprotection can be effected in a conventional manner for example by treatment under acidic conditions for example using a 4N acetyl chloride solution in a solvent such as methanol at for example room temperature.

The cyclisation of the compound of formula (VI) can be effected for example under Mitsunobu conditions using for example diisopropyl azodicarboxylate and triphenylphosphine in a solvent mixture such as 2-methyl-1,4-dioxane and toluene at an elevated temperature such as 90° C.

The resulting compound of formula (VII) can optionally be treated to remove any desired protecting groups for example tert-butyloxycarbonylamino groups can be converted to the parent free amino group. Such deprotection can be effected in a conventional manner for example by treatment under acidic conditions for example using a 4N hydrochloric acid solution in methanol at room temperature.

The deprotected compound can optionally be treated to form an amide compound of formula (I). The reaction can advantageously be affected by treatment with an acylchloride and a base such as triethylamine in a solvent such as tetrahydrofuran at room temperature. The reaction can also be affected using for example O-(benzotriazol-1-yl)-N,N,N',N'-tetramethyluronium hexafluorophosphate (HBTU) and diisopropylethylamine in a solvent such as N,N-dimethylformamide at for example room temperature.

Compounds A10, A11, B75, H78, H79, H80, H81, H82, H83, H84, H86, H88, H90, H91, H92, H93, H94, H95, H96, H97 and H100 may be prepared according to the synthesis described in Scheme 1.

The compounds of formula (I) can also be prepared as shown in general scheme 2 below wherein a pyrazolo[1,5-a]pyrimidine or a imidazo[2,1-f]pyridazine of formula (II) is converted by reaction with a compound of formula (VIII) into a compound of formula (IX). The compound of formula (IX) can be optionally be converted into a compound of formula (IV) which is then reacted with a (hetero-)aryl of formula (V) to form a compound of formula (VI). The compound of formula (VI) can then be optionally deprotected if desired before cyclisation to form a compound of formula (VII). The compound of formula (VII) can be optionally converted into a compound of general formula (I).

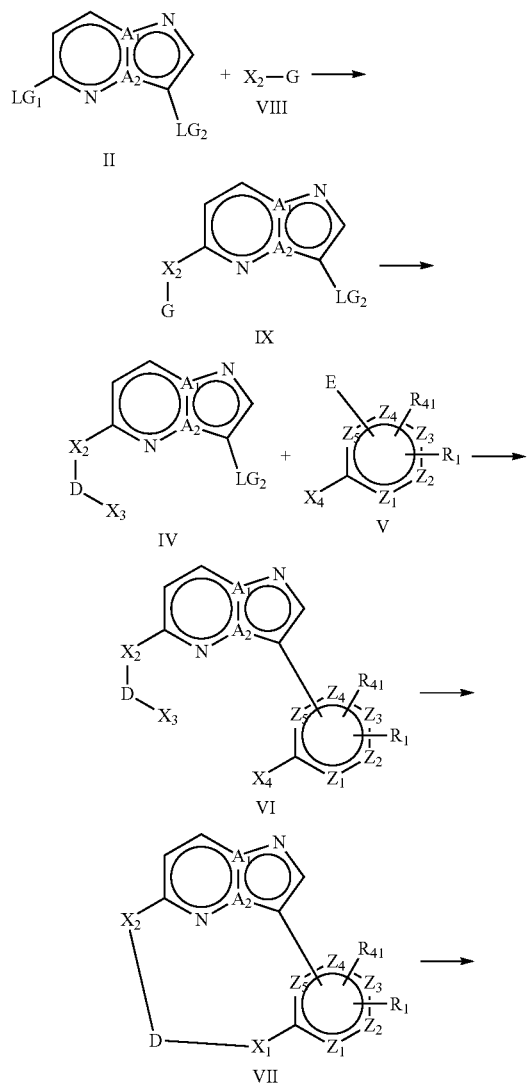

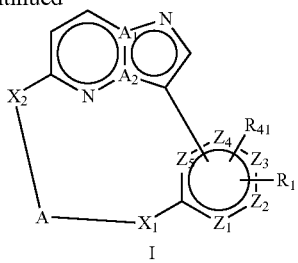

In the above scheme:

$LG_1$ and $LG_2$ each independently represent suitable leaving or functional groups;

E represents a suitable functional group that can be used to form a direct bond between the (hetero-)aryl group and the scaffold.

G represents a suitable functional group or protected functional group, which upon further reaction and/or deprotection produces a functional group such as D;

D represents a functional group such as A or a protected functional group, which upon further reaction and/or deprotection produces a functional group such as A as defined in formula I;

In the above reaction of the compound of formula (II) with the compound of formula (VIII) the leaving groups $LG_1$ and $LG_2$ are advantageously a halo group such as a chlorine or a bromine group. The reaction can be affected by a substitution for example by treating the compound of formula (II) with the compound of formula (VIII) in an organic solvent such as tetrahydrofuran with an appropriate base such as for example sodium hydride at for example room temperature.

Compounds of formula (VIII) can be either commercially acquired or obtained through various selective protection and deprotection steps.

The compounds of formula (IX) can be deprotected using for example acidic conditions such as a 4N hydrochloric acid solution in methanol at room temperature.

The compounds of formula (IX) can be converted into compounds of formula (IV) by using for example a reductive amination. The reaction can be affected by treating the compound of formula (IX) with an alhyde in the presence of a reducing agent such as sodium triacetoxy borohydride and a base such as triethylamine in a solvent such as dichloromethane at for example room temperature.

The reaction of the compound with formula (IV) with a (hetero-)aryl compound of formula (V) is advantageously effected under Suzuki conditions using for example tetrakis(triphenylphosphine)palladium(0) and potassium phosphate tribasic in a solvent mixture such as 1,4-dioxane/water at an elevated temperature for example 80° C.

The resulting compound of formula (VI) can optionally be treated to remove any desired protecting groups for example silyl ether groups such as tert-butyldimethylsilyl groups can be converted to the parent free hydroxy group. Such deprotection can be effected using for example acetic acid in tetrahydrofuran at for example room temperature. The compound of formula (VI) can optionally be treated to remove any desired protecting groups for example tert-butyloxycarbonylamino groups can be converted to the parent free amino group. Such deprotection can be effected in a conventional manner for example by treatment under acidic conditions for example using a 4N acetyl chloride solution in a solvent such as methanol at for example room temperature.

The free hydroxyl group can be converted into a leaving group such as a chloride by reacting the hydroxyl group for example with thionyl chloride in the presence of a base such as pyridine in a solvent such as dichloromethane at an elevated temperature for example under reflux.

The cyclisation of the compound of formula (VII) can be advantageously effected under Williamson conditions using a base such as cesium carbonate in a solvent such as N,N-dimethylformamide at an elevated temperature such as 90° C. Other conditions that can be used for the cyclisation of the compound of formula (VII) can be for example by treatment with O-(benzotriazol-1-yl)-N,N,N',N'-tetramethyluronium hexafluorophosphate (HBTU) and N,N-diisopropylethylamine in a solvent such as N,N-dimethylformamide at for example room temperature.

The resulting compound of formula (VII) can optionally be treated to form a compound of formula (I).

Compounds H85, H87, H98 and H99 may be prepared according to the synthesis described in Scheme 2.

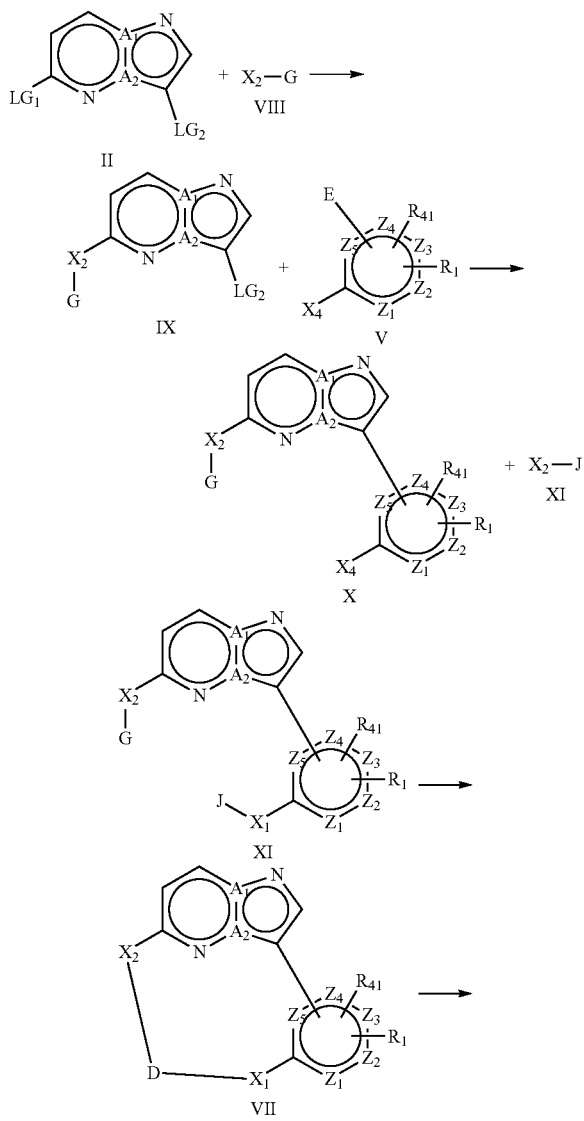

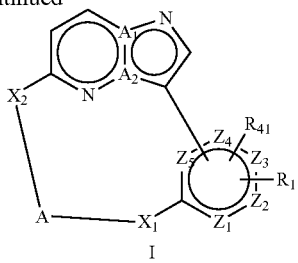

In the above reaction of the compound of formula (II) with the compound of formula (VIII) the leaving groups $LG_1$ and $LG_2$ are advantageously a halo group such as a chlorine or a bromine group. The reaction can be affected by a substitution for example by treating the compound of formula (II) with the compound of formula (VIII) in an organic solvent such as acetonitrile with an appropriate base such as for example diisopropylethylamine at an elevated temperature for example under reflux.

Compounds of formula (VIII) and (XI) can be either commercially acquired or obtained through various selective protection and deprotection steps.

The resulting compound of formula (IX) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofuran at an elevated temperature such as under reflux.

The reaction of the resulting compound (IX) with a (hetero-)aryl compound of formula (V) is advantageously effected through the coupling of a boronic acid E or boronic ester E derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example 80° C.

The reaction of the resulting compound of formula (X) with a compound of formula (XI) which can be advantageously effected under Williamson conditions using a base such as potassium carbonate in a solvent such as acetonitrile at an elevated temperature such as under reflux. This reaction can also be effected under Mitsunobu conditions using for example diisopropyl azodicarboxylate and triphenylphosphine in a solvent such as tetrahydrofuran at an elevated temperature such as 90° C.

The resulting compound of formula (XI) can optionally be treated to remove any desired protecting groups for example tert-butyloxycarbonylamino groups can be converted to the parent free amino group and for example ester groups can be converted to the parent free carboxylic acid groups. Such deprotection can be effected in a conventional manner for example by treatment under acidic conditions for example using an aqueous 6N hydrochloric acid solution in a solvent such as acetonitrile at an elevated temperature for example 60° C. or using an acid such as trifluoroacetic acid in a solvent such as dichloromethane at for example room temperature.

The cyclisation of the compound of formula (XI) can be effected for example by treatment with O-(benzotriazol-1-yl)-N,N,N',N'-tetramethyluronium hexafluorophosphate (HBTU) and N,N-diisopropylethylamine in a solvent such as N,N-dimethylformamide at for example room temperature.

The resulting compound of formula (VII) can optionally be treated to form a compound of formula (I).

Compound H89 may be prepared according to the synthesis described in Scheme 3.

The above general processes are illustrated by the specific processes which are described in the patent applications WO2013/045653 A1 and WO2013/046029 A1.

Example H78

Example H78 is prepared following general scheme 1.
Preparation of Intermediate 1

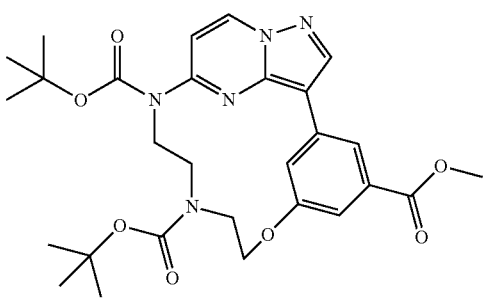 [SMILES: COC(=O)c1cc2cc(c1)-c1cnn3ccc(nc13)N(C(=O)OC(C)(C)C)CCN(C(=O)OC(C)(C)C)CCO2]

Intermediate 1 is prepared according to similar procedures that have been applied to obtain 10,13-di-tert-butyl 7-oxa-10,13,17,18,21-pentaazatetracyclo[12.5.2.1^{2,6}.0^{17,20}]docosa-1(20),2(22),3,5,14(21),15,18-heptaene-10,13-dicarboxylate described in the patent application WO2013/046029 A1, except that (3-hydroxy-5-methoxycarbonyl-phenyl)boronic acid was used for the Suzuki coupling. The ring closure was effected according to following procedure. A solution of methyl 3-[5-[tert-butoxycarbonyl-[2-(tert-butoxycarbonyl(2-hydroxyethyl)amino)ethyl]amino]pyrazolo[1,5-a]pyrimidin-3-yl]-5-hydroxy-benzoate (8.946 g, 15.65 mmol) in 2-methyltetrahydrofuran (20 ml/mmol) and a solution of diisopropyl azodicarboxylate (9.31 ml, 46.95 mmol) in toluene (20 ml/mmol) were added simultaneously over a period of 3 hours to a solution of triphenylphosphine (12.315 g, 46.95 mmol) in toluene (75 ml/mmol) at 90° C. The mixture was stirred at 90° C. for 30 minutes. The reaction mixture was cooled and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 7.698 mg of intermediate 1 (89%)
LCMS method 1: MH$^+$=554, RT=1.470 min
Preparation of Intermediate 2

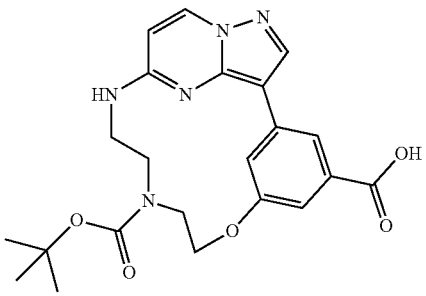 [SMILES: CC(C)(C)OC(=O)N1CCNc2ccn3ncc(c3n2)-c2cc(cc(C(=O)O)c2)OCC1]

Intermediate 1 (2.00 g, 3.61 mmol) and lithium hydroxide monohydrate (450 mg, 10.83 mmol) in a mixture tetrahydrofuran/methanol/water (2:2:1, 40 ml) were stirred at 50° C. for 15 hours. The solvent was removed under reduced pressure. Water was added and 1N HCl was added to acidify the solution to pH 5-6. The precipitate was filtered, washed with methanol and dried under reduced pressure. The residue was used in the next step without further purification.

LCMS method 2: MH$^+$=440, RT=0.860 min
Preparation of Intermediate 3

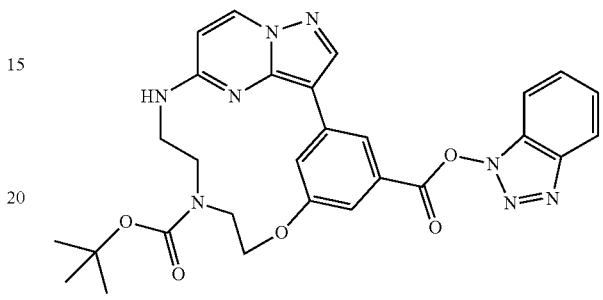

1-Hydroxybenzotriazole (600 mg, 3.84 mmol) was added to a solution of intermediate 2 (1.123 g, 2.56 mmol) in dry tetrahydrofurane (7.68 ml). N,N'-diisopropylmethanediimine (598 µl, 3.84 mmol) was added and the reaction mixture was stirred at room temperature for 3 hours. Water was added and the aqueous layer was extracted with ethyl acetate. The organic layer was dried, filtered and the solvent was removed under reduced pressure. The solvent was removed under reduced pressure and the product was without further purification used in the next step.

LCMS method 2: MH$^+$=557, RT=1.190 min
Preparation of Intermediate 4

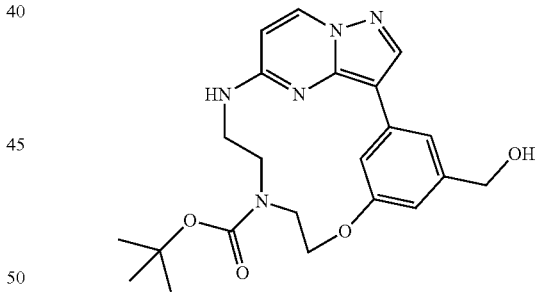

Sodium borohydride (100 mg, 2.56 mmol) was added at 0° C. to a suspension of intermediate 3 (1.42 g, 2.56 mmol) in dry tetrahydrofuran (7.68 ml). The mixture was stirred at room temperature for 3 hours. More sodium borohydride (20 mg, 0.512 mmol) was added and the mixture was stirred at room temperature for 1 more hour. Water was added and the product was extracted with ethyl acetate. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

Yield: 357 mg of intermediate 4 (33%)
LCMS method 1: MH$^+$=426, RT=0.792 min

Preparation of Intermediate 5

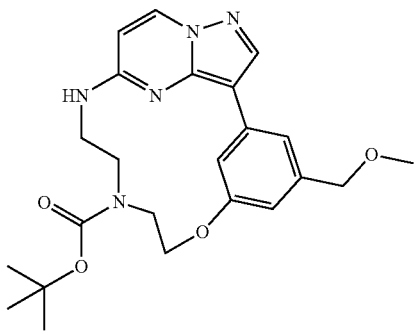 [SMILES: COCc1cc2cc(c1)-c1cnn3ccc(nc13)NCCN(C(=O)OC(C)(C)C)CCO2]

To a solution of intermediate 4 (500 mg, 1.18 mmol) in dry N,N-dimethylformamide (3.5 ml) was added sodium hydride (60% in mineral oil, 30 mg, 1.30 mmol) and methyl iodide (88 µl, 1.42 mmol). The mixture was stirred at room temperature for 15 hours. More sodium hydride (60% in mineral oil, 10 mg, 0.43 mmol) and methyl iodide (30 µl, 0.47 mmol) were added and the mixture was stirred at room temperature for 4 hours. Water was added to the reaction mixture and the product was extracted with ethyl acetate. The organic layer was dried, filtered and the solvent was removed under reduced pressure. The residue was purified by flash column chromatography over silica gel using dichloromethane and methanol as eluents (gradient elution from 0% to 5% methanol). The product fractions were collected and the solvent was and the solvent was removed under reduced pressure.

Yield: 274 mg of intermediate 5 (53%)

LCMS method 1: MH$^+$=440, RT=0.882 min

Preparation of Example H78

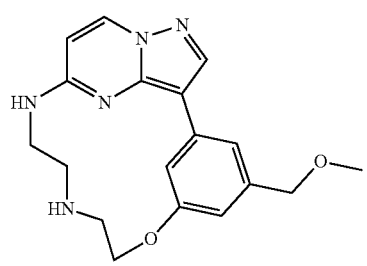 [SMILES: COCc1cc2cc(c1)-c1cnn3ccc(nc13)NCCNCCO2]

Intermediate 5 (274 mg, 0.62 mmol) was stirred in 4N HCl in 1,4-dioxane (1.9 ml) at room temperature for 3 hours. The solvent was removed under reduced pressure. Toluene was added and removed under reduced pressure. The product was obtained as HCl salt.

LCMS method 2: MH$^+$=340, RT=1.485 min

Example H79

Example H79 is prepared following general scheme 1.

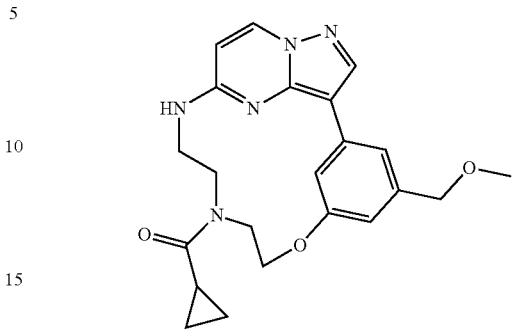

Example H78 (184 mg, 0.49 mmol) and triethylamine (204 µl, 1.47 mmol) were stirred in dry tetrahydrofuran (1.5 ml). Cyclopropanecarbonyl chloride (40 µl, 0.49 mmol) was added and the mixture was stirred at room temperature for 2 hours. The solvent was removed under reduced pressure. Methanol was added and the solid was filtered. The product was purified by reversed phase HPLC (HPLC method A). The product fractions were collected and the solvent was evaporated.

Yield: 143 mg of example H79 (72%)

LCMS method 2: MH$^+$=408, RT=2.624 min

Example H80

Example H80 is prepared following general scheme 1.

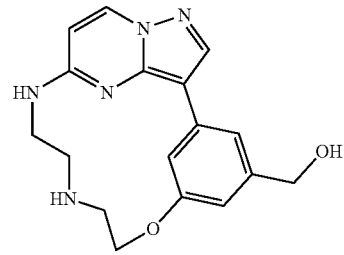 [SMILES: OCc1cc2cc(c1)-c1cnn3ccc(nc13)NCCNCCO2]

Intermediate 4 (482 mg, 1.13 mmol) was stirred in 4N HCl in 1,4-dioxane (3.4 ml) at room temperature for 3 hours. The solvent was removed under reduced pressure. Toluene was added and removed under reduced pressure. The product was obtained as HCl salt.

LCMS method 2: MH$^+$=326, RT=1.391 min

Example H81

Example H80 can be prepared following general scheme 1.

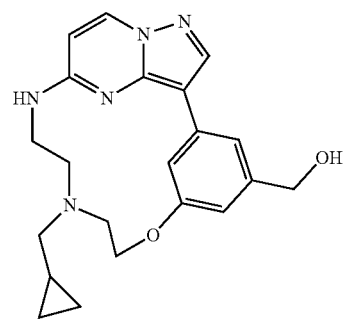 [SMILES: OCc1cc2cc(c1)-c1cnn3ccc(nc13)NCCN(CC1CC1)CCO2]

Example B64 (78 mg, 0.198 mmol) was added to borane tetrahydrofuran complex (1M solution in tetrahydrofuran, 4 ml) at 0° C. The suspension was stirred at room temperature for 17 hours. The solvent was removed under reduced pressure. A 2 N HCl solution (4.4 ml) was added and the reaction mixture was refluxed for 1 hour. The pH of the solution was adjusted with 1 N sodium hydroxide to pH 7 and the solvent was removed under reduced pressure. The product was purified by reversed phase HPLC (HPLC method A). The product fractions were collected and the solvent was evaporated.

Yield: 10 mg of example H81 (13%)
LCMS method 2: MH⁺=380, RT=1.671 min

Example H82

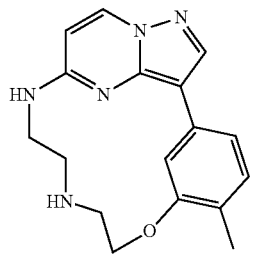 [SMILES: Cc1ccc2cc1OCCNCCNc1ccn3ncc-2c3n1]

Example H82 can be prepared following general scheme 1 and according to the procedures described in the patent application WO2013/045653 A1 to obtain example 17.

Example H83

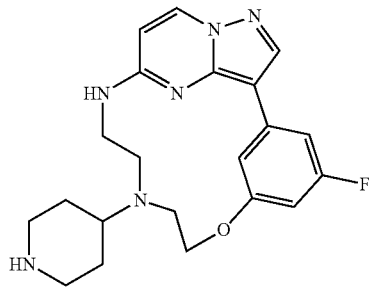 [SMILES: Fc1cc2cc(c1)-c1cnn3ccc(nc13)NCCN(C1CCNCC1)CCO2]

Example H83 can be prepared following general scheme 1 and according to the procedures described in the patent application WO2013/045653 A1 to obtain example 5.

Example H84

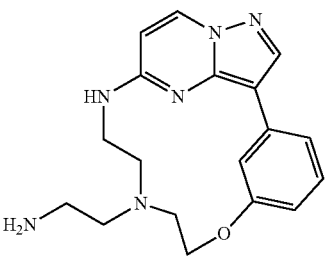 [SMILES: NCCN1CCNc2ccn3ncc(c3n2)-c2cccc(c2)OCC1]

Example H84 can be prepared following general scheme 1 and according to the procedures described in the patent application WO2013/045653 A1 to obtain example 5.

Example H85

Example H85 is prepared following general scheme 2.
Preparation of Intermediate 6

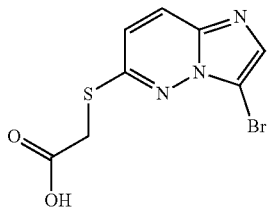 [SMILES: O=C(O)CSc1ccc2ncc(Br)n2n1]

A mixture of 3-bromo-6-chloro-imidazo[2,1-f]pyridazine (3.0 g, 12.9 mmol), 2-sulfanylacetic acid (11.88 g, 129 mmol) and N,N-diisopropylethylamine (6.741 ml, 38.7 mmol) in n-butanol (38.7 ml) was stirred at 150° C. overnight. The reaction mixture was cooled and water was added. The aqueous layer was extracted with n-butanol. The combined organic layers were dried, filtered and the solvent was removed under reduced pressure. The residue was purified by flash column chromatography over silica gel using dichloromethane and methanol as eluents (gradient elution from 0% to 10% of methanol). The product fractions were collected and the solvent was evaporated.

Yield: 3.06 g of intermediate 6 (38%)
LCMS method 2: MH⁺=288, RT=1.856 min
Preparation of Intermediate 7

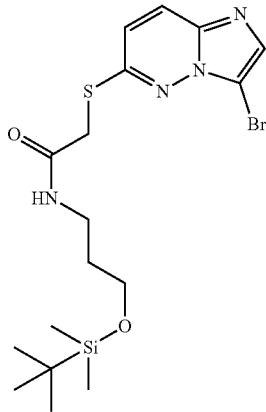 [SMILES: CC(C)(C)[Si](C)(C)OCCCNC(=O)CSc1ccc2ncc(Br)n2n1]

To a solution of intermediate 6 (5.32 mmol) in N,N-dimethylformamide (16 ml) was added 3-(tert-butyl(dimethyl)silyl)oxypropan-1-amine (1.11 g, 5.85 mmol), O-(benzotriazol-1-yl)-N,N,N',N'-tetramethyluronium hexafluorophosphate (HBTU) (2.73 g, 20.22 mmol) and N,N'-diisopropylmethanediimine (3.4 ml, 21.81 mmol). The reaction mixture was stirred at room temperature for 3 hours. The solvent was removed under reduced pressure. The residue was dissolved in ethyl acetate and washed with water and an aqueous saturated sodium bicarbonate solution. The organic layer was dried, filtered and the solvent was removed under reduced pressure. The residue was purified by flash column chromatography over silica gel using dichloromethane and methanol as eluents (gradient elution from 0% to 5% of methanol). The product fractions were collected and the solvent was evaporated.

Yield: 1.75 g of intermediate 7 (72%)
LCMS method 1: MH+=459, RT=1.062 min

Preparation of Intermediate 8

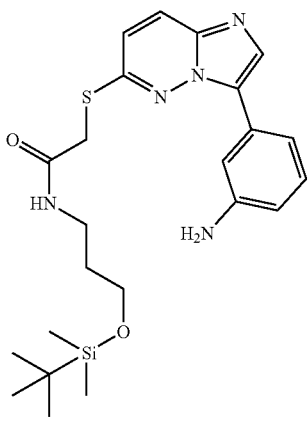 [SMILES: CC(C)(C)[Si](C)(C)OCCCNC(=O)CSc1ccc2ncc(-c3cccc(N)c3)n2n1]

A mixture of 1,4-dioxane and water (3:1, 37.5 ml) was degassed by bubbling nitrogen gas through the mixture. Intermediate 7 (2.87 g, 6.25 mmol), (3-aminophenyl)boronic acid (1.45 g, 9.38 mmol), tetrakis(triphenylphosphine)palladium(0) (580 mg, 0.50 mmol), 2-dicyclohexylphosphino-2',4',6'-triisopropylbiphenyl (Xphos) (477 mg, 1.00 mmol) and potassium phosphate tribasic (6.63 g, 5 eq.) were added and the mixture was stirred under nitrogen gas at 90° C. overnight. The reaction mixture was cooled, diluted with ethyl acetate and the organic layer was washed with water and brine. The organic layer was dried, filtered and the solvent was removed under reduced pressure. The residue was purified by flash column chromatography over silica gel using heptane and ethyl acetate as eluents (gradient elution from 20% to 100% of ethyl acetate). The product fractions were collected and the solvent was removed under reduced pressure.

Yield: 1.67 g of intermediate 8 (57%)
LCMS method 2: MH+=472, RT=3.424 min

Preparation of Intermediate 9

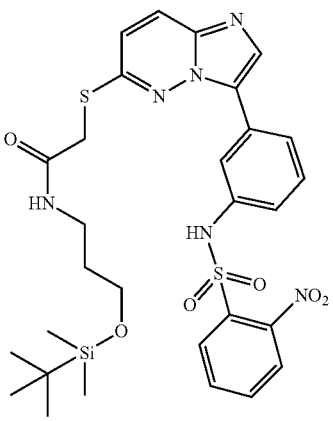 [SMILES: CC(C)(C)[Si](C)(C)OCCCNC(=O)CSc1ccc2ncc(-c3cccc(NS(=O)(=O)c4ccccc4[N+](=O)[O-])c3)n2n1]

2-Nitrobenzenesulfonyl chloride (830 mg, 3.75 mmol) was added portion wise to a stirred solution of intermediate 8 (1.61 g, 3.41 mmol) and triethylamine (567 μl, 4.09 mmol) in dichloromethane (10.2 ml). The reaction mixture was stirred at room overnight. The reaction mixture was diluted with dichloromethane and washed with water and brine. The organic layer was dried, filtered and the solvent was removed under reduced pressure. The residue was purified by flash column chromatography over silica gel using heptane and ethyl acetate as eluents (gradient elution from 30% to 100% of ethyl acetate). The product fractions were collected and the solvent was removed under reduced pressure.

Yield: 1.59 g of intermediate 9 (71%)
LCMS method 2: MH+=657, RT=4.280 min

Preparation of Intermediate 10

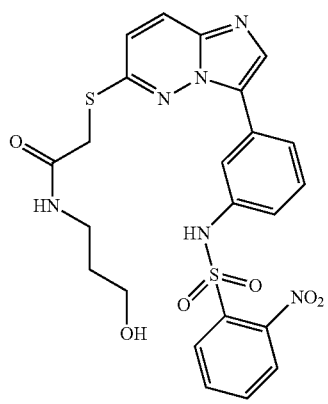 [SMILES: O=C(CSc1ccc2ncc(-c3cccc(NS(=O)(=O)c4ccccc4[N+](=O)[O-])c3)n2n1)NCCCO]

A mixture of tetrabutylammonium fluoride (891 mg, 3.41 mmol) and intermediate 9 (1.49 g, 2.27 mmol) in tetrahydrofuran (6.81 ml) was stirred at room temperature overnight. The solvent was removed under reduced pressure and the residue was dissolved in ethyl acetate. The organic layer was washed with water and brine. The organic layer was dried, filtered and the solvent was removed under reduced pressure. The residue was purified by flash column chromatography over silica gel using dichloromethane and methanol as eluents (gradient elution from 0% to 10% of methanol). The product fractions were collected and the solvent was removed under reduced pressure.

Yield: 630 mg of intermediate 10 (51%)
LCMS method 2: MH+=543, RT=2.581 min

Preparation of Intermediate 11

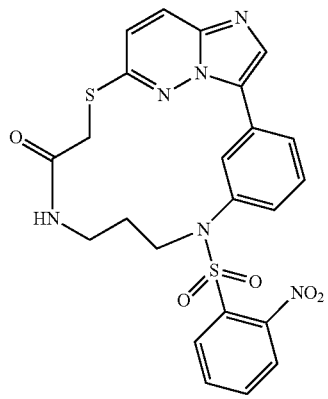 [SMILES: O=C1CSc2ccc3ncc(n3n2)-c2cccc(c2)N(S(=O)(=O)c2ccccc2[N+](=O)[O-])CCCN1]

A solution of intermediate 10 (380 mg, 0.70 mmol) in 2-methyltetrahydrofuran (20 ml/mmol) and N,N-dimethylacetamide (2 ml) was degassed by bubbling nitrogen gas through the mixture. A solution of diisopropyl azodicarboxylate (420 mg, 2.10 mmol) in toluene (20 ml/mmol) was degassed by bubbling nitrogen gas through the mixture. Both solutions were added drop wise and simultaneously over a period of 30 minutes at 90° C. to a degassed solution of triphenylphosphine (551 mg, 2.10 mmol) in toluene (75 ml/mmol). The mixture was stirred at 90° C. for 1 hour. The reaction mixture was cooled and the solvent was removed under reduced pressure. The residue was purified by flash column chromatography over silica gel using using dichloromethane and methanol as eluents (gradient elution from 0% to 5% of methanol). The product fractions were collected and the solvent was removed under reduced pressure.

Yield: 244 mg of intermediate 11 (66%)
LCMS method 2: MH$^+$=525, RT=2.769 min

Preparation of Intermediate 12

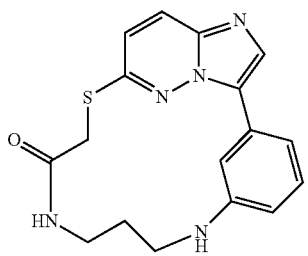 [SMILES: O=C1CSc2ccc3ncc(n3n2)-c2cccc(c2)NCCCN1]

Intermediate 11 (337 g, 0.64 mmol) and cesium carbonate (313 mg, 0.96 mmol) were suspended in N,N-dimethylformamide (1.9 ml). Thiophenol (70 µl, 0.70 mmol) was added and the mixture was stirred at room temperature for 4 hours. The solvent was removed under reduced pressure. The residue was purified by flash column chromatography over silica gel using using heptane and ethyl acetate as eluents (gradient elution from 30% to 80% of ethyl acetate). The product fractions were collected and the solvent was removed under reduced pressure.

Yield: 174 mg of intermediate 12 (80%)
LCMS method 2: MH$^+$=340, RT=1.488 min

Preparation of Example H85

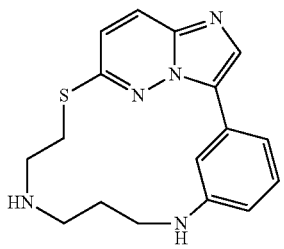 [SMILES: c1cc2cc(c1)-c1cnc3ccc(nn13)SCCNCCCN2]

A mixture of intermediate 12 (20 mg, 0.06 mmol) and 1N borane tetrahydrofuran complex solution in tetrahydrofuran (0.18 ml) was stirred at room temperature overnight. The solvent was removed under reduced pressure and an aqueous concentrated hydrochloric acid solution was added. The reaction mixture was refluxed for 1 hour. The reaction mixture was neutralized to pH 7 with a 2N aqueous sodium hydroxide solution and the solvent was removed under reduced pressure. The residue was purified by reversed phase column chromatography (HPLC method A).

Yield: 4 mg of example H85 (20%)
LCMS method 2: MH$^+$=326, RT=1.513 min

Example H86

Example H86 is prepared following general scheme 1.
Preparation of Intermediate 13

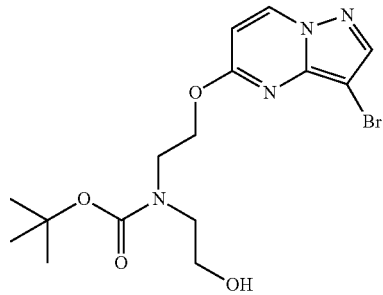 [SMILES: CC(C)(C)OC(=O)N(CCO)CCOc1ccn2ncc(Br)c2n1]

A mixture of tert-butyl N,N-bis(2-hydroxyethyl)carbamate (52.98 g, 258.10 mmol) and sodium hydride (60% in mineral oil, 1.548 g, 64.52 mmol) in anhydrous tetrahydrofuran (129 ml) was stirred at room temperature for 30 minutes. 3-Bromo-5-chloro-pyrazolo[1,5-a]pyrimidine (10.00 g, 43.02 mmol) was added and the reaction mixture was stirred at room temperature for 2 hours. More sodium hydride (60% in mineral oil, 0.25 eq.) was added and the reaction mixture was stirred at room temperature for 1 hour. Water was added and the tetrahydrofuran was removed under reduced reduced pressure. The residue was diluted with ethyl acetate and washed with water and brine. The organic layer was dried, filtered and the solvent was removed under reduced pressure. The residue was purified by flash column chromatography over silica gel using heptane and ethyl acetate as eluents (gradient elution from 0% to 75% of ethyl acetate). The product fractions were collected and the solvent was removed under reduced pressure.

Yield: 17.056 g of intermediate 13 (99%)
LCMS method 1: MH$^+$=423 (MH$^+$+Na, RT=0.779 min Preparation of Intermediate 14

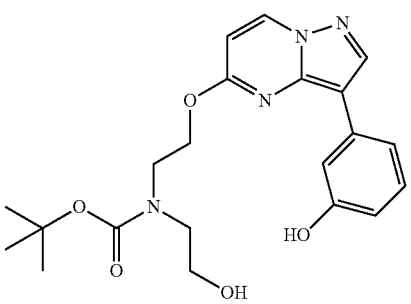 [SMILES: CC(C)(C)OC(=O)N(CCO)CCOc1ccn2ncc(-c3cccc(O)c3)c2n1]

A mixture of 1,4-dioxane and water (3:1, 96.6 ml) was degassed by bubbling nitrogen gas through the mixture. Intermediate 13 (12.916 g, 32.189 mmol), (3-hydroxyphenyl)boronic acid (5.328 g, 38.63 mmol), tris(dibenzylideneacetone)dipalladium(0) (742 mg, 0.64 mmol) 2-dicyclohexylphosphino-2',4',6'-triisopropylbiphenyl (Xphos) (1.23 g, 2.58 mmol) and potassium phosphate tribasic (34.163 g, 5 eq.) were added and the mixture was stirred under nitrogen gas at 80° C. for 15 hours. The reaction mixture was cooled and the solvent was removed under reduced pressure. Water was added and the product was extracted with ethyl acetate. The combined organic layers were dried, filtered and the solvent was removed under reduced pressure. The residue was purified by flash column chromatography over silica gel using using dichloromethane and methanol as eluents (gradient elution from 0% to 10% of methanol). The product fractions were collected and the solvent was removed under reduced pressure.

Yield: 10.353 g of intermediate 14 (78%)
LCMS method 2: MH$^+$=415, RT=0.744 min Preparation of Intermediate 15

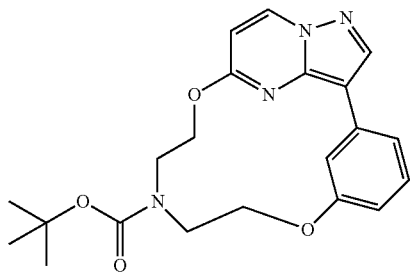 [SMILES: CC(C)(C)OC(=O)N1CCOc2cccc(c2)-c2cnn3ccc(nc23)OCC1]

A solution of intermediate 14 (500 mg, 1.21 mmol) in 2-methyltetrahydrofuran (20 ml/mmol) was degassed by bubbling nitrogen gas through the mixture. A solution of diisopropyl azodicarboxylate (7300 mg, 3.63 mmol) in toluene (20 ml/mmol) was degassed by bubbling nitrogen gas through the mixture. Both solutions were added drop wise and simultaneously over a period of 1.5 hours at 90° C. to a degassed solution of triphenylphosphine (952 mg, 3.63 mmol) in toluene (75 ml/mmol). The mixture was stirred at 90° C. for 1.5 hours. The reaction mixture was cooled and the solvent was removed under reduced pressure. Water was added and the product was extracted with dichloromethane. The combined organic layers were dried, filtered and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure. The residue was purified by reversed phase column chromatography (HPLC method A).

Yield: 209 mg of intermediate 15 (44%)
LCMS method 1: MH$^+$=397, RT=1.131 min

Preparation of Intermediate 16

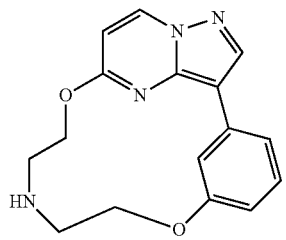 [SMILES: c1cc2cc(c1)-c1cnn3ccc(nc13)OCCNCCO2]

Intermediate 15 (209 mg, 0.53 mmol) was stirred in 4N HCl in 1,4-dioxane (1.59 ml) at 45° C. for 5 hours. The solvent was removed under reduced pressure. Toluene was added twice and removed twice under reduced pressure. The product was obtained as HCl salt and was without any further purification used in the next step.

LCMS method 1: MH$^+$=297, RT=0.319 min

Preparation of Intermediate 17

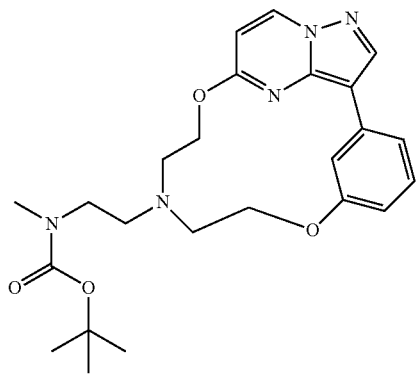 [SMILES: CN(CCN1CCOc2cccc(c2)-c2cnn3ccc(nc23)OCC1)C(=O)OC(C)(C)C]

Intermediate 16 (0.26 mmol) and triethylamine (108 μl, 0.78 mmol) were dissolved in a mixture of dichloromethane and methanol (1:1, 2.1 ml). Tert-butyl N-methyl-N-(2-oxoethyl)carbamate (90 μl, 0.52 mmol) was added and the mixture stirred at room temperature for 30 minutes. Sodium triacetoxyborohydride (121 mg, 0.57 mmol) was added portion wise and the mixture was stirred at room temperature for 18 hours. More tert-butyl N-methyl-N-(2-oxoethyl) carbamate (0.4 eq.) and sodium triacetoxyborohydride (0.4 eq) were added and the reaction mixture was stirred at room temperature for 6 hours. The solvent was removed under reduced pressure. Dichloromethane was added and the organic layer was washed with water. The organic layer was dried, filtered and the solvent was removed under reduced pressure. The residue was purified by flash column chromatography over silica gel using heptane and ethyl acetate as eluents (gradient elution from 0% to 67% of ethyl acetate). The product fractions were collected and the solvent was removed under reduced pressure.

Yield: 70 mg of intermediate 17 (59%)
LCMS method 2: MH$^+$=454, RT=3.622 min

Preparation of Example H86

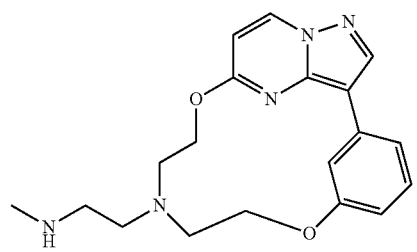 [SMILES: CNCCN1CCOc2cccc(c2)-c2cnn3ccc(nc23)OCC1]

Intermediate 17 (70 mg, 0.15 mmol) was stirred in a 4N solution of HCl in 1,4-dioxane (1 ml). The mixture was stirred at room temperature for 3 hours. The solvent was removed under reduced pressure. Methanol was added. The solid was filtered, washed with diisopropyl ether and dried under reduced pressure. The product is obtained as the HCl salt.

Yield: 41 mg of example H86 (70%)
LCMS method 2: MH$^+$=354, RT=2.260 min

Example H87

Example H87 is prepared following general scheme 2.
Preparation of Intermediate 18

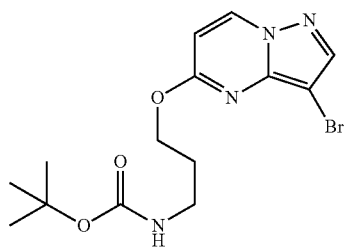 [SMILES: CC(C)(C)OC(=O)NCCCOc1ccn2ncc(Br)c2n1]

Sodium hydride (60% in mineral oil, 620 mg, 25.82 mmol) and Tert-butyl N-(2-hydroxypropyl)carbamate (12.063 g, 68.84 mmol) were dissolved in dry tetrahydrofuran (51.6 ml) and stirred at room temperature for 30 minutes. 3-Bromo-5-chloro-pyrazolo[1,5-a]pyrimidine (4.0 g, 17.21 mmol) was added portion wise and the mixture was stirred at room temperature for 2 hours. Water was added and the solvent was removed under reduced pressure. The residue was diluted with dichloromethane and washed with water. The organic layer was dried, filtered and the solvent was removed under reduced pressure. The residue was purified by flash column chromatography over silica gel using heptane and ethyl acetate as eluents (gradient elution from 0% to 30% ethyl acetate). The product fractions were collected and the solvent was removed under reduced pressure.

Yield: 4.80 g of intermediate 18 (75%)
LCMS method 1: MH$^+$=393, RT=0.906 min

Preparation of Intermediate 19

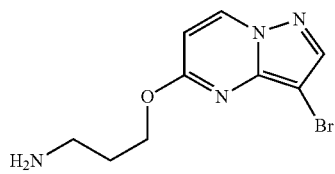

Intermediate 18 (4.80 g, 12.93 mmol) was stirred in 4N HCl in methanol (38.8 ml) at room temperature for 4 hours. The solid was filtered, washed with diisopropylether and dried under reduced pressure. The product was obtained as HCl salt and was without any further purification used in the next step.

Yield: 3.90 g of intermediate 19 (98%)
LCMS method 1: MH$^+$=271, RT=0.213 min

Preparation of Intermediate 20

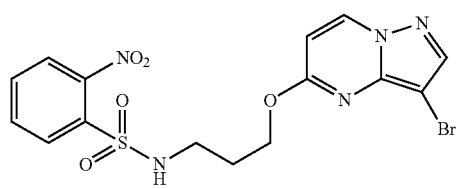 [SMILES: O=[N+]([O-])c1ccccc1S(=O)(=O)NCCCOc1ccn2ncc(Br)c2n1]

Intermediate 19 (3.90 g, 12.68 mmol) and triethylamine (5.202 ml, 38.04 mmol) were dissolved in dichloromethane (38 ml). 2-Nitrobenzenesulfonyl chloride (3.934 g, 17.75 mmol) was added and the reaction mixture was stirred at room for 18 hours. The reaction mixture was diluted with dichloromethane and washed with an aqueous 1N hydrochloric acid solution and an aqueous 1N sodium bicarbonate solution. The organic layer was dried, filtered and the solvent was removed under reduced pressure. The residue was purified by flash column chromatography over silica gel using heptane and ethyl acetate as eluents (gradient elution from 20% to 100% of ethyl acetate). The product fractions were collected and the solvent was removed under reduced pressure.

Yield: 4.10 g of intermediate 20 (71%)
LCMS method 1: MH$^+$=458, RT=0.820 min

Preparation of Intermediate 21

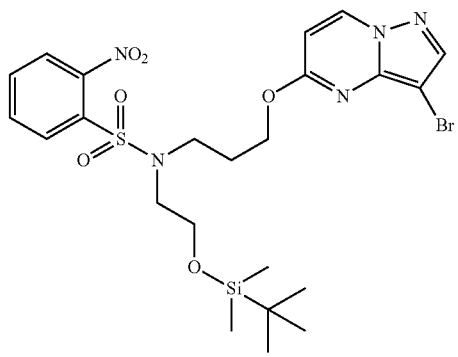 [SMILES: CC(C)(C)[Si](C)(C)OCCN(CCCOc1ccn2ncc(Br)c2n1)S(=O)(=O)c1ccccc1[N+](=O)[O-]]

A mixture of intermediate 20 (5.10 g, 11.18 mmol), cesium carbonate (7.267 g, 22.36 mmol) and 2-bromoethoxy-tert-butyl-dimethyl-silane (2.87 ml, 13.42 mmol) in N,N-dimethylformamide (33.5 ml) was stirred at 50° C. for 3 hours. The reaction mixture was cooled, water was added and the product was extracted with ethyl acetate. The organic layer was washed with water and brine, dried, filtered and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure.

Yield: 6.00 g of intermediate 21 (87%)
LCMS method 1: MH$^+$=616, RT=1.364 min

Preparation of Intermediate 22

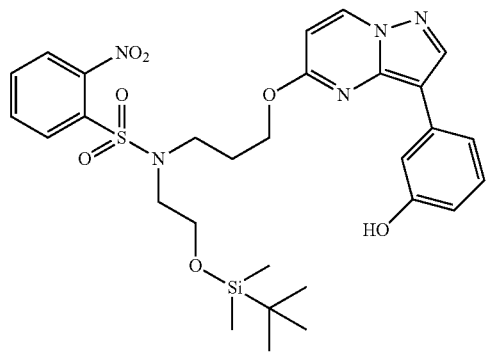 [SMILES: CC(C)(C)[Si](C)(C)OCCN(CCCOc1ccn2ncc(-c3cccc(O)c3)c2n1)S(=O)(=O)c1ccccc1[N+](=O)[O-]]

Intermediate 21 (2.0 g, 3.25 mmol), (3-hydroxyphenyl)boronic acid (540 mg, 3.90 mmol), 2-dicyclohexylphosphino-2',4',6'-triisopropylbiphenyl (Xphos) (62 mg, 0.13 mmol) and potassium phosphate tribasic (6.215 g, 3 eq.) were dissolved in a mixture of 1,4-dioxane and water (3:1, 60 ml) and the mixture was degassed by bubbling nitrogen gas through the mixture. Tris(dibenzylideneacetone)dipalladium(0) (81 mg, 0.07 mmol) was added and the mixture was stirred under nitrogen gas at 80° C. for 7 hours. The reaction mixture was cooled and ethyl acetate was added. The organic layer was washed with water and brine, dried, filtered and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure.

Yield: 810 mg of intermediate 22 (40%)
LCMS method 1: MH$^+$=628, RT=1.281 min
Preparation of Intermediate 23

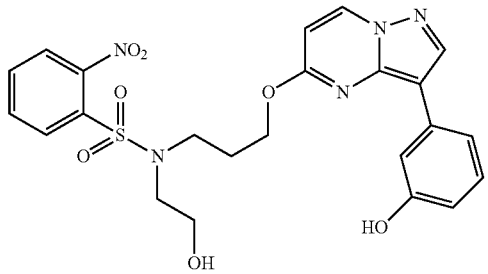 [SMILES: O=[N+]([O-])c1ccccc1S(=O)(=O)N(CCO)CCCOc1ccn2ncc(-c3cccc(O)c3)c2n1]

A mixture of tetrabutylammonium fluoride (410 mg, 1.55 mmol) and intermediate 22 (810 mg, 1.29 mmol) in tetrahydrofuran (3.87 ml) was stirred at room temperature for 1 hour. The solvent was removed under reduced pressure and the residue was dissolved in ethyl acetate. The organic layer was washed with a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 4% of methanol). The product fractions were collected and the solvent was removed under reduced pressure.

Yield: 456 mg of intermediate 23 (69%)
LCMS method 1: MH$^+$=514, RT=0.710 min
Preparation of Intermediate 24

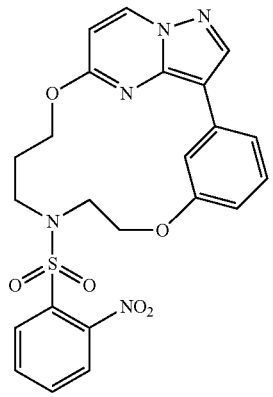 [SMILES: O=[N+]([O-])c1ccccc1S(=O)(=O)N1CCCOc2ccn3ncc(c3n2)-c2cccc(c2)OCC1]

A solution of intermediate 23 (456 mg, 0.89 mmol) in 2-methyltetrahydrofuran (20 ml/mmol) was degassed by bubbling nitrogen gas through the mixture. A solution of diisopropyl azodicarboxylate (540 mg, 2.67 mmol) in toluene (20 ml/mmol) was degassed by bubbling nitrogen gas through the mixture. Both solutions were added drop wise and simultaneously over a period of 2 hours at 90° C. to a degassed solution of triphenylphosphine (700 mg, 2.67 mmol) in toluene (75 ml/mmol). The mixture was stirred at 90° C. for 1 hour. The reaction mixture was cooled and the solvent was removed under reduced pressure. The residue was purified by flash column chromatography over silica gel using dichloromethane and methanol as eluents (gradient elution from 0% to 4% of ethyl methanol). The product fractions were collected and the solvent was removed under reduced pressure.

Yield: 310 mg of intermediate 24 (70%)
LCMS method 1: MH$^+$=496, RT=1.171 min

Preparation of Example H87

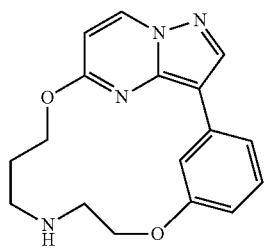 [SMILES: c1cc2cc(c1)-c1cnn3ccc(nc13)OCCCNCCO2]

Intermediate 24 (300 mg, 0.61 mmol) and cesium carbonate (397 mg, 1.22 mmol) were suspended in N,N-dimethylformamide (1.83 ml). Thiophenol (70 µl, 0.73 mmol) was added and the mixture was stirred at room temperature for 18 hours. Solid sodium hydroxide was added and the solvent was removed under reduced pressure. A mixture of dichloromethane and methanol (3:1) was added. The solid was filtered and washed with dichloromethane. The residue was purified by reversed phase column chromatography (HPLC method A).

Yield: 6 mg of example H87 (3%)
LCMS method 2: MH$^+$=311, RT=1.865 min

Example H88

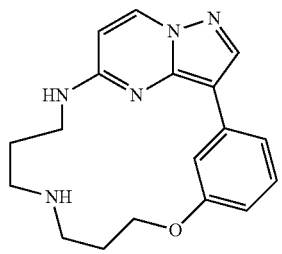 [SMILES: c1cc2cc(c1)-c1cnn3ccc(nc13)NCCCNCCCO2]

Example H88 is prepared following general scheme 1 and according to the procedures described in the patent application WO2013/045653 A1 to obtain example 18.

Example H89

Example H89 is prepared following general scheme 3.
Preparation of Intermediate 25

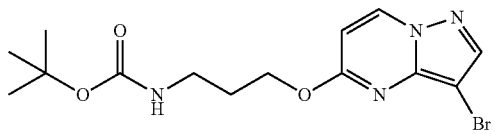 [SMILES: CC(C)(C)OC(=O)NCCCOc1ccn2ncc(Br)c2n1]

Sodium hydride (60% in mineral oil, 2.58 g, 64.53 mmol) and tert-butyl N-(3-hydroxypropyl)carbamate (30.15 g, 172.08 mmol) were dissolved in anhydrous tetrahydrofuran and stirred at room temperature for 30 minutes. 3-bromo- 5-chloro-pyrazolo[1,5-a]pyrimidine (10.00 g, 43.02 mmol) was added portion wise and the reaction mixture was stirred at room temperature for 1 hour. Water was added and the tetrahydrofuran was removed under reduced reduced pressure. The residue was diluted with dichloromethane and washed with water. The organic layer was dried, filtered and the solvent was removed under reduced pressure. The residue was purified by flash column chromatography over silica gel using heptane and ethyl acetate as eluents (gradient elution from 10% to 80% of ethyl acetate). The product fractions were collected and the solvent was removed under reduced pressure. The product was triturated with diethyl ether, filtered and dried under reduced pressure.

Yield: 14.06 g of intermediate 25 (88%)
LCMS method 2: MH$^+$=315, RT=3.401 min

Preparation of Intermediate 26

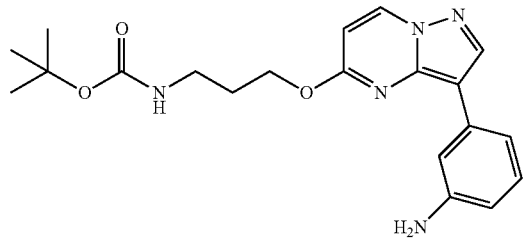 [SMILES: CC(C)(C)OC(=O)NCCCOc1ccn2ncc(-c3cccc(N)c3)c2n1]

A mixture of 1,4-dioxane and water (3:1, 65 ml) was degassed by bubbling nitrogen gas through the mixture. Intermediate G9 (4.00 g, 10.77 mmol), (3-aminophenyl) boronic acid (2.17 g, 14.00 mmol), tetrakis(triphenylphosphine)palladium(0) (255 mg, 0.22 mmol), 2-dicyclohexylphosphino-2',4',6'-triisopropylbiphenyl (Xphos) (205 mg, 0.43 mmol) and potassium phosphate tribasic (85 g, 3 eq.) were added and the mixture was stirred under nitrogen gas at 80° C. for 3 hours. The reaction mixture was cooled, diluted with ethyl acetate and the organic layer was washed with water and brine. The organic layer was dried, filtered and the solvent was removed under reduced pressure. The residue was purified by flash column chromatography over silica gel using heptane and ethyl acetate as eluents (gradient elution from 30% to 100% of ethyl acetate). The product fractions were collected and the solvent was removed under reduced pressure.

Yield: 3.12 g of intermediate 26 (76%)
LCMS method 1: MH$^+$=384, RT=1.012 min

Preparation of Intermediate 27

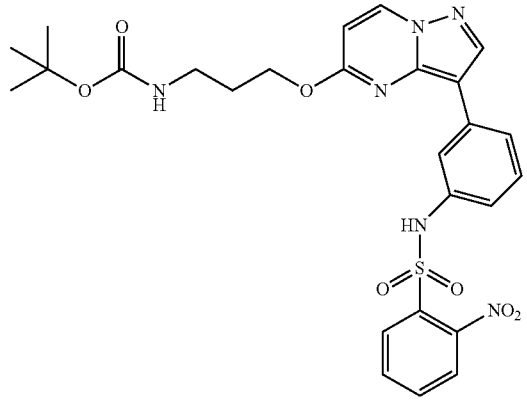 [SMILES: CC(C)(C)OC(=O)NCCCOc1ccn2ncc(-c3cccc(NS(=O)(=O)c4ccccc4[N+](=O)[O-])c3)c2n1]

2-Nitrobenzenesulfonyl chloride (3.38 g, 15.52 mmol) was added portion wise to a solution of intermediate G10 (3.90 g, 10.17 mmol) and triethylamine (4.24 ml, 30.51 mmol) in dichloromethane (42 ml). 4-Dimethylaminopyridine (62 mg, 0.51 mmol) was added and the reaction mixture was stirred at room for 18 hours. The reaction mixture was diluted with dichloromethane and washed with a saturated aqueous sodium bicarbonate solution and water. The organic layer was dried, filtered and the solvent was removed under reduced pressure. The residue was purified by flash column chromatography over silica gel using heptane and ethyl acetate as eluents (gradient elution from 0% to 40% of ethyl acetate). The product fractions were collected and the solvent was removed under reduced pressure.

Yield: 5.71 g of intermediate 27 (99%)

Preparation of Intermediate 28

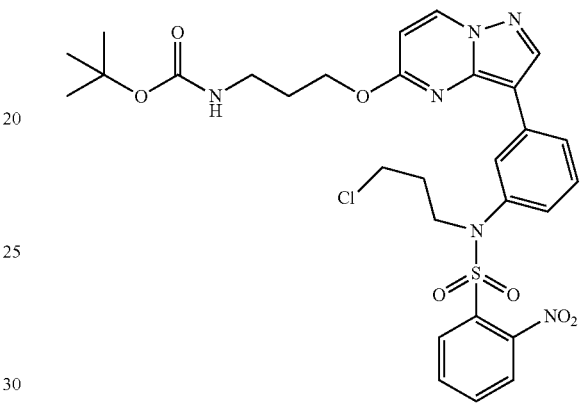

A mixture of intermediate 27 (4.3 g, 7.56 mmol) 1-bromo-3-chloro-propane (1.5 ml, 15.12 mmol) and cesium carbonate (6.158 g, 18.90 mmol) in N,N-dimethylformamide (22.7 ml) was stirred at 50° C. overnight. The reaction mixture was then stirred for 18 hours at 75° C. The mixture was cooled and ethyl acetate was added. The organic layer washed with water, dried, filtered and the solvent was removed under reduced pressure. The residue was purified by flash column chromatography over silica gel using dichloromethane and ethyl acetate as eluents. The product fractions were collected and the solvent was removed under reduced pressure.

Yield: 1.332 g of intermediate 28 (27%)
LCMS method 1: MH$^+$=545 (MH$^+$-Boc), RT=1.223 min Preparation of Intermediate 29

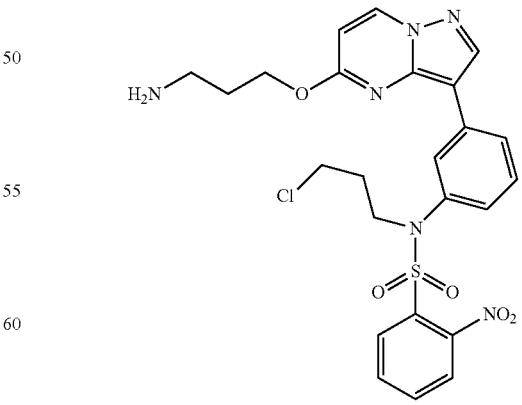

Intermediate 28 (1.95 g, 3.02 mmol) was dissolved in 4N hydrochloric acid in methanol (9.1 ml). The mixture was stirred at room temperature for overnight. The solvent was removed under reduced pressure. The residue was used in the next step without further purification.

Preparation of Intermediate 30

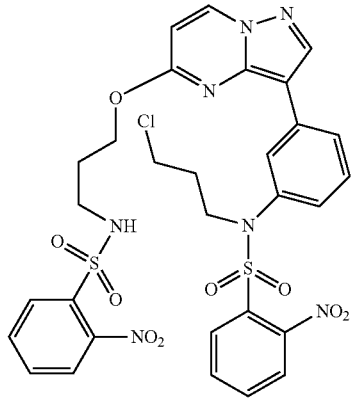 [SMILES: O=[N+]([O-])c1ccccc1S(=O)(=O)NCCCOc1ccn2ncc(-c3cccc(N(CCCCl)S(=O)(=O)c4ccccc4[N+](=O)[O-])c3)c2n1]

2-Nitrobenzenesulfonyl chloride (740 mg, 3.32 mmol) dissolved in N,N-dimethylacetamide (4.5 ml) was added drop wise at 0° C. to a solution of intermediate 29 (3.02 mmol) and triethylamine (2.099 ml, 15.10 mmol) in N,N-dimethylacetamide (4.5 ml). The reaction mixture was stirred at 0° C. for 1 hour. The crude mixture was diluted with ethyl acetate and washed with water. The organic layer was dried, filtered and the solvent was removed under reduced pressure. The residue was purified by flash column chromatography over silica gel using heptane and ethyl acetate as eluents. The product fractions were collected and the solvent was removed under reduced pressure.

Yield: 1.384 g of intermediate 30 (63%)

LCMS method 1: MH$^+$=731, RT=1.715 min

Preparation of Intermediate 31

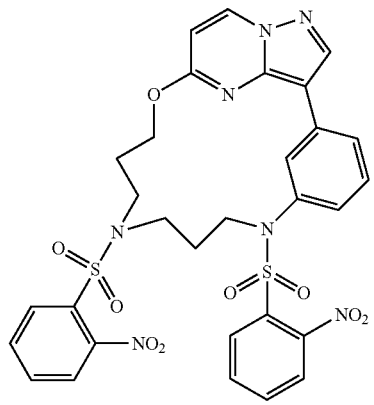 [SMILES: O=[N+]([O-])c1ccccc1S(=O)(=O)N1CCCOc2ccn3ncc(c3n2)-c2cccc(c2)N(S(=O)(=O)c2ccccc2[N+](=O)[O-])CCC1]

A solution of intermediate 30 (1.384 g, 1.90 mmol) in N,N-dimethylformamide (166 ml) was added drop wise over a period of 4 hours at 90° C. to a solution of cesium carbonate (3.09 g, 9.5 mmol) in N,N-dimethylformamide (56 ml). The reaction was stirred at 90° C. for 1 hour. The solvent was removed under reduced pressure. The residue was used in the next step without further purification.

Preparation of Intermediate 32

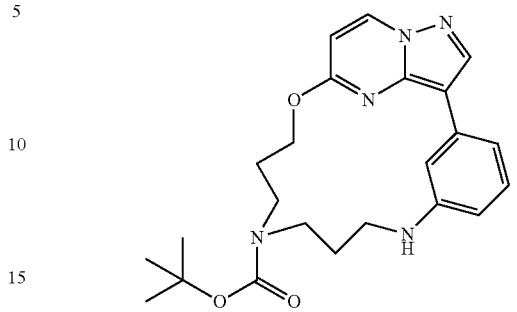

Intermediate 31 (1.90 mmol) and cesium carbonate (2.47 g, 7.66 mmol) were suspended in N,N-dimethylformamide (5.7 ml) and stirred at room temperature for 5 minutes. Thiophenol (430 µl, 4.18 mmol) was added and the mixture was stirred at room temperature for 2 hours. Tert-butoxycarbonyl anhydride (912 mg, 4.18 mmol) was added and the mixture was stirred at room temperature for 4 hours. An aqueous solution of 1N sodium hydroxide was added and the mixture was extracted with ethyl acetate. The organic layer was washed with water and brine. The organic layer was dried, filtered and the solvent was removed under reduced pressure. The residue was purified by flash column chromatography over silica gel using heptane and ethyl acetate as eluents. The product fractions were collected and the solvent was removed under reduced pressure.

Yield: 546 mg of intermediate 32 (68%)

LCMS method 2: MH$^+$=324 (MH$^+$-Boc), RT=1.866 min

Preparation of Example H89

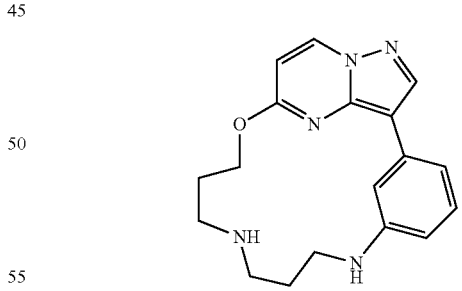

Intermediate 32 (546 mg, 1.29 mmol) was dissolved in 4N hydrochloric acid in methanol (3.87 ml). The mixture was stirred at room temperature for 1 hour. The solid was filtered, washed with diethyl ether and methanol. The product was dried under reduced pressure. The product was obtained as the HCl salt.

Yield: 386 mg of example H89 (83%)

LCMS method 2: MH$^+$=324, RT=1.867 min

Example H90

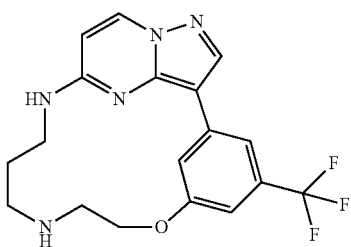 [SMILES: FC(F)(F)c1cc2cc(c1)-c1cnn3ccc(nc13)NCCCNCCO2]

Example H90 can be prepared following general scheme 1 and according to the procedures described in the patent application WO2013/045653 A1 to obtain example 18.

Example H91

Example H91 can be prepared following general scheme 1.

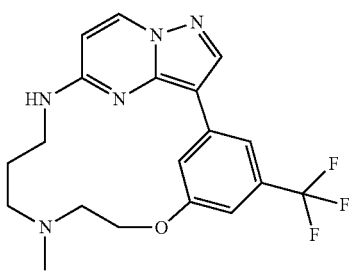 [SMILES: CN1CCCNc2ccn3ncc(c3n2)-c2cc(cc(C(F)(F)F)c2)OCC1]

Example H90 (62 mg, 0.16 mmol) and formaldehyde (14.6 μl, 0.18 mmol) were dissolved in methanol (0.48 ml) and stirred for 30 minutes at room temperature. Sodium triacetoxyborohydride (102 mg, 0.48 mmol) was added and the mixture was stirred at room temperature for 16 hours. An aqueous saturated sodium bicarbonate solution was added and the aqueous layer was extracted with ethyl acetate. The organic layer was dried, filtered and the solvent was removed under reduced pressure. The residue was purified by flash column chromatography over silica gel using dichloromethane and methanol as eluents (gradient elution from 0% to 5% of methanol). The product fractions were collected and the solvent was removed under reduced pressure.
Yield: 44 mg of example H91 (70%)
LCMS method 2: MH$^+$=302, RT=2.170 min

Example H92

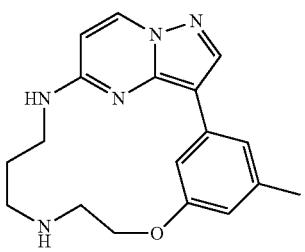 [SMILES: Cc1cc2cc(c1)-c1cnn3ccc(nc13)NCCCNCCO2]

Example H92 can be prepared following general scheme 1 and according to the procedures described in the patent application WO2013/045653 A1 to obtain example 18.

Example H93

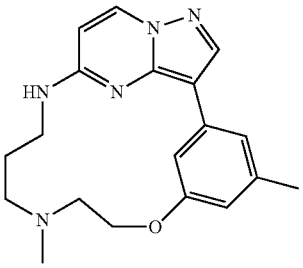 [SMILES: Cc1cc2cc(c1)-c1cnn3ccc(nc13)NCCCN(C)CCO2]

Example H93 can be prepared following general scheme 1 and according to the procedures described to obtain example H91.

Example H94

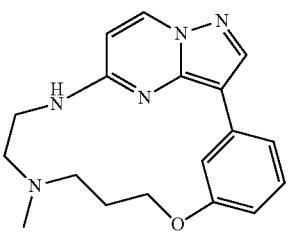 [SMILES: CN1CCCOc2cccc(c2)-c2cnn3ccc(nc23)NCC1]

Example H94 can be prepared following general scheme 1 and according to the procedures described to obtain example H91.

Example H95

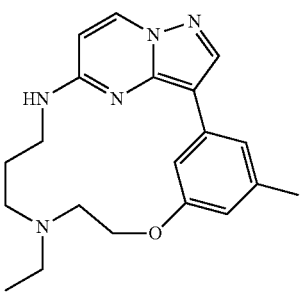 [SMILES: CCN1CCCNc2ccn3ncc(c3n2)-c2cc(C)cc(c2)OCC1]

Example H95 can be prepared following general scheme 1 and according to the procedures described to obtain example H91.

Example H96

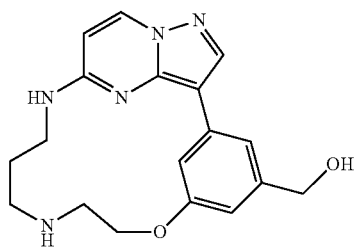 [SMILES: OCc1cc2cc(c1)-c1cnn3ccc(nc13)NCCCNCCO2]

Example H96 can be prepared following general scheme 1 and according to the procedures described to obtain example H80.

Example H97

Example H97 can be prepared following general scheme 1.

Preparation of Intermediate 33

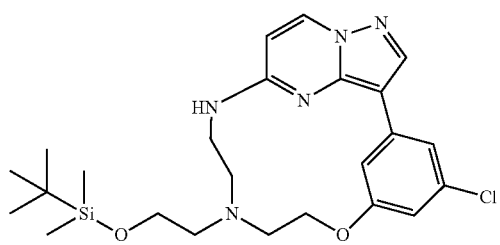 [SMILES: CC(C)(C)[Si](C)(C)OCCN1CCNc2ccn3ncc(c3n2)-c2cc(Cl)cc(c2)OCC1]

4-Chloro-7-oxa-10,13,17,18,21-pentaazatetracyclo [12.5.2.1^{2,6}.0^{17,20}]docosa-1(20),2(22),3,5,14(21), 15,18-heptaene can be obtained according to the procedures described in the patent application WO2013/045653 A1 to obtain example 17.

4-Chloro-7-oxa-10,13,17,18,21-pentaazatetracyclo [12.5.2.1^{2,6}.0^{17,20}]docosa-1(20),2(22),3,5,14(21), 15,18-heptaene (300 mg, 0.82 mmol) and diisopropylethylamine (429 µl, 2.46 mmol) were dissolved in a mixture of dichloromethane and methanol (1:1, 4.0 ml). tert-Butyldimethylsilyloxy)acetaldehyde (310 µl, 1.64 mmol) was added and the mixture stirred at room temperature for 30 minutes. Sodium triacetoxyborohydride (380 mg, 1.80 mmol) was added portion wise and the mixture was stirred at room temperature overnight. The solvent was removed under reduced pressure. The residue was purified by flash column chromatography over silica gel using a mixture of dichloromethane/methanol (9:1) and methanol as eluents (gradient elution from 0% to 40% of methanol). The product fractions were collected and the solvent was removed under reduced pressure.

Yield: 307 mg of intermediate 33 (77%)

LCMS method 1: MH$^+$=489, RT=1.105 min

Preparation of Example H97

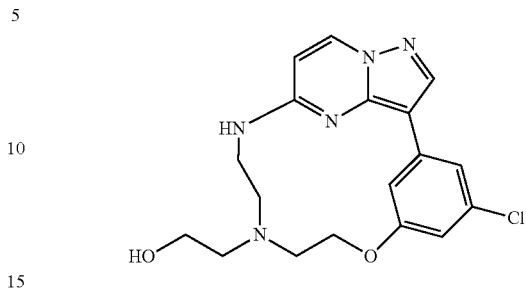

Intermediate 33 (307 mg, 0.63 mmol) was stirred in a mixture of acetic acid, tetrahydrofuran and water (3:1:1, 5 ml) at 60° C. overnight. The solvent was removed under reduced pressure. The residue was purified by flash column chromatography over silica gel using a mixture of dichloromethane/methanol (9:1) and methanol as eluents (gradient elution from 0% to 100% of methanol). The product fractions were collected and the solvent was removed under reduced pressure.

Yield: 137 mg of example H97 (58%)

LCMS method 2: MH$^+$=374, RT=2.080 min

Example H98

Example H98 can be prepared following general scheme 2.

Preparation of Intermediate 34

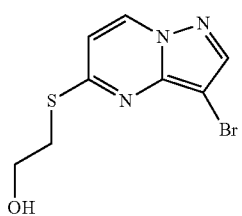 [SMILES: OCCSc1ccn2ncc(Br)c2n1]

A mixture of 3-bromo-5-chloro-pyrazolo[1,5-a]pyrimidine (10.0 g, 43.016 mmol), 2-sulfanylethanol (30.3 ml, 430.2 mmol) and diisopropylethylamine (22.5 ml, 129.05 mmol) was stirred at 150° C. overnight. Water was added, and the aqueous layer was extracted with n-butanol. The solvent of the combined organic layers was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

Yield: 10.57 g of intermediate 34 (90%)

LCMS method 1: MH$^+$=275 (MH$^+$-Boc), RT=0.541 min

Preparation of Intermediate 35

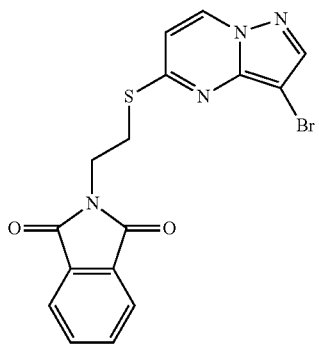 [SMILES: O=C1c2ccccc2C(=O)N1CCSc1ccn2ncc(Br)c2n1]

Diisopropyl azodicarboxylate (12.18 ml, 60.23 mmol) was added drop wise at 0° C. to a mixture of intermediate 34 (5.504 g, 20.08 mmol), isoindoline-1,3-dione (4.43 g, 30.12 mmol) and triphenylphosphine (15.8 g, 60.23 mmol) in dry 2-methyltetrahydrofuran (120 ml). The solvent was removed under reduced pressure, the residue was dissolved in ethyl acetate and washed with brine. The organic layer was dried, filtered and the solvent was removed under reduced pressure. The residue was purified by flash column chromatography over silica gel using heptane and ethyl acetate as eluents (gradient elution from 0% to 50% of ethyl acetate). The product fractions were collected and the solvent was removed under reduced pressure.

Preparation of Intermediate 36

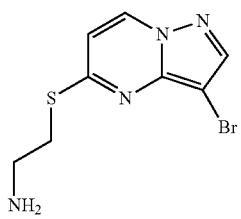 [SMILES: NCCSc1ccn2ncc(Br)c2n1]

Hydrazine (3.12 ml, 100.4 mmol) was added to a solution of intermediate 35 (20.08 mmol) and the mixture was stirred overnight at 60° C. The reaction mixture was cooled, filtered and the solvent was removed under reduced pressure. The residue was dissolved in ethyl acetate and washed with 1N sodium hydroxide and water. The organic layer was dried, filtered and the solvent was removed under reduced pressure. The product was used in the next step without further purification.

LCMS method 1: MH$^+$=273, RT=0.238 min

Preparation of Intermediate 37

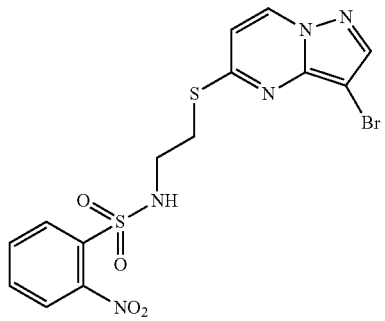 [SMILES: O=[N+]([O-])c1ccccc1S(=O)(=O)NCCSc1ccn2ncc(Br)c2n1]

2-Nitrobenzenesulfonyl chloride (3.26 g, 14.72 mmol) was added portion wise at 0° C. to a solution of intermediate 36 (13.83 mmol) and triethylamine (5.58 ml, 40.14 mmol) in dichloromethane (150 ml). The reaction mixture was diluted with ethyl acetate and washed with a saturated aqueous sodium bicarbonate solution. The organic layer was dried, filtered and the solvent was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

LCMS method 1: MH$^+$=458, RT=0.891 min

Preparation of Intermediate 38

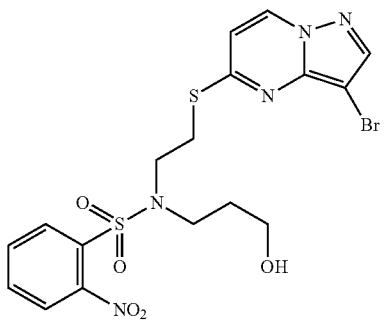 [SMILES: O=[N+]([O-])c1ccccc1S(=O)(=O)N(CCCO)CCSc1ccn2ncc(Br)c2n1]

Cesium carbonate (2.98 g, 9.16 mmol) was added at a solution of intermediate 37 (3.50 g, 7.637 mmol) in dichloromethane (40). 3-Bromopropan-1-ol (827 µl, 9.16 mmol) was added and the reaction mixture was stirred at 60° C. for 4 hours. The reaction mixture was cooled and concentrated under reduced pressure. The residue was diluted with ethyl acetate and the organic layer was washed with a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 0% to 50% of methanol). The product fractions were collected and the solvent was removed under reduced pressure.

LCMS method 1: MH$^+$=517, RT=0.861 min

Preparation of Intermediate 39

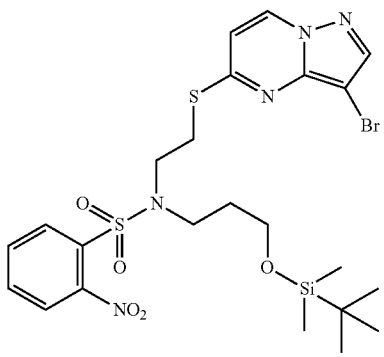 [SMILES: CC(C)(C)[Si](C)(C)OCCCN(CCSc1ccn2ncc(Br)c2n1)S(=O)(=O)c1ccccc1[N+](=O)[O-]]

Tert-butyldimethylsilyl chloride (1.27 g, 8.40 mmol) was added portion wise to a stirred solution of intermediate 38 (7.64 mmol) and triethylamine (3.19 ml, 22.92 mmol) in dichloromethane (100 ml). The mixture was stirred at room temperature overnight. The reaction mixture was diluted with dichloromethane and washed with a saturated aqueous sodium bicarbonate solution. The organic layer was dried, filtered and the solvent was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

Yield: 615 mg of intermediate 39 (13%)
LCMS method 1: MH⁺=632, RT=1.457 min

Preparation of Intermediate 40

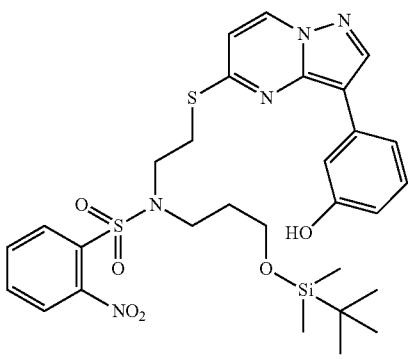 [SMILES: CC(C)(C)[Si](C)(C)OCCCN(CCSc1ccn2ncc(-c3cccc(O)c3)c2n1)S(=O)(=O)c1ccccc1[N+](=O)[O-]]

Intermediate 39 (600 mg, 0.951 mmol) was dissolved in a mixture of 1,4-dioxane and water (4:1, 20 ml) and the mixture was degassed by bubbling nitrogen gas through. (3-Hydroxyphenyl)boronic acid (197 mg, 1.43 mmol), tetrakis(triphenylphosphine)palladium(0) (116 mg, 0.10 mmol), 2-dicyclohexylphosphino-2',4',6'-triisopropylbiphenyl (Xphos) (91 mg, 0.19 mmol) and potassium phosphate tribasic (220 mg, 5 eq.) were added while stirring under nitrogen gas. The mixture was stirred at 100° C. overnight. The reaction mixture was cooled, the solvent was removed under reduced pressure and ethyl acetate was added. The organic layer was washed with water, dried, filtered and the solvent was removed under reduced pressure. The residue was purified by flash column chromatography over silica gel using heptane and ethyl acetate as eluents (gradient elution from 33% to 100% of ethyl acetate) and then by using then dichloromethane and methanol as eluents (gradient elution from 2% to 10% of methanol). The product fractions were collected and the solvent was removed under reduced pressure.

Yield: 400 mg of intermediate 40 (65%)
LCMS method 1: MH⁺=644, RT=1.342 min

Preparation of Intermediate 41

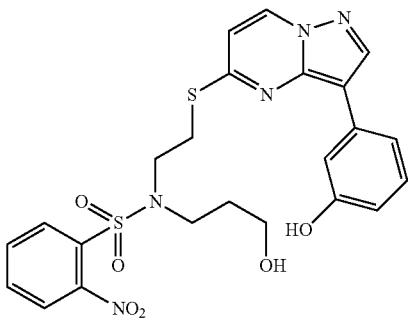 [SMILES: O=[N+]([O-])c1ccccc1S(=O)(=O)N(CCCO)CCSc1ccn2ncc(-c3cccc(O)c3)c2n1]

Water (4 ml) was a added to a solution of intermediate 40 (400 mg, 0.621 mmol) in tetrahydrofuran (4 ml). Acetic acid (8 ml) was added portion wise at 0° C. and the reaction mixture was stirred at room temperature overnight. The solvent was removed under reduced pressure and ethyl acetate was added. The organic layer was washed with a saturated aqueous sodium bicarbonate solution, dried, filtered and the solvent was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

Yield: 248 mg of intermediate 41 (75%)
LCMS method 1: MH⁺=530, RT=0.820 min

Preparation of Intermediate 42

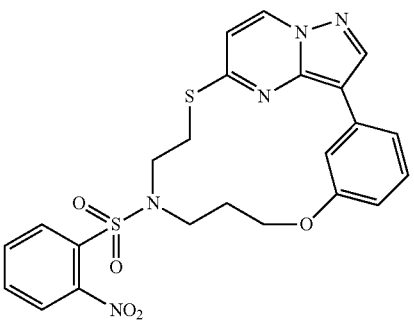 [SMILES: O=[N+]([O-])c1ccccc1S(=O)(=O)N1CCCOc2cccc(c2)-c2cnn3ccc(nc23)SCC1]

A solution of intermediate 41 (248 mg, 0.468 mmol) in 2-methyltetrahydrofuran (30 ml/mmol) was degassed by bubbling nitrogen gas through the mixture. A solution of diisopropyl azodicarboxylate (275 mg, 1.40 mmol) in toluene (100 ml/mmol) was degassed by bubbling nitrogen gas through the mixture. Both solutions were added drop wise and simultaneously over a period of 1 hour at 90° C. to a degassed solution of triphenylphosphine (367 mg, 1.40 mmol) in toluene (100 ml/mmol). The mixture was stirred at 90° C. for 1.5 hours. The reaction mixture was cooled and the solvent was removed under reduced pressure. The product was without further purification used in the next step.

LCMS method 1: MH⁺=512, RT=1.141 min

Preparation of Example H98

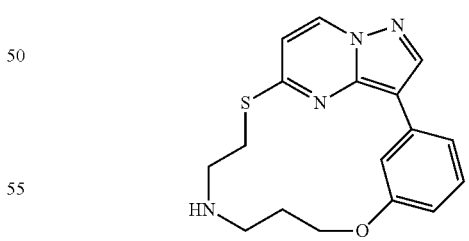

Cesium carbonate (231 mg, 0.71 mmol) was added to a solution of intermediate 42 (0.470 mmol) in N,N-dimethylformamide (5.0 ml). Thiophenol (62 µl, 0.56 mmol) was added and the mixture was stirred at room temperature for 2 hours. The solvent was removed under reduced pressure and ethyl acetate was added. The organic layer was washed with a saturated aqueous sodium bicarbonate solution, dried, filtered and the solvent was removed under reduced pressure. The residue was purified by flash column chromatography over silica gel using dichloromethane and methanol as eluents (gradient elution from 0% to 30% of methanol). The product fractions were collected and the solvent was removed under reduced pressure.

Yield: 77 mg of example H98 (50%)
LCMS method 2: MH$^+$=327, RT=1.844 min

Example H99

Example H99 can be prepared following general scheme 2 and according to the procedures described to obtain example H98.

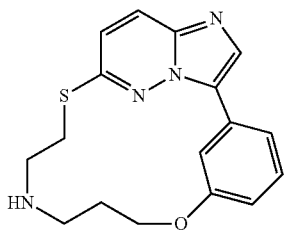 [SMILES: c1cc2cc(c1)-c1cnc3ccc(nn13)SCCNCCCO2]

Example H100

Example H100 can be prepared following general scheme 1.
Preparation of Intermediate 43

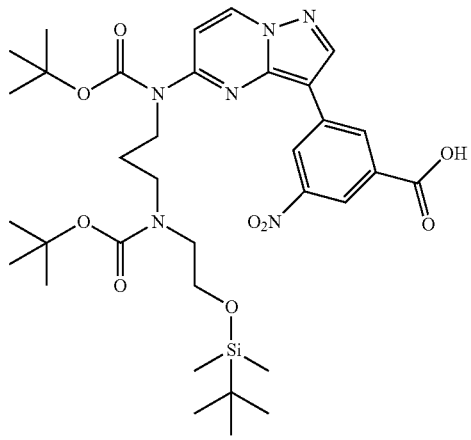 [SMILES: CC(C)(C)OC(=O)N(CCCN(C(=O)OC(C)(C)C)c1ccn2ncc(-c3cc(C(=O)O)cc([N+](=O)[O-])c3)c2n1)CCO[Si](C)(C)C(C)(C)C]

tert-Butyl N-(3-bromopyrazolo[1,5-a]pyrimidin-5-yl)-N-[3-[tert-butoxycarbonyl-[2-(tert-butyl(dimethyl)silyl)oxyethyl]amino]propyl]carbamate can be prepared according to similar procedures described in the patent application WO2013/045653 A1 to obtain intermediate 23.

A mixture of N-(3-bromopyrazolo[1,5-a]pyrimidin-5-yl)-N-[3-[tert-butoxycarbonyl-[2-(tert-butyl(dimethyl)silyl)oxyethyl]amino]propyl]carbamate (5.10 g, 8.112 mmol), 3-borono-5-nitro-benzoic acid (3.24 g, 10.55 mmol) and potassium phosphate tribasic (8.6 g, 5 eq.) dissolved in 1,4-dioxane and water (4:1, 40.0 ml) was degassed by bubbling nitrogen gas through the mixture. Tetrakis(triphenylphosphine)palladium(0) (185 mg, 0.16 mmol) and 2-dicyclohexylphosphino-2',4',6'-triisopropylbiphenyl (Xphos) (234 mg, 0.49 mmol) were added and the mixture was stirred under nitrogen gas at 80° C. for 16 hours. The reaction mixture was cooled and a saturated aqueous sodium bicarbonate solution was added. The aqueous layer was extracted with ethyl acetate. The combined organic layers were dried, filtered and the solvent was removed under reduced pressure. The residue was purified by flash column chromatography over silica gel using heptane and ethyl acetate as eluents (gradient elution from 0% to 50% ethyl acetate). The product fractions were collected and the solvent was evaporated.

Yield: 3.90 g of intermediate 43 (67%)
LCMS method 1: MH$^+$=615 (MH$^+$-Boc), RT=1.478 min
Preparation of Intermediate 44

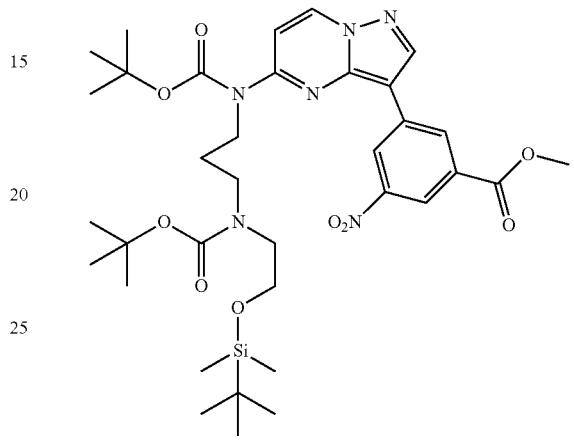

Cesium carbonate (1.95 g, 6.0 mmol) and methyl iodide (509 μl, 8.18 mmol) were added to a solution of intermediate 43 (3.90 g, 5.45 mmol) in acetonitrile (2 ml). The mixture was stirred at room temperature for 16 hours. Water was added and the product was extracted with ethyl acetate. The combined organic layers were dried, filtered and the solvent was removed under reduced pressure. The product was used in the next step without further purification.

LCMS method 2: MH$^+$=629 (MH$^+$-Boc), RT=1.627 min
Preparation of Intermediate 45

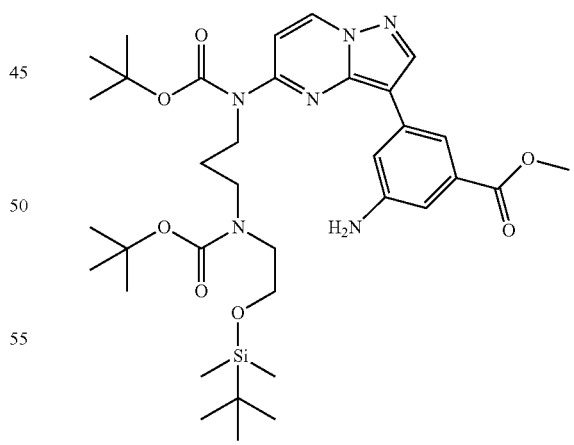

Palladium on charcoal (10% w/w) was added to a solution of intermediate 45 (3.0 g, 4.12 ml) in methanol (30 ml). The mixture was purged with hydrogen gas and stirred under hydrogen atmosphere (balloon) at room temperature for a period of 16 hours. The mixture was filtered over celite and the solvent was removed under reduced pressure. The product was used in the next step without further purification.

Yield: 1.93 g of intermediate 45 (67%)
LCMS method 2: MH$^+$=699, RT=5.506 min

Preparation of Intermediate 46

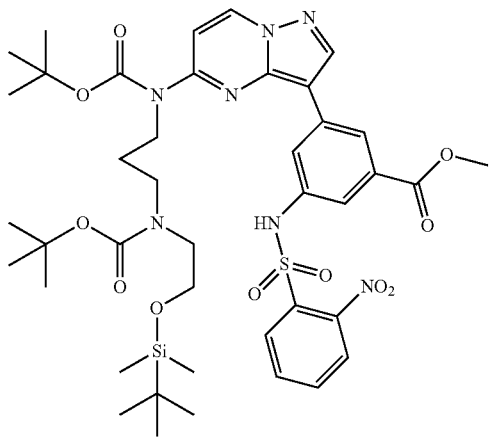 [SMILES: COC(=O)c1cc(NS(=O)(=O)c2ccccc2[N+](=O)[O-])cc(-c2cnn3ccc(N(CCCN(CCO[Si](C)(C)C(C)(C)C)C(=O)OC(C)(C)C)C(=O)OC(C)(C)C)nc23)c1]

Intermediate 45 (2.055 g, 2.94 mmol) was dissolved in dichloromethane (11 ml). Triethylamine (1.23 ml, 8.82 mmol) and 2-nitrobenzenesulfonyl chloride (1.30 g, 5.88 mmol) dissolved in dichloromethane (15 ml) was added slowly at 0° C. The reaction mixture was stirred at room temperature for 2 days. A saturated aqueous sodium bicarbonate solution was added and the product was extracted with dichloromethane. The combined organic layers were dried, filtered and the solvent was removed under reduced pressure. The residue was purified by flash column chromatography over silica gel using heptane and ethyl acetate as eluents (gradient elution from 0% to 70% of ethyl acetate). The product fractions were collected and the solvent was removed under reduced pressure.

Yield: 527 mg of intermediate 46 (20%)
LCMS method 1: MH$^+$=784 (=MW-Boc), RT=1.588 min Preparation of Intermediate 47

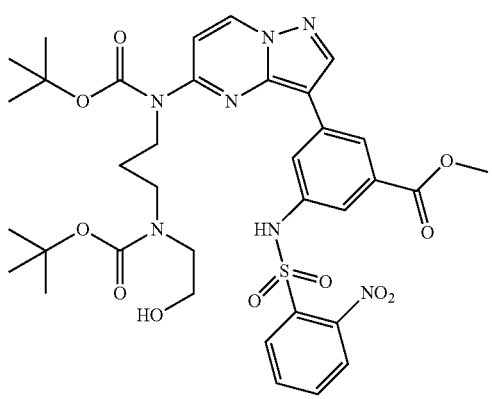 [SMILES: COC(=O)c1cc(NS(=O)(=O)c2ccccc2[N+](=O)[O-])cc(-c2cnn3ccc(N(CCCN(CCO)C(=O)OC(C)(C)C)C(=O)OC(C)(C)C)nc23)c1]

Intermediate 46 (527 mg, 0.60 mmol) was dissolved in a mixture of tetrahydrofuran and water (1:1, 3.6 ml). Acetic acid (5 ml) was added drop wise at 0° C. and the mixture was stirred at room temperature for 16 hours. The solvent was removed under reduced pressure. A saturated aqueous sodium bicarbonate solution was added and the product was extracted with ethyl acetate. The combined organic layers were dried, filtered and the solvent was removed under reduced pressure. The residue was purified by flash column chromatography over silica gel using heptane and ethyl acetate as eluents (gradient elution from 0% to 40% of ethyl acetate). The product fractions were collected and the solvent was removed under reduced pressure.

Yield: 375 mg of intermediate 47 (81%)
LCMS method 1: MH$^+$=792 (=MW+23), RT=1.189 min Preparation of Intermediate 48

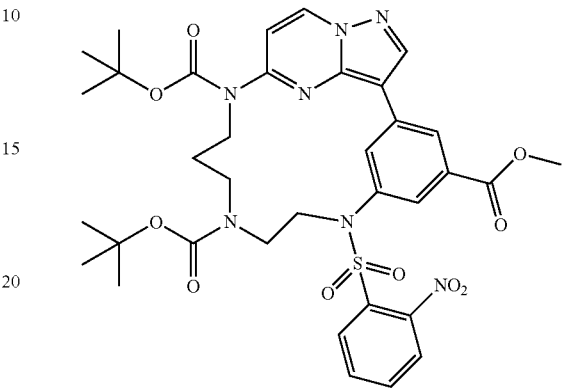

A solution of intermediate 47 (358 mg, 0.47 mmol) in 2-methyltetrahydrofuran (30 ml/mmol) was degassed by bubbling nitrogen gas through the mixture. A solution of diisopropyl azodicarboxylate (280 mg, 1.41 mmol) in toluene (30 ml/mmol) was degassed by bubbling nitrogen gas through the mixture. Both solutions were added drop wise and simultaneously over a period of 1 hour at 90° C. to a degassed solution of triphenylphosphine (370 mg, 1.41 mmol) in toluene (100 ml/mmol). The mixture was stirred at 90° C. for 30 minutes. The reaction mixture was cooled and the solvent was removed under reduced pressure. The residue was purified by flash column chromatography over silica gel using heptane and ethyl acetate as eluents (gradient elution from 0% to 100% of ethyl acetate). The product fractions were collected and the solvent was removed under reduced pressure.

LCMS method 1: MH$^+$=652 (=MH$^+$-Boc), RT=1.379 min

Preparation of Intermediate 49

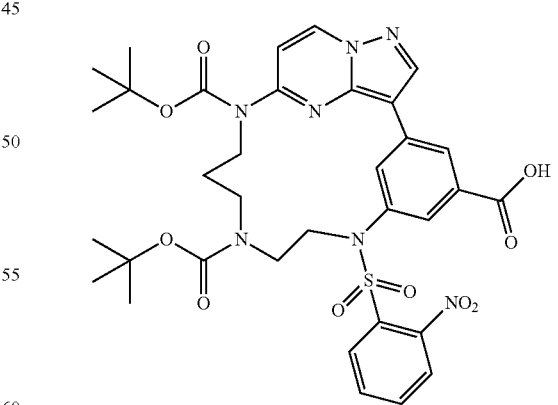

Intermediate 48 (0.47 mmol) and lithium hydroxide monohydrate (20 mg, 0.52 mmol) were dissolved in a mixture of tetrahydrofuran and water (4:1, 10 ml) and the reaction mixture was stirred at 50° C. for 16 hours. The solvent was removed under reduced pressure and the product was used without further purification in the next step.

LCMS method 1: MH⁺=738 (=MH⁺-Boc), RT=1.234 min
Preparation of Intermediate 50

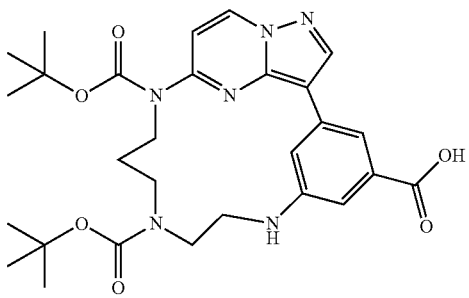 [SMILES: CC(C)(C)OC(=O)N1CCCN(C(=O)OC(C)(C)C)c2ccn3ncc(c3n2)-c2cc(cc(C(=O)O)c2)NCC1]

Intermediate 49 (0.47 mmol) was dissolved N,N-dimethylformamide (1.41 ml). Cesium carbonate (231 mg, 0.71 mmol) and thiophenol (50 µl, 0.52 mmol) were added and the mixture was stirred at room temperature for 16 hours. More cesium carbonate (1.1 eq.) and thiophenol (1.5 eq.) were added and the mixture was stirred at room temperature for 16 hours. A 1N aqueous sodium hydroxide solution was added and the product was extracted with ethyl acetate. The combined organic layers were dried, filtered and the solvent was removed under reduced pressure. The residue was purified by flash column chromatography over silica gel using dichloromethane and a mixture of dichloromethane and methanol (9:1) as eluents (gradient elution from 0% to 10% of the mixture of dichloromethane and methanol). The product fractions were collected and the solvent was removed under reduced pressure.

LCMS method 1: MH⁺=553, RT=1.142 min
Preparation of Intermediate 51

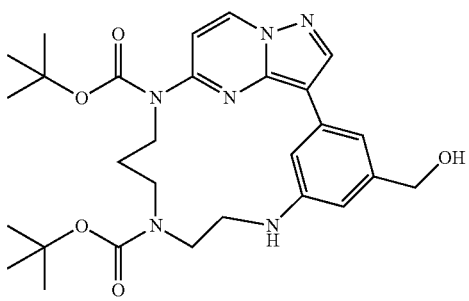 [SMILES: CC(C)(C)OC(=O)N1CCCN(C(=O)OC(C)(C)C)c2ccn3ncc(c3n2)-c2cc(CO)cc(c2)NCC1]

Intermediate 50 (80 mg, 0.14 mmol) was dissolved under nitrogen atmosphere in borane dimethylsulfide complex (9.2 ml). The suspension was stirred at 100° C. for 45 minutes. Ethyl acetate was added and the pH of the solution was adjusted at 0° C. with 1 N sodium hydroxide to pH 7. The product was extracted with ethyl acetate. The combined organic layers were dried, filtered and the solvent was removed under reduced pressure. heptane and ethyl acetate as eluents (gradient elution from 0% to 50% of ethyl acetate). The product fractions were collected and the solvent was removed under reduced pressure.

Yield: 47 mg of intermediate 51 (62%)
LCMS method 1: MH⁺=539, RT=1.106 min

Preparation of Example H100

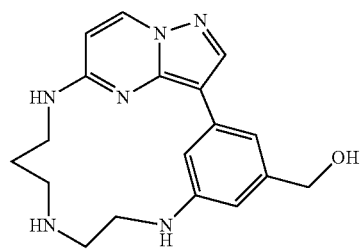 [SMILES: OCc1cc2cc(c1)-c1cnn3ccc(nc13)NCCCNCCN2]

Intermediate 51 (47 mg, 0.09 mmol) was dissolved in a 4N hydrochloric acid in 1,4-dioxane (0.27 ml) at 0° C. The mixture was stirred at room temperature for 16 hours. The solvent was removed under reduced pressure and the product was triturated with diethyl ether.

Yield: 26 mg of example H100 (85%)
LCMS method 2: MH⁺=339, RT=1.1383 min

TABLE 1

| | |
|---|---|
| 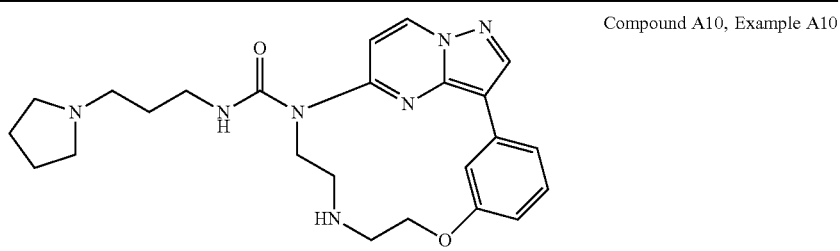 | Compound A10, Example A10 |
| 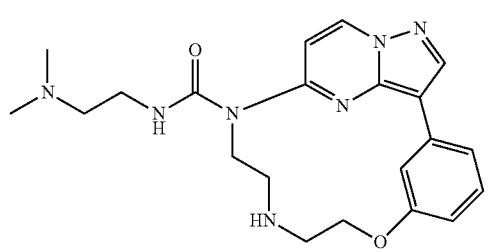 [SMILES: CN(C)CCNC(=O)N1CCNCCOc2cccc(c2)-c2cnn3ccc1nc23] | Compound A11, Example A11 |

TABLE 1-continued
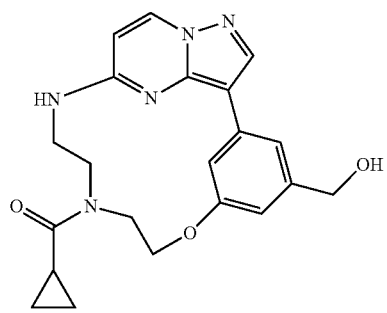 [SMILES: O=C(C1CC1)N1CCNc2ccn3ncc(c3n2)-c2cc(CO)cc(c2)OCC1]
Compound B75, Example B64
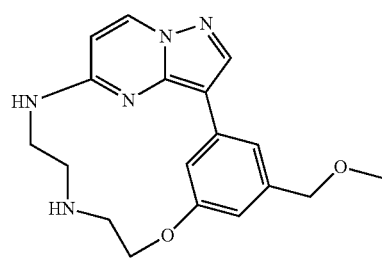 [SMILES: COCc1cc2cc(c1)-c1cnn3ccc(nc13)NCCNCCO2]
Compound H78, Example H78
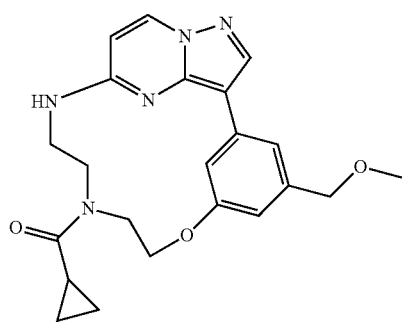 [SMILES: COCc1cc2cc(c1)-c1cnn3ccc(nc13)NCCN(C(=O)C1CC1)CCO2]
Compound H79, Example H79
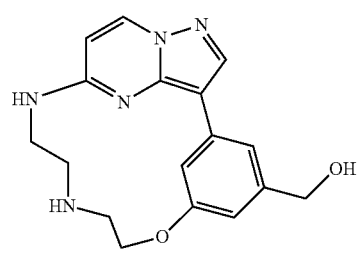 [SMILES: OCc1cc2cc(c1)-c1cnn3ccc(nc13)NCCNCCO2]
Compound H80, Example H80
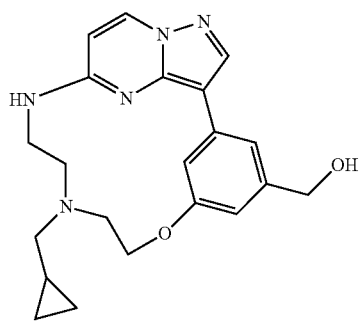 [SMILES: OCc1cc2cc(c1)-c1cnn3ccc(nc13)NCCN(CC1CC1)CCO2]
Compound H81, Example H81

TABLE 1-continued
| | |
|---|---|
| 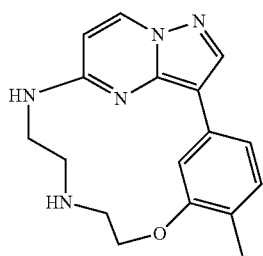 [SMILES: Cc1ccc2cc1OCCNCCNc1ccn3ncc-2c3n1] | Compound H82, Example H82 |
| 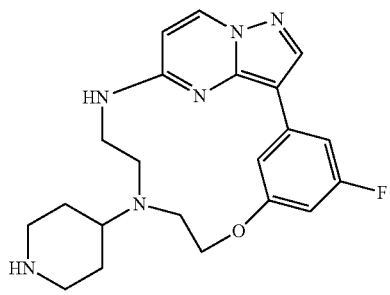 [SMILES: Fc1cc2cc(c1)-c1cnn3ccc(nc13)NCCN(C1CCNCC1)CCO2] | Compound H83, Example H83 |
| 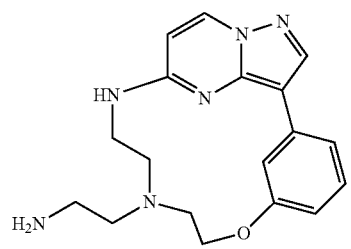 [SMILES: NCCN1CCNc2ccn3ncc(c3n2)-c2cccc(c2)OCC1] | Compound H84, Example H84 |
| 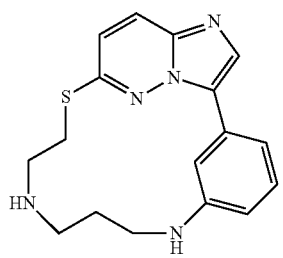 [SMILES: c1cc2cc(c1)-c1cnc3ccc(nn13)SCCNCCCN2] | Compound H85, Example H85 |
| 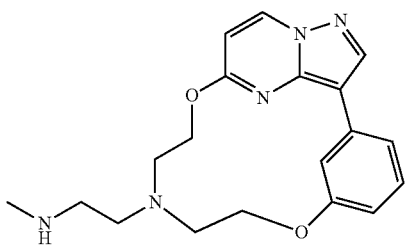 [SMILES: CNCCN1CCOc2cccc(c2)-c2cnn3ccc(nc23)OCC1] | Compound H86, Example H86 |
| 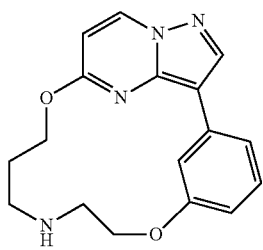 [SMILES: c1cc2cc(c1)-c1cnn3ccc(nc13)OCCCNCCO2] | Compound H87, Example H87 |

TABLE 1-continued
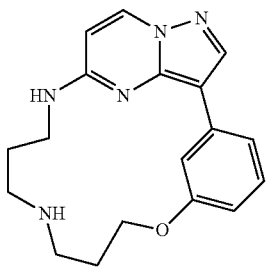 [SMILES: c1cc2cc(c1)-c1cnn3ccc(nc13)NCCCNCCCO2] Compound H88, Example H88
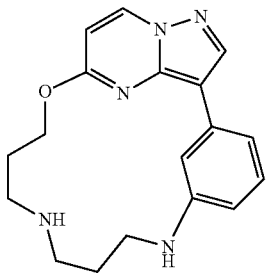 [SMILES: c1cc2cc(c1)-c1cnn3ccc(nc13)OCCCNCCCN2] Compound H89, Example H89
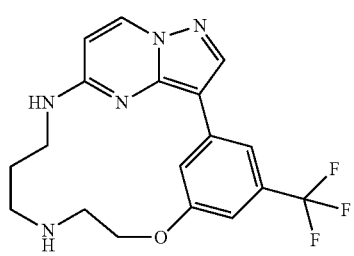 [SMILES: FC(F)(F)c1cc2cc(c1)-c1cnn3ccc(nc13)NCCCNCCO2] Compound H90, Example H90
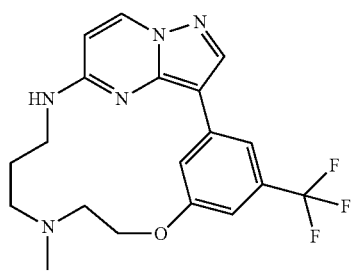 [SMILES: CN1CCCNc2ccn3ncc(c3n2)-c2cc(cc(C(F)(F)F)c2)OCC1] Compound H91, Example H91
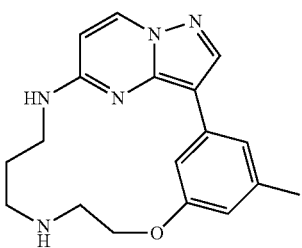 [SMILES: Cc1cc2cc(c1)-c1cnn3ccc(nc13)NCCCNCCO2] Compound H92, Example H92
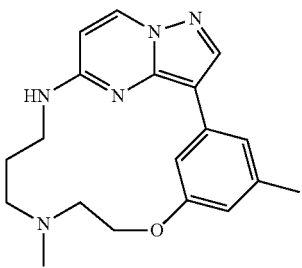 [SMILES: Cc1cc2cc(c1)-c1cnn3ccc(nc13)NCCCN(C)CCO2] Compound H93, Example H93

TABLE 1-continued
| | |
|---|---|
| 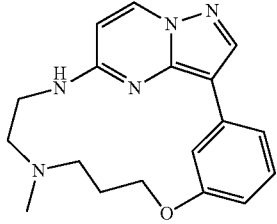 [SMILES: CN1CCCOc2cccc(c2)-c2cnn3ccc(nc23)NCC1] | Compound H94, Example H94 |
| 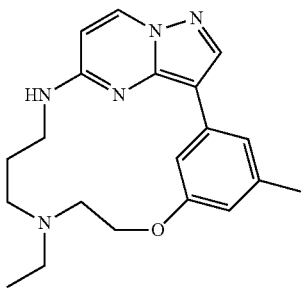 [SMILES: CCN1CCCNc2ccn3ncc(c3n2)-c2cc(C)cc(c2)OCC1] | Compound H95, Example H95 |
| 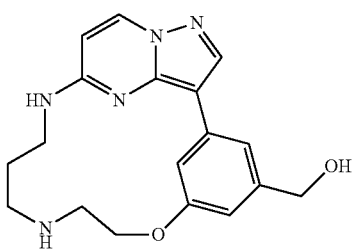 [SMILES: OCc1cc2cc(c1)-c1cnn3ccc(nc13)NCCCNCCO2] | Compound H96, Example H96 |
| 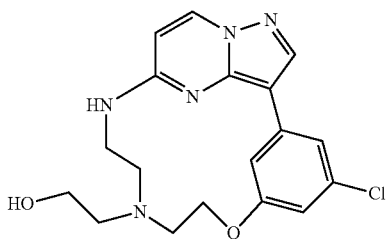 [SMILES: OCCN1CCNc2ccn3ncc(c3n2)-c2cc(Cl)cc(c2)OCC1] | Compound H97, Example H97 |
| 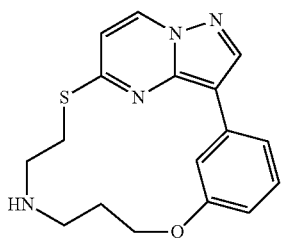 [SMILES: c1cc2cc(c1)-c1cnn3ccc(nc13)SCCNCCCO2] | Compound H98, Example H98 |
| 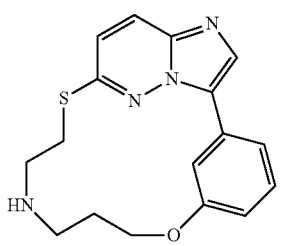 [SMILES: c1cc2cc(c1)-c1cnc3ccc(nn13)SCCNCCCO2] | Compound H99, Example H99 |

TABLE 1-continued

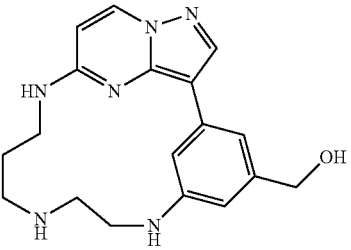 [SMILES: OCc1cc2cc(c1)-c1cnn3ccc(nc13)NCCCNCCN2]

Compound H100, Example H100

The compounds were identified according to the analytical methods and the analytical results described in WO2013/045653 A1 and WO2013/046029 A1.

TABLE 2

Melting points

| COMPOUND N° | MELTING POINT (° C.) |
|---|---|
| A10 | >300 |
| A11 | >300 |
| B75 | ND* |
| H78 | ND* |
| H79 | >300 |
| H80 | ND* |
| H81 | 179.1 |
| H82 | >300 |
| H83 | 246.2 |
| H84 | >300 |
| H85 | 173.1 |
| H86 | 247 |
| H87 | ND* |
| H88 | ND* |
| H89 | 273.3 |
| H90 | >300 |
| H91 | 207.3 |
| H92 | >300 |
| H93 | ND* |
| H94 | 288 |
| H95 | ND* |
| H96 | ND* |
| H97 | 285.2 |
| H98 | 178.1 |
| H99 | 125.6 |
| H100 | ND* |

*Not determined

TABLE 3

LCMS data

| COMPOUND NUMBER | MASS (MH)+ PEAK | RETENTION TIME (min) | LCMS METHOD |
|---|---|---|---|
| A10 | 451 | 1.180 | 2 |
| A11 | 410 | 1.131 | 2 |
| B75 | 394 | 2.426 | 2 |
| H78 | 340 | 1.485 | 2 |
| H79 | 408 | 2.624 | 2 |
| H80 | 326 | 1.391 | 2 |
| H81 | 380 | 1.671 | 2 |
| H82 | 310 | 2.138 | 2 |
| H83 | 397 | 2.244 | 2 |
| H84 | 339 | 2.113 | 2 |
| H85 | 326 | 1.513 | 2 |
| H86 | 354 | 2.260 | 2 |
| H87 | 311 | 1.865 | 2 |
| H88 | 324 | 1.875 | 2 |
| H89 | 324 | 1.867 | 2 |
| H90 | 378 | 2.158 | 2 |
| H91 | 302 | 2.170 | 2 |
| H92 | 324 | 1.869 | 2 |
| H93 | 338 | 0.333 | 2 |
| H94 | 324 | 1.787 | 2 |
| H95 | 352 | 2.047 | 2 |
| H96 | 340 | 1.441 | 2 |
| H97 | 374 | 2.080 | 2 |
| H98 | 327 | 1.844 | 2 |
| H99 | 327 | 1.603 | 2 |
| H100 | 339 | 1.383 | 2 |

The inhibition of SIK2 kinase was assessed using SIK2 recombinant protein in an in vitro peptide-based kinase assay.

Protocol

A radiometric protein kinase assay ($^{33}$PanQinase® Activity Assay) is used for measuring the kinase activity. All assays are performed in 96-well FlashPlates™ from Perkin Elmer in a 50 µl reaction volume. The reaction cocktail is 94ipette in 4 steps in the following order:

10 µl of non-radioactive ATP solution (in H2O)

25 µl of assay buffer/[γ-$^{33}$P]-ATP mixture

5 µl of test sample in 10% DMSO

10 µl of enzyme/substrate mixture

The assay for SIK2 contains 70 mM HEPES-NaOH pH 7.5, 3 mM MgCl$_2$, 3 mM MnCl$_2$, 3 µM Na-orthovanadate, 1.2 mM DTT, 50 µg/ml PEG20000, ATP (1.0 µM), [γ-$^{33}$P]-ATP (approx. 5×10$^{05}$ cpm per well), protein kinase SIK2 (0.3 nM) and substrate (RBER-Chktide), 2.0 µg/50 µl).

The kinase is obtained from Invitrogen Corporation.

The reaction cocktails were incubated at 30° C. for 60 minutes. The reaction was stopped with 50 µl of 2% (v/v) H$_3$PO$_4$, plates were aspirated and washed two times with 200 µl 0.9% (w/v) NaCl. Incorporation of $^{33}$Pi (counting of "cpm") was determined with a microplate scintillation counter.

Compounds

The compounds are dissolved to 10 mM in DMSO. Where needed, solutions are sonicated in a bath sonicator.

Table 4 provides the pIC$_{50}$ values and % Remaining activity values at two concentrations (1 µM and 0.1 µM) of the compounds according to the invention, obtained using the above mentioned kinase assay.

TABLE 4

| Compound N° | IC$_{50}$ for SIK2 | % Remaining SIK2 activity at 1 μM | % Remaining SIK2 activity at 0.1 μM |
|---|---|---|---|
| A10 | | ** | ** |
| A11 | +++ | ** | ** |
| B75 | | ** | ** |
| H78 | +++ | ** | ** |
| H79 | +++ | | |
| H80 | +++ | | |
| H81 | +++ | ** | ** |
| H82 | +++ | ** | ** |
| H83 | +++ | ** | ** |
| H84 | +++ | ** | ** |
| H85 | +++ | ** | ** |
| H86 | +++ | ** | ** |
| H87 | +++ | ** | * |
| H88 | +++ | ** | ** |
| H89 | +++ | ** | * |
| H90 | +++ | ** | ** |
| H91 | +++ | ** | ** |
| H92 | +++ | ** | ** |
| H93 | +++ | ** | ** |
| H94 | +++ | | |
| H95 | +++ | ** | ** |
| H96 | +++ | ** | ** |
| H97 | +++ | ** | ** |
| H98 | ++ | ** | ** |
| H99 | ++ | | |
| H100 | +++ | ** | ** |

+ indicates an IC50 >1 μM,
++ indicates an IC50 of between 100 nM and 1 μM, and
+++ indicates an IC50 <100 nM
* indicates a % remaining kinase activity above 50%,
** indicates a % remaining kinase activity below 50%
ND = Not determined

The invention claimed is:

1. A method for the treatment of a SIK-kinase associated disease selected from ischemia, pigmentation-related disorders, ovarian cancer, and melanoma, said method comprising administering to a subject in need thereof a compound of Formula I or a stereoisomer, tautomer, racemic, salt, or N-oxide form, thereof,

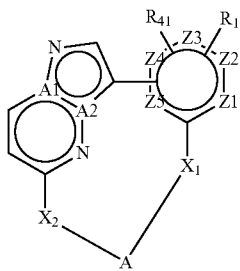

I wherein:

$A_1$ and $A_2$ are selected from C and N; wherein when $A_1$ is C, then $A_2$ is N; and wherein when $A_2$ is C, then $A_1$ is N;

$R_1$ and $R_{41}$ are each independently selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —Ar$_7$ and -Het$_1$; wherein each of said —C$_{1-6}$alkyl is optionally and independently substituted with from 1 to 3 substituents selected from -halo, —OH, —NR$_{11}$R$_{12}$, —O—C$_{1-6}$alkyl, and —S—C$_{1-6}$alkyl;

$R_2$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=S)—C$_{1-6}$alkyl, —(C=O)—O—C$_{1-6}$alkyl, —(C=S)—O—C$_{1-6}$alkyl, —(C=O)—NR$_{27}$R$_{28}$, —(C=S)—NR$_{27}$R$_{28}$, —C$_{3-6}$cycloalkyl, -Het$_3$, —Ar$_2$, —(C=O)-Het$_3$, —(C=S)-Het$_3$, —(C=O)—Ar$_2$, —(C=S)—Ar$_2$, —(C=O)—C$_{3-6}$cycloalkyl, —(C=S)—C$_{3-6}$cycloalkyl, and —SO$_2$—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, and —NR$_{13}$R$_{14}$;

$R_3$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=S)—C$_{1-6}$alkyl, —(C=O)—O—C$_{1-6}$alkyl, —(C=S)—O—C$_{1-6}$alkyl, —(C=O)—NR$_{29}$R$_{30}$, —(C=S)—NR$_{29}$R$_{30}$, —C$_{3-6}$cycloalkyl -Het$_2$, —Ar$_3$, —(C=O)-Het$_2$, —(C=S)-Het$_2$, —(C=O)—Ar$_3$, —(C=S)—Ar$_3$, —(C=O)—C$_{3-6}$cycloalkyl, —(C=S)—C$_{3-6}$cycloalkyl and —SO$_2$—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_2$, —Ar$_3$, and —NR$_{15}$R$_{16}$;

$R_4$ is independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —Ar$_8$ and -Het$_4$;

$R_5$ and $R_7$ are each independently selected from —H, —OH, -halo, —C$_{1-6}$alkyl, —O—C$_{1-6}$alkyl, —S—C$_{1-6}$alkyl, -Het$_9$, —Ar$_1$, —C$_{3-6}$cycloalkyl, —SO$_2$—Ar$_1$, —SO$_2$, —SO$_2$—C$_{1-6}$alkyl, —(C=O), —(C=O)—C$_{1-6}$alkyl, —(C=S), —(C=S)—C$_{1-6}$alkyl, —O—(C=O)—C$_{1-6}$alkyl, —O—(C=S)—C$_{1-6}$alkyl, —(C=O)—O—C$_{1-6}$alkyl, and —(C=S)—O—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, —Ar$_1$, -Het$_9$, and —NR$_{23}$R$_{24}$;

$R_6$ is selected from —C$_{1-6}$alkyl, —SO$_2$, —SO$_2$—C$_{1-6}$alkyl, —SO$_2$—C$_{3-6}$cycloalkyl, —(C=O), —(C=O)—C$_{1-6}$alkyl, —(C=O)—C$_{2-6}$alkenyl, —(C=O)—O—C$_{1-6}$alkyl, —(C=O)-Het$_6$, —(C=O)—Ar$_6$, —(C=O)—C$_{3-6}$cycloalkyl, —(C=O)—NR$_{31}$R$_{32}$, —(C=O)—NR$_{31}$—(C=O)—R$_{32}$, —(C=S), —(C=S)—C$_{1-6}$alkyl, —(C=S)—C$_{2-6}$alkenyl, —(C=S)—O—C$_{1-6}$alkyl, —(C=S)-Het$_6$, —(C=S)—Ar$_6$, —(C=S)—C$_{3-6}$cycloalkyl, —(C=S)—NR$_{31}$R$_{32}$, —(C=S)—NR$_{31}$—(C=S)—R$_{32}$, -Het$_6$, —Ar$_6$, and —C$_{3-6}$cycloalkyl;

wherein each of said —C$_{1-6}$alkyl is optionally and independently substituted with from 1 to 3 substituents selected from =O, -halo, —OH, —O—C$_{1-6}$alkyl, —S—C$_{1-6}$alkyl, —C$_{3-6}$cycloalkyl, -Het$_6$, —Ar$_6$, —NR$_{25}$R$_{26}$, —(C=O)—NR$_{25}$R$_{26}$, —NR$_{33}$(C=O)—NR$_{25}$R$_{26}$, —(C=S)—NR$_{25}$R$_{26}$, and —NR$_{33}$(C=S)—NR$_{25}$R$_{26}$; and wherein each of said —C$_{3-6}$cycloalkyl is optionally and independently substituted with from 1 to 3 substituents selected from —C$_{1-6}$alkyl, =O, -halo, —OH, —O—C$_{1-6}$alkyl, —S—C$_{1-6}$alkyl, -Het$_{12}$, —Ar$_{11}$, and —NR$_{53}$R$_{54}$, —(C=O)—NR$_{53}$R$_{54}$, —NR$_{55}$(C=O)—NR$_{53}$R$_{54}$, —(C=S)—NR$_{53}$R$_{54}$, and —NR$_{55}$(C=S)—NR$_{53}$R$_{54}$;

$R_8$ is selected from —NR$_{34}$—(C=O)—R$_{35}$, —NR$_{34}$—(C=S)—R$_{35}$, —NR$_{36}$—(C=O)—NR$_{34}$R$_{35}$, —NR$_{36}$—(C=S)—NR$_{34}$R$_{35}$, —NR$_{34}$—(SO$_2$)—R$_{35}$, —NR$_{34}$—(C=O)—O—R$_{35}$, —NR$_{34}$—(C=S)—O—R$_{35}$, —O—(C=O)—NR$_{34}$R$_{35}$, and —O—(C=S)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$, R$_{40}$, R$_{44}$, R$_{45}$, R$_{46}$, R$_{47}$, R$_{48}$, R$_{49}$, R$_{50}$, R$_{53}$, R$_{54}$ and R$_{55}$ are each independently selected from —H, -halo, =O, —OH, —C$_{1-6}$alkyl, —O—C$_{1-6}$alkyl, —S—C$_{1-6}$alkyl, —C$_{3-6}$cycloalkyl, —Ar$_5$ and -Het$_7$; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_7$, —Ar$_5$ and —NR$_{51}$R$_{52}$;

R$_{51}$ and R$_{52}$ are each independently selected from —H, -halo, —OH, —C$_{1-6}$alkyl, —O—C$_{1-6}$alkyl, —S—C$_{1-6}$alkyl, —C$_{3-6}$cycloalkyl, —Ar$_{10}$ and -Het$_{10}$;

R$_{42}$ is selected from —H, —OH, -halo, —C$_{1-6}$alkyl, —O—C$_{1-6}$alkyl, —S—C$_{1-6}$alkyl, —NR$_{46}$R$_{47}$, —C$_{3-6}$cycloalkyl, —Ar$_9$ and -Het$_8$;

R$_{43}$ is selected from —H —C$_{1-6}$alkyl, and —C$_{3-6}$cycloalkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, -Het$_5$, —C$_{3-6}$cycloalkyl —Ar$_4$, and —NR$_{44}$R$_{45}$;

A is selected from —(CH$_2$)$_n$—Y—(CH$_2$)$_m$—, —(C=O)—, —(C=S)—, —(C=N)—R$_{49}$—, —(SO$_2$)—, —SO$_2$—NR$_5$—, —(C=O)—NR$_5$—, —(C=S)—NR$_5$—, —NR$_5$—(C=O)—NR$_7$—, —NR$_5$—(C=S)—NR$_7$—, —NR$_6$—, —NR$_5$—(C=O)—O—, —NR$_5$—(C=S)—O—, and —CHR$_8$—;

X$_1$ is selected from —C$_{1-6}$alkyl-, —O—C$_{1-6}$alkyl-, —S—C$_{1-6}$alkyl-, —(C=O)—, —NR$_3$—(C=O)—, —C$_{1-6}$alkyl-NR$_3$—, —NR$_3$—, —(C=O)—, —NR$_3$—(C=O)—NR$_{48}$—, —NR$_3$—C$_{1-6}$alkyl-, —NR$_3$—SO$_2$—, —NR$_3$—(C=O)—C$_{1-6}$alkyl-, —(C=O)—NR$_3$—C$_{1-6}$alkyl-, —O—C$_{1-6}$alkyl-O—C$_{1-6}$alkyl- and —C$_{1-6}$alky-NR$_3$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{37}$R$_{38}$;

X$_2$ is selected from —C$_{1-6}$alkyl-, —O—C$_{1-6}$alkyl-, —S—C$_{1-6}$alkyl-, —(C=O)—, —NR$_2$—(C=O)—, —C$_{1-6}$alkyl-NR$_2$—, —NR$_2$—, —(C=O)—, —NR$_2$—(C=O)—NR$_{50}$—, —NR$_2$—C$_{1-6}$alkyl-, —NR$_2$—SO$_2$—, —NR$_2$—(C=O)—C$_{1-6}$alkyl-, —(C=O)—NR$_2$—C$_{1-6}$alkyl-, —O—C$_{1-6}$alkyl-O—C$_{1-6}$alkyl- and —C$_{1-6}$alkyl-NR$_2$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{39}$R$_{40}$;

Y is selected from a direct bond, —CHR$_{42}$—, —O—, —S—, and —NR$_{43}$—;

Ar$_1$, Ar$_2$, Ar$_3$, Ar$_4$, Ar$_5$, Ar$_6$, Ar$_7$, Ar$_8$, Ar$_9$, Ar$_{10}$ and Ar$_{11}$ are each independently a 5- to 10-membered aromatic heterocycle optionally comprising 1 or 2 heteroatoms selected from O, N and S; each of said Ar$_1$, Ar$_2$, Ar$_3$, Ar$_4$, Ar$_5$, Ar$_6$, Ar$_7$, Ar$_8$, Ar$_9$, and Ar$_{10}$ being optionally substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, —OH, —C$_{1-6}$alkyl, —OC$_{1-6}$alkyl, —SC$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N; and m and n are each independently 1, 2, 3, or 4.

2. The method of claim 1, wherein:

A$_1$ is C and A$_2$ is N;

R$_1$ and R$_{41}$ are each independently selected from —H, -halo, —OH, —C$_{1-6}$alkyl, —O—C$_{1-6}$alkyl, —S—C$_{1-6}$alkyl, —NR$_9$R$_{10}$, —(C=O)—R$_4$, —(C=S)—R$_4$, —SO$_2$—R$_4$, —CN, —NR$_9$—SO$_2$—R$_4$, —C$_{3-6}$cycloalkyl, —Ar$_7$ and -Het$_1$; wherein each of said —C$_{1-6}$alkyl is optionally and independently substituted with from 1 to 3 substituents selected from -halo, —OH, —NR$_{11}$R$_{12}$, —O—C$_{1-6}$alkyl, and —S—C$_{1-6}$alkyl;

R$_2$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=S)—C$_{1-6}$alkyl, —(C=O)—O—C$_{1-6}$alkyl, —(C=S)—O—C$_{1-6}$alkyl, —(C=O)—NR$_{27}$R$_{28}$, —(C=S)—NR$_{27}$R$_{28}$, —C$_{3-6}$cycloalkyl, -Het$_3$, —Ar$_2$, —(C=O)-Het$_3$, —(C=S)-Het$_3$, —(C=O)—Ar$_2$, —(C=S)—Ar$_2$, —(C=O)—C$_{3-6}$cycloalkyl, —(C=S)—C$_{3-6}$cycloalkyl, and —SO$_2$—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, and —NR$_{13}$R$_{14}$;

R$_3$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=S)—C$_{1-6}$alkyl, —(C=O)—O—C$_{1-6}$alkyl, —(C=S)—O—C$_{1-6}$alkyl, —(C=O)—NR$_{29}$R$_{30}$, —(C=S)—NR$_{29}$R$_{30}$, —C$_{3-6}$cycloalkyl -Het$_2$, —Ar$_3$, —(C=O)-Het$_2$, —(C=S)-Het$_2$, —(C=O)—Ar$_3$, —(C=S)—Ar$_3$, —(C=O)—C$_{3-6}$cycloalkyl, —(C=S)—C$_{3-6}$cycloalkyl and —SO$_2$—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, -Het$_2$, —Ar$_3$, and —NR$_{15}$R$_{16}$;

R$_4$ is independently selected from -halo, —OH, —C$_{1-6}$alkyl, —O—C$_{1-6}$alkyl, —S—C$_{1-6}$alkyl, —NR$_{17}$R$_{18}$, —C$_{3-6}$cycloalkyl, —Ar$_8$ and -Het$_4$;

R$_5$ and R$_7$ are each independently selected from —H, —OH, -halo, —C$_{1-6}$alkyl, —O—C$_{1-6}$alkyl, —S—C$_{1-6}$alkyl, -Het$_9$, —Ar$_1$, —C$_{3-6}$cycloalkyl, —SO$_2$—Ar$_1$, —SO$_2$, —SO$_2$—C$_{1-6}$alkyl, —(C=O), —(C=O)—C$_{1-6}$alkyl, —(C=S), —(C=S)—C$_{1-6}$alkyl, —O—(C=O)—C$_{1-6}$alkyl, —O—(C=S)—C$_{1-6}$alkyl, —(C=O)—O—C$_{1-6}$alkyl, and —(C=S)—O—C$_{1-6}$alkyl; wherein each of said —C$_{1-6}$alkyl is optionally and independently substituted with from 1 to 3 substituents selected from -halo, —OH, —O—C$_{1-6}$alkyl, —S—C$_{1-6}$alkyl, —C$_{3-6}$cycloalkyl, —Ar$_1$, -Het$_9$, and —NR$_{23}$R$_{24}$;

$R_6$ is selected from $-C_{1-6}$alkyl, $-SO_2$, $-SO_2-C_{1-6}$alkyl, $-SO_2-C_{3-6}$cycloalkyl, $-(C=O)$, $-(C=O)-C_{1-6}$alkyl, $-(C=O)-C_{2-6}$alkenyl, $-(C=O)-O-C_{1-6}$alkyl, $-(C=O)$-Het$_6$, $-(C=O)$-Ar$_6$, $-(C=O)-C_{3-6}$cycloalkyl, $-(C=O)-NR_{31}R_{32}$, $-(C=O)-NR_{31}-(C=O)-R_{32}$, $-(C=S)$, $-(C=S)-C_{1-6}$alkyl, $-(C=S)-C_{2-6}$alkenyl, $-(C=S)-O-C_{1-6}$alkyl, $-(C=S)$-Het$_6$, $-(C=S)$-Ar$_6$, $-(C=S)-C_{3-6}$cycloalkyl, $-(C=S)-NR_{31}R_{32}$, $-(C=S)-NR_{31}-(C=S)-R_{32}$, -Het$_6$, $-Ar_6$, and $-C_{3-6}$cycloalkyl;

wherein each of said $-C_{1-6}$alkyl is optionally and independently substituted with from 1 to 3 substituents selected from $=O$, -halo, $-OH$, $-O-C_{1-6}$alkyl, $-S-C_{1-6}$alkyl, $-C_{3-6}$cycloalkyl, -Het$_6$, $-Ar_6$, $-NR_{25}R_{26}$, $-(C=O)-NR_{25}R_{26}$, $-NR_{33}(C=O)-NR_{25}R_{26}$, $-(C=S)-NR_{25}R_{26}$, and $-NR_{33}(C=S)-NR_{25}R_{26}$; and wherein each of said $-C_{3-6}$cycloalkyl is optionally and independently substituted with from 1 to 3 substituents selected from $-C_{1-6}$alkyl, $=O$, -halo, $-OH$, $-O-C_{1-6}$alkyl, $-S-C_{1-6}$alkyl, -Het$_{12}$, $-Ar_{11}$, and $-NR_{53}R_{54}$, $-(C=O)-NR_{53}R_{54}$, $-NR_{55}(C=O)-NR_{53}R_{54}$, $-(C=S)-NR_{53}R_{54}$, and $-NR_{55}(C=S)-NR_{53}R_{54}$;

$R_8$ is selected from $-NR_{34}-(C=O)-R_{35}$, $-NR_{34}(C=S)-R_{35}$, $-NR_{36}-(C=O)-NR_{34}R_{35}$, $-NR_{36}-(C=S)-NR_{34}R_{35}$, $-NR_{34}-(SO_2)-R_{35}$, $-NR_{34}-(C=O)-O-R_{35}$, $-NR_{34}-(C=S)-O-R_{35}$, $-O-(C=O)-NR_{34}R_{35}$, and $-O-(C=S)-NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from $-H$, -halo, $=O$, $-OH$, $-C_{1-6}$alkyl, $-O-C_{1-6}$alkyl, $-S-C_{1-6}$alkyl, $-C_{3-6}$cycloalkyl, $-Ar_5$ and -Het$_7$; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, $-C_{3-6}$cycloalkyl, -Het$_7$, $-Ar_5$ and $-NR_{51}R_{52}$;

$R_{51}$ and $R_{52}$ are each independently selected from $-H$, -halo, $-OH$, $-C_{1-6}$alkyl, $-O-C_{1-6}$alkyl, $-S-C_{1-6}$alkyl, $-C_{3-6}$cycloalkyl, $-Ar_{10}$ and -Het$_{10}$;

$R_{42}$ is selected from $-H$, $-OH$, -halo, $-C_{1-6}$alkyl, $-O-C_{1-6}$alkyl, $-S-C_{1-6}$alkyl, $-NR_{46}R_{47}$, $-C_{3-6}$cycloalkyl, $-Ar_9$ and -Het$_8$;

$R_{43}$ is selected from $-H$ $-C_{1-6}$alkyl, and $-C_{3-6}$cycloalkyl; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, -Het$_5$, $-C_{3-6}$cycloalkyl $-Ar_4$, and $-NR_{44}R_{45}$;

A is selected from $-(CH_2)_n-Y-(CH_2)_m-$, $-(C=O)-$, $-(C=S)-$, $-(C=N)-R_{49}-$, $-(SO_2)-$, $-SO_2-NR_5-$, $-(C=O)-NR_5-$, $-(C=S)-NR_5-$, $-NR_5-(C=O)-NR_7-$, $-NR_5-(C=S)-NR_7-$, $-NR_6-$, $-NR_5-(C=O)-O-$, $-NR_5-(C=S)-O-$, and $-CHR_8-$;

$X_1$ is selected from $-C_{1-6}$alkyl-, $-O-C_{1-6}$alkyl-, $-S-C_{1-6}$alkyl-, $-(C=O)-$, $-NR_3-(C=O)-$, $-C_{1-6}$alkyl-NR$_3-$, $-NR_3-$, $-(C=O)-$, $-NR_3-(C=O)-NR_{48}-$, $-NR_3-C_{1-6}$alkyl-, $-NR_3-SO_2-$, $-NR_3-(C=O)-C_{1-6}$alkyl-, $-(C=O)-NR_3-C_{1-6}$alkyl-, $-O-C_{1-6}$alkyl-O-C$_{1-6}$alkyl- and $-C_{1-6}$alkyl-NR$_3-C_{1-6}$alkyl-; wherein each of said $-C_{1-6}$alkyl- is optionally and independently substituted with from 1 to 3 substituents selected from -halo, $-OH$, $-C_{1-6}$alkyl, $-O-C_{1-6}$alkyl, $-S-C_{1-6}$alkyl, -phenyl, and $-NR_{37}R_{38}$;

$X_2$ is selected from $-C_{1-6}$alkyl-, $-O-C_{1-6}$alkyl-, $-S-C_{1-6}$alkyl-, $-(C=O)-$, $-NR_2-(C=O)-$, $-C_{1-6}$alkyl-NR$_2-$, $-NR_2-$, $-(C=O)-$, $-NR_2-(C=O)-NR_{50}-$, $-NR_2-C_{1-6}$alkyl-, $-NR_2-SO_2-$, $-NR_2-(C=O)-C_{1-6}$alkyl-, $-(C=O)-NR_2-C_{1-6}$alkyl-, $-O-C_{1-6}$alkyl-O-C$_{1-6}$alkyl- and $-C_{1-6}$alkyl-NR$_2-C_{1-6}$alkyl-; wherein each of said $-C_{1-6}$alkyl- is optionally and independently substituted with from 1 to 3 substituents selected from -halo, $-OH$, $-C_{1-6}$alkyl, $-O-C_{1-6}$alkyl, $-S-C_{1-6}$alkyl, -phenyl and $-NR_{39}R_{40}$;

Y is selected from a direct bond, $-CHR_{42}-$, $-O-$, $-S-$, and $-NR_{43}-$;

$Ar_1$, $Ar_2$, $Ar_3$, $Ar_4$, $Ar_5$, $Ar_6$, $Ar_7$, $Ar_8$, $Ar_9$, $Ar_{10}$ and $Ar_{11}$ are each independently a 5- to 10-membered aromatic heterocycle optionally comprising 1 or 2 heteroatoms selected from O, N and S; each of said $Ar_1$, $Ar_2$, $Ar_3$, $Ar_4$, $Ar_5$, $Ar_6$, $Ar_7$, $Ar_8$, $Ar_9$, and $Ar_{10}$ being optionally and independently substituted with from 1 to 3 substituents selected from -halo, $-OH$, $-C_{1-6}$alkyl, $-O-C_{1-6}$alkyl, $-S-C_{1-6}$alkyl, and $-NR_{19}R_{20}$; wherein each of said $-C_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, $-OH$, $-C_{1-6}$alkyl, $-OC_{1-6}$alkyl, $-SC_{1-6}$alkyl, $=O$, $-(C=O)-C_{1-6}$alkyl, and $-NR_{21}R_{22}$; wherein each of said $-C_{1-6}$alkyl is optionally and independently substituted with from 1 to 3 -halo;

$Z_1$, $Z_2$, $Z_3$, $Z_4$ and $Z_5$ are each independently selected from C and N; and m and n are each independently 1, 2, 3, or 4.

3. The method of claim 1, wherein:

$A_1$ is N and $A_2$ is C;

$R_1$ and $R_{41}$ are each independently selected from $-H$, -halo, $-OH$, $-C_{1-6}$alkyl, $-O-C_{1-6}$alkyl, $-S-C_{1-6}$alkyl, $-NR_9R_{10}$, $-(C=O)-R_4$, $-(C=S)-R_4$, $-SO_2-R_4$, $-CN$, $-NR_9-SO_2-R_4$, $-C_{3-6}$cycloalkyl, $-Ar_7$ and -Het$_1$; wherein each of said $-C_{1-6}$alkyl is optionally and independently substituted with from 1 to 3 substituents selected from -halo, $-OH$, $-NR_{11}R_{12}$, $-O-C_{1-6}$alkyl, and $-S-C_{1-6}$alkyl;

$R_2$ is selected from $-H$, -halo, $-OH$, $-C_{1-6}$alkyl, $-O-C_{1-6}$alkyl, $-S-C_{1-6}$alkyl, $-(C=O)-C_{1-6}$alkyl, $-(C=S)-C_{1-6}$alkyl, $-(C=O)-O-C_{1-6}$alkyl, $-(C=S)-O-C_{1-6}$alkyl, $-(C=O)-NR_{27}R_{28}$, $-(C=S)-NR_{27}R_{28}$, $-C_{3-6}$cycloalkyl, -Het$_3$, $-Ar_2$, $-(C=O)$-Het$_3$, $-(C=S)$-Het$_3$, $-(C=O)-Ar_2$, $-(C=S)-Ar_2$, $-(C=O)-C_{3-6}$cycloalkyl, $-(C=S)-C_{3-6}$cycloalkyl, and $-SO_2-C_{1-6}$alkyl; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, -Het$_3$, $-Ar_2$, and $-NR_{13}R_{14}$;

$R_3$ is selected from $-H$, -halo, $-OH$, $-C_{1-6}$alkyl, $-O-C_{1-6}$alkyl, $-S-C_{1-6}$alkyl, $-(C=O)-C_{1-6}$alkyl, $-(C=S)-C_{1-6}$alkyl, $-(C=O)-O-C_{1-6}$ alkyl, $-(C=S)-O-C_{1-6}$alkyl, $-(C=O)-NR_{29}R_{30}$, $-(C=S)-NR_{29}R_{30}$, $-C_{3-6}$cycloalkyl -Het$_2$, $-Ar_3$, $-(C=O)$-Het$_2$, $-(C=S)$-Het$_2$, $-(C=O)-Ar_3$, $-(C=S)-Ar_3$, $-(C=O)-C_{3-6}$cycloalkyl, $-(C=S)-C_{3-6}$cycloalkyl and $-SO_2-C_{1-6}$alkyl; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, $-C_{3-6}$cycloalkyl, -Het$_2$, $-Ar_3$, and $-NR_{15}R_{16}$;

$R_4$ is independently selected from -halo, $-OH$, $-C_{1-6}$alkyl, $-O-C_{1-6}$alkyl, $-S-C_{1-6}$alkyl, $-NR_{17}R_{18}$, $-C_{3-6}$cycloalkyl, -Ar$_8$ and -Het$_4$;

$R_5$ and $R_7$ are each independently selected from $-H$, $-OH$, -halo, $-C_{1-6}$alkyl, $-O-C_{1-6}$alkyl, $-S-C_{1-6}$alkyl, -Het$_9$, $-Ar_1$, $-C_{3-6}$cycloalkyl, $-SO_2-Ar_1$, $-SO_2$, $-SO_2-C_{1-6}$alkyl, $-(C=O)$, $-(C=O)-C_{1-6}$alkyl, $-(C=S)$, $-(C=S)-C_{1-6}$alkyl, $-O-(C=O)-C_{1-6}$alkyl, $-O-(C=S)-C_{1-6}$alkyl, $-(C=O)-O-C_{1-6}$alkyl, and $-(C=S)-O-C_{1-6}$alkyl; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, $-C_{3-6}$cycloalkyl, $-Ar_1$, -Het$_9$, and $-NR_{23}R_{24}$;

$R_6$ is selected from $-C_{1-6}$alkyl, $-SO_2$, $-SO_2-C_{1-6}$alkyl, $-SO_2-C_{3-6}$cycloalkyl, $-(C=O)$, $-(C=O)-C_{1-6}$alkyl, $-(C=O)-C_{2-6}$ alkenyl, $-(C=O)-O-C_{1-6}$alkyl, $-(C=O)$-Het$_6$, $-(C=O)-Ar_6$, $-(C=O)-C_{3-6}$cycloalkyl, $-(C=O)-NR_{31}R_{32}$, $-(C=O)-NR_{31}-(C=O)-R_{32}$, $-(C=S)$, $-(C=S)-C_{1-6}$alkyl, $-(C=S)-C_{2-6}$alkenyl, $-(C=S)-O-C_{1-6}$alkyl, $-(C=S)$-Het$_6$, $-(C=S)-Ar_6$, $-(C=S)-C_{3-6}$cycloalkyl, $-(C=S)-NR_{31}R_{32}$, $-(C=S)-NR_{31}-(C=S)-R_{32}$, -Het$_6$, $-Ar_6$, and $-C_{3-6}$cycloalkyl;
wherein each of said $-C_{1-6}$alkyl is optionally and independently substituted with from 1 to 3 substituents selected from $=O$, -halo, $-OH$, $-O-C_{1-6}$alkyl, $-S-C_{1-6}$alkyl, $-C_{3-6}$cycloalkyl, -Het$_6$, $-Ar_6$, $-NR_{25}R_{26}$, $-(C=O)-NR_{25}R_{26}$, $-NR_{33}(C=O)-NR_{25}R_{26}$, $-(C=S)-NR_{25}R_{26}$, and $-NR_{33}(C=S)-NR_{25}R_{26}$; and
wherein each of said $-C_{3-6}$cycloalkyl is optionally and independently substituted with from 1 to 3 substituents selected from $-C_{1-6}$alkyl, $=O$, -halo, $-OH$, $-O-C_{1-6}$alkyl, $-S-C_{1-6}$alkyl, -Het$_{12}$, $-Ar_{11}$, and $-NR_{53}R_{54}$, $-(C=O)-NR_{53}R_{54}$, $-NR_{55}(C=O)-NR_{53}R_{54}$, $-(C=S)-NR_{53}R_{54}$, and $-NR_{55}(C=S)-NR_{53}R_{54}$;

$R_8$ is selected from $-NR_{34}-(C=O)-R_{35}$, $-NR_{34}-(C=S)-R_{35}$, $-NR_{36}-(C=O)-NR_{34}R_{35}$, $-NR_{36}-(C=S)-NR_{34}R_{35}$, $-NR_{34}-(SO_2)-R_{35}$, $-NR_{34}-(C=O)-O-R_{35}$, $-NR_{34}-(C=S)-O-R_{35}$, $-O-(C=O)-NR_{34}R_{35}$, and $-O-(C=S)-NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from $-H$, -halo, $=O$, $-OH$, $-C_{1-6}$alkyl, $-O-C_{1-6}$alkyl, $-S-C_{1-6}$alkyl, $-C_{3-6}$cycloalkyl, $-Ar_5$ and -Het$_7$; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, $-C_{3-6}$cycloalkyl, -Het$_7$, $-Ar_5$ and $-NR_{51}R_{52}$;

$R_{51}$ and $R_{52}$ are each independently selected from $-H$, -halo, $-OH$, $-C_{1-6}$alkyl, $-O-C_{1-6}$alkyl, $-S-C_{1-6}$alkyl, $-C_{3-6}$cycloalkyl, $-Ar_{10}$ and -Het$_{10}$;

$R_{42}$ is selected from $-H$, $-OH$, -halo, $-C_{1-6}$alkyl, $-O-C_{1-6}$alkyl, $-S-C_{1-6}$alkyl, $-NR_{46}R_{47}$, $-C_{3-6}$cycloalkyl, $-Ar_9$ and -Het$_8$;

$R_{43}$ is selected from $-H$ $-C_{1-6}$alkyl, and $-C_{3-6}$cycloalkyl; wherein each of said $-C_{1-6}$alkyl is optionally and independently substituted with from 1 to 3 substituents selected from -halo, $-OH$, $-O-C_{1-6}$alkyl, $-S-C_{1-6}$alkyl, -Het$_5$, $-C_{3-6}$cycloalkyl $-Ar_4$, and $-NR_{44}R_{45}$;

A is selected from $-(CH_2)_n-Y-(CH_2)_m-$, $-(C=O)-$, $-(C=S)-$, $-(C=N)-R_{49}-$, $-(SO_2)-$, $-SO_2-NR_5-$, $-(C=O)-NR_5-$, $-(C=S)-NR_5-$, $-NR_5-(C=O)-NR_7-$, $-NR_5-(C=S)-NR_7-$, $-NR_6-$, $-NR_5-(C=O)-O-$, $-NR_5-(C=S)-O-$, and $-CHR_8-$;

$X_1$ is selected from $-C_{1-6}$alkyl-, $-O-C_{1-6}$alkyl-, $-S-C_{1-6}$alkyl-, $-(C=O)-$, $-NR_3-(C=O)-$, $-C_{1-6}$alkyl-NR$_3-$, $-NR_3-$, $-(C=O)-$, $-NR_3-(C=O)-NR_{48}-$, $-NR_3-C_{1-6}$alkyl-, $-NR_3-SO_2-$, $-NR_3-(C=O)-C_{1-6}$alkyl-, $-(C=O)-NR_3-C_{1-6}$alkyl-, $-O-C_{1-6}$alkyl-O-C$_{1-6}$alkyl- and $-C_{1-6}$alkyl-NR$_3-C_{1-6}$alkyl-; wherein each of said $-C_{1-6}$alkyl- is optionally and independently substituted with from 1 to 3 substituents selected from -halo, $-OH$, $-C_{1-6}$alkyl, $-O-C_{1-6}$alkyl, $-S-C_{1-6}$alkyl, -phenyl, and $-NR_{37}R_{38}$;

$X_2$ is selected from $-C_{1-6}$alkyl-, $-O-C_{1-6}$alkyl-, $-S-C_{1-6}$alkyl-, $-(C=O)-$, $-NR_2-(C=O)-$, $-C_{1-6}$alkyl-NR$_2-$, $-NR_2-$, $-(C=O)-$, $-NR_2-(C=O)-NR_{50}-$, $-NR_2-C_{1-6}$alkyl-, $-NR_2-SO_2-$, $-NR_2-(C=O)-C_{1-6}$alkyl-, $-(C=O)-NR_2-C_{1-6}$alkyl-, $-O-C_{1-6}$alkyl-O-C$_{1-6}$alkyl- and $-C_{1-6}$alkyl-NR$_2-C_{1-6}$alkyl-; wherein each of said $-C_{1-6}$alkyl- is optionally and independently substituted with from 1 to 3 substituents selected from -halo, $-OH$, $-C_{1-6}$alkyl, $-O-C_{1-6}$alkyl, $-S-C_{1-6}$alkyl, -phenyl and $-NR_{39}R_{40}$;

Y is selected from a direct bond, $-CHR_{42}-$, $-O-$, $-S-$, and $-NR_{43}-$;

$Ar_1$, $Ar_2$, $Ar_3$, $Ar_4$, $Ar_5$, $Ar_6$, $Ar_7$, $Ar_8$, $Ar_9$, $Ar_{10}$ and $Ar_{11}$ are each independently a 5- to 10-membered aromatic heterocycle optionally comprising 1 or 2 heteroatoms selected from 0, N and S; each of said $Ar_1$, $Ar_2$, $Ar_3$, $Ar_4$, $Ar_5$, $Ar_6$, $Ar_7$, $Ar_8$, $Ar_9$, and $Ar_{10}$ being optionally and independently substituted with from 1 to 3 substituents selected from -halo, $-OH$, $-C_{1-6}$alkyl, $-O-C_{1-6}$alkyl, $-S-C_{1-6}$alkyl, and $-NR_{19}R_{20}$; wherein each of said $-C_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, $-OH$, $-C_{1-6}$alkyl, $-OC_{1-6}$alkyl, $-SC_{1-6}$alkyl, $=O$, $-(C=O)-C_{1-6}$alkyl, and $-NR_{21}R_{22}$; wherein each of said $-C_{1-6}$alkyl is optionally and independently substituted with from 1 to 3 -halo;

$Z_1$, $Z_2$, $Z_3$, $Z_4$ and $Z_5$ are each independently selected from C and N; and m and n are each independently 1, 2, 3, or 4.

4. The method of claim 1, wherein:
$A_1$ and $A_2$ are selected from C and N; wherein when $A_1$ is C, then $A_2$ is N; and wherein when $A_2$ is C, then $A_1$ is N;
$R_1$ and $R_{41}$ are each independently selected from —H, -halo, —OH, —$C_{1-6}$alkyl, and —(C=O)—$R_4$;
  wherein each of said —$C_{1-6}$alkyl is optionally and independently substituted with from 1 to 3 substituents selected from -halo, —OH, and —O—$C_{1-6}$alkyl;
$R_2$ is selected from —H and —(C=O)—$NR_{27}R_{28}$;
$R_3$ is —H;
$R_4$ is —$NR_{17}R_{18}$;
$R_6$ is selected from —$C_{1-6}$alkyl, —(C=O)—$C_{3-6}$cycloalkyl, -$Het_6$, and —$C_{3-6}$cycloalkyl;
  wherein each of said —$C_{1-6}$alkyl is optionally and independently substituted with from 1 to 3 substituents selected from —OH, —$C_{3-6}$cycloalkyl, -$Het_6$, —$NR_{25}R_{26}$, and —(C=O)—$NR_{25}R_{26}$;
  and wherein each of said —$C_{3-6}$cycloalkyl is optionally and independently substituted with from 1 to 3 substituents selected from =O;
$R_{17}$, $R_{18}$, $R_{25}$, $R_{26}$, $R_{27}$, and $R_{28}$ are each independently selected from —H, and —$C_{1-6}$alkyl; wherein each of said —$C_{1-6}$alkyl is optionally and independently substituted with from 1 to 3 substituents selected from -$Het_7$, and —$NR_{51}R_{52}$;
$R_{51}$ and $R_{52}$ are each —$C_{1-6}$alkyl;
$R_{43}$ is —H;
A is selected from —$(CH_2)_n$—Y—$(CH_2)_m$—, and —$NR_6$—;
$X_1$ is selected from —O—$C_{1-6}$alkyl-, —S—$C_{1-6}$alkyl- and —$C_{1-6}$alkyl-$NR_3$—;
$X_2$ is selected from —O—$C_{1-6}$alkyl-, —S—$C_{1-6}$alkyl-, —$C_{1-6}$alkyl-$NR_2$—, and —$NR_2$—$C_{1-6}$alkyl-;
Y is —$NR_{43}$—;
$Het_6$ and $Het_7$ are each independently selected from a 5- to 10-membered heterocycle having from 1 to 3 heteroatoms selected from O, N and S;
$Z_1$, $Z_2$, $Z_3$, $Z_4$ and $Z_5$ are each independently selected from C and N; and
m and n are each independently 1, 2, 3, or 4.

5. The method of claim 1, wherein:
$A_1$ is C and $A_2$ is N;
$R_1$ and $R_{41}$ are each independently selected from —H, -halo, —OH, —$C_{1-6}$alkyl, and —(C=O)—$R_4$;
  wherein each of said —$C_{1-6}$alkyl is optionally and independently substituted with from 1 to 3 substituents selected from -halo, —OH, and —O—$C_{1-6}$alkyl;
$R_2$ is selected from —H and —(C=O)—$NR_{27}R_{28}$;
$R_3$ is —H;
$R_4$ is —$NR_{17}R_{18}$;
$R_6$ is selected from —$C_{1-6}$alkyl, —(C=O)—$C_{3-6}$cycloalkyl, -$Het_6$, and —$C_{3-6}$cycloalkyl;
  wherein each of said —$C_{1-6}$alkyl is optionally and independently substituted with from 1 to 3 substituents selected from —OH, —$C_{3-6}$cycloalkyl, -$Het_6$, —$NR_{25}R_{26}$, and —(C=O)—$NR_{25}R_{26}$;
  and wherein each of said —$C_{3-6}$cycloalkyl is optionally and independently substituted with from 1 to 3 substituents selected from =O
$R_{17}$, $R_{18}$, $R_{25}$, $R_{26}$, $R_{27}$, and $R_{28}$ are each independently selected from —H, and —$C_{1-6}$alkyl; wherein each of said —$C_{1-6}$alkyl is optionally and independently substituted with from 1 to 3 substituents selected from -$Het_7$, and —$NR_{51}R_{52}$;
$R_{51}$ and $R_{52}$ are each —$C_{1-6}$alkyl;
$R_{43}$ is —H;
A is selected from —$(CH_2)_n$—Y—$(CH_2)_m$—, and —$NR_6$—;
$X_1$ is selected from —O—$C_{1-6}$alkyl-, —S—$C_{1-6}$alkyl- and —$C_{1-6}$alkyl-$NR_3$—;
$X_2$ is selected from —O—$C_{1-6}$alkyl-, —S—$C_{1-6}$alkyl-, and —$C_{1-6}$alkyl-$NR_2$—;
Y is —$NR_{43}$—;
$Het_6$ and $Het_7$ are each independently selected from a 5- to 10-membered heterocycle having from 1 to 3 heteroatoms selected from O, N and S;
$Z_1$, $Z_2$, $Z_3$, $Z_4$ and $Z_5$ are each independently selected from C and N; and
m and n are each independently 1, 2, 3, or 4.

6. The method of claim 1, wherein:
$A_1$ is N and $A_2$ is C;
$R_1$ and $R_{41}$ are each independently selected from —H, -halo, —OH, —$C_{1-6}$alkyl, and —(C=O)—$R_4$;
  wherein each of said —$C_{1-6}$alkyl is optionally and independently substituted with from 1 to 3 substituents selected from -halo, —OH, and —O—$C_{1-6}$alkyl;
$R_2$ is selected from —H and —(C=O)—$NR_{27}R_{28}$;
$R_3$ is —H;
$R_4$ is —$NR_{17}R_{18}$;
$R_6$ is selected from —$C_{1-6}$alkyl, —(C=O)—$C_{3-6}$cycloalkyl, -$Het_6$, and —$C_{3-6}$cycloalkyl;
  wherein each of said —$C_{1-6}$alkyl is optionally and independently substituted with from 1 to 3 substituents selected from —OH, —$C_{3-6}$cycloalkyl, -$Het_6$, —$NR_{25}R_{26}$, and —(C=O)—$NR_{25}R_{26}$;
  and wherein each of said —$C_{3-6}$cycloalkyl is optionally and independently substituted with from 1 to 3 substituents selected from =O;
$R_{17}$, $R_{18}$, $R_{25}$, $R_{26}$, $R_{27}$, and $R_{28}$ are each independently selected from —H, and —$C_{1-6}$alkyl; wherein each of said —$C_{1-6}$alkyl is optionally and independently substituted with from 1 to 3 substituents selected from -$Het_7$, and —$NR_{51}R_{52}$;
$R_{51}$ and $R_{52}$ are each —$C_{1-6}$alkyl;
$R_{43}$ is —H;
A is selected from —$(CH_2)_n$—Y—$(CH_2)_m$—, and —$NR_6$—;
$X_1$ is selected from —O—$C_{1-6}$alkyl-, —S—$C_{1-6}$alkyl- and —$C_{1-6}$alkyl-$NR_3$—;
$X_2$ is selected from —O—$C_{1-6}$alkyl-, —S—$C_{1-6}$alkyl-, —$C_{1-6}$alkyl-$NR_2$—, and —$NR_2$—$C_{1-6}$alkyl-;
Y is —$NR_{43}$—;
$Het_6$ and $Het_7$ are each independently selected from a 5- to 10-membered heterocycle having from 1 to 3 heteroatoms selected from O, N and S;
$Z_1$, $Z_2$, $Z_3$, $Z_4$ and $Z_5$ are each independently selected from C and N; and
m and n are each independently 1, 2, 3, or 4.

7. The method of claim 1, wherein the pyrazolopyrimidine or the imidazopyridazine moiety is linked to the aryl or heteroaryl moiety at position $Z_4$ or $Z_5$, in accordance with the numbering as provided in Formula I.

8. The method of claim 1, wherein $R_1$ is linked to the aryl or heteroaryl moiety at position $Z_1$, $Z_2$ or $Z_3$, in accordance with the numbering as provided in Formula I.

9. A method for the treatment of a SIK-kinase associated disease selected from ischemia, pigmentation-related diseases, ovarian cancer, diffuse large B-cell lymphoma, melanoma, non-small cell lung cancer, stroke, cardiac hypertrophy, Crohn's disease, and rheumatoid arthritis, said method comprising administering to a subject in need thereof a compound of Formula I or a stereoisomer, tautomer, racemic, salt, or N-oxide form thereof,

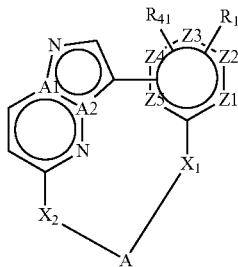

I wherein:
- $A_1$ and $A_2$ are selected from C and N; wherein when $A_1$ is C, then $A_2$ is N; and wherein when $A_2$ is C, then $A_1$ is N;
- $R_1$ and $R_{41}$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —(C=S)—$R_4$, —$SO_2$—$R_4$, —CN, —$NR_9$—$SO_2$—$R_4$, —$C_{3-6}$cycloalkyl, —$Ar_7$ and -$Het_1$; wherein each of said —$C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;
- $R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{27}R_{28}$, —(C=S)—$NR_{27}R_{28}$, —$C_{3-6}$cycloalkyl, -$Het_3$, —$Ar_2$, —(C=O)-$Het_3$, —(C=S)-$Het_3$, —(C=O)—$Ar_2$, —(C=S)—$Ar_2$, —(C=O)—$C_{3-6}$cycloalkyl, —(C=S)—$C_{3-6}$cycloalkyl, and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;
- $R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=S)—$C_{1-6}$alkyl, —(C=O)—O—$C_{1-6}$alkyl, —(C=S)—O—$C_{1-6}$alkyl, —(C=O)—$NR_{29}R_{30}$, —(C=S)—$NR_{29}R_{30}$, —$C_{3-6}$cycloalkyl -$Het_2$, —$Ar_3$, —(C=O)-$Het_2$, —(C=S)-$Het_2$, —(C=O)—$Ar_3$, —(C=S)—$Ar_3$, —(C=O)—$C_{3-6}$cycloalkyl, —(C=S)—$C_{3-6}$cycloalkyl and —$SO_2$—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_2$, —$Ar_3$, and —$NR_{15}R_{16}$;
- $R_4$ is independently selected from -halo, —OH, —$C_{1-6}$alkyl, —O—$C_{1-6}$alkyl, —S—$C_{1-6}$alkyl, —$NR_{17}R_{18}$, —$C_{3-6}$cycloalkyl, —$Ar_8$ and -$Het_4$;
- $R_5$ and $R_7$ are each independently selected from —H, —OH, -halo, —$C_{1-6}$alkyl, —O—$C_{1-6}$alkyl, —S—$C_{1-6}$alkyl, -$Het_9$, —$Ar_1$, —$C_{3-6}$cycloalkyl, —$SO_2$—$Ar_1$, —$SO_2$, —$SO_2$—$C_{1-6}$alkyl, —(C=O), —(C=O)—$C_{1-6}$alkyl, —(C=S), —(C=S)—$C_{1-6}$alkyl, —O—(C=O)—$C_{1-6}$alkyl, —O—(C=S)—$C_{1-6}$alkyl, —(C=O)—O—$C_{1-6}$alkyl, and —(C=S)—O—$C_{1-6}$alkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, —$Ar_1$, -$Het_9$, and —$NR_{23}R_{24}$;
- $R_6$ is selected from —$C_{1-6}$alkyl, —$SO_2$, —$SO_2$—$C_{1-6}$alkyl, —$SO_2$—$C_{3-6}$cycloalkyl, —(C=O), —(C=O)—$C_{1-6}$alkyl, —(C=O)—$C_{2-6}$alkenyl, —(C=O)—O—$C_{1-6}$alkyl, —(C=O)-$Het_6$, —(C=O)—$Ar_6$, —(C=O)—$C_{3-6}$cycloalkyl, —(C=O)—$NR_{31}R_{32}$, —(C=O)—$NR_{31}$—(C=O)—$R_{32}$, —(C=S), —(C=S)—$C_{1-6}$alkyl, —(C=S)—$C_{2-6}$alkenyl, —(C=S)—O—$C_{1-6}$alkyl, —(C=S)-$Het_6$, —(C=S)—$Ar_6$, —(C=S)—$C_{3-6}$cyclo alkyl, —(C=S)—$NR_{31}R_{32}$, —(C=S)—$NR_{31}$—(C=S)—$R_{32}$, -$Het_6$, —$Ar_6$, and —$C_{3-6}$cycloalkyl;
  - wherein each of said —$C_{1-6}$alkyl is optionally and independently substituted with from 1 to 3 substituents selected from =O, -halo, —OH, —O—$C_{1-6}$alkyl, —S—$C_{1-6}$alkyl, —$C_{3-6}$cycloalkyl, -$Het_6$, —$Ar_6$, —$NR_{25}R_{26}$, —(C=O)—$NR_{25}R_{26}$, —$NR_{33}$(C=O)—$NR_{25}R_{26}$, —(C=S)—$NR_{25}R_{26}$, and —$NR_{33}$(C=S)—$NR_{25}R_{26}$; and
  - wherein each of said —$C_{3-6}$cycloalkyl is optionally and independently substituted with from 1 to 3 substituents selected from —$C_{1-6}$alkyl, =O, -halo, —OH, —O—$C_{1-6}$alkyl, —S—$C_{1-6}$alkyl, -$Het_{12}$, —$Ar_{11}$, and —$NR_{53}R_{54}$, —(C=O)—$NR_{53}R_{54}$, —$NR_{55}$(C=O)—$NR_{53}R_{54}$, —(C=S)—$NR_{53}R_{54}$, and —$NR_{55}$(C=S)—$NR_{53}R_{54}$;
- $R_8$ is selected from —$NR_{34}$—(C=O)—$R_{35}$, —$NR_{34}$—(C=S)—$R_{35}$, —$NR_{36}$—(C=O)—$NR_{34}R_{35}$, —$NR_{36}$—(C=S)—$NR_{34}R_{35}$, —$NR_{34}$—($SO_2$)—$R_{35}$, —$NR_{34}$—(C=O)—O—$R_{35}$, —$NR_{34}$—(C=S)—O—$R_{35}$, —O—(C=O)—$NR_{34}R_{35}$, and —O—(C=S)—$NR_{34}R_{35}$;
- $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{44}$, $R_{45}$, $R_{46}$, $R_{47}$, $R_{48}$, $R_{49}$, $R_{50}$, $R_{53}$, $R_{54}$ and $R_{55}$ are each independently selected from —H, -halo, =O, —OH, —$C_{1-6}$alkyl, —O—$C_{1-6}$alkyl, —S—$C_{1-6}$alkyl, —$C_{3-6}$cycloalkyl, —$Ar_5$ and -$Het_7$; wherein each of said —$C_{1-6}$alkyl is optionally and independently substituted with from 1 to 3 substituents selected from -halo, —OH, —O—$C_{1-6}$alkyl, —S—$C_{1-6}$alkyl, —$C_{3-6}$cycloalkyl, -$Het_7$, —$Ar_5$ and —$NR_{51}R_{52}$;
- $R_{51}$ and $R_{52}$ are each independently selected from —H, -halo, —OH, —$C_{1-6}$alkyl, —O—$C_{1-6}$alkyl, —S—$C_{1-6}$alkyl, —$C_{3-6}$cycloalkyl, —$Ar_{10}$ and -$Het_{10}$;
- $R_{42}$ is selected from —H, —OH, -halo, —$C_{1-6}$alkyl, —O—$C_{1-6}$alkyl, —S—$C_{1-6}$alkyl, —$NR_{46}R_{47}$, —$C_{3-6}$cycloalkyl, —$Ar_9$ and -$Het_8$;
- $R_{43}$ is selected from —H —$C_{1-6}$alkyl, and —$C_{3-6}$cycloalkyl; wherein each of said —$C_{1-6}$alkyl is optionally and independently substituted with from 1 to 3 substituents selected from -halo, —OH, —O—$C_{1-6}$alkyl, —S—$C_{1-6}$alkyl, -$Het_5$, —$C_{3-6}$cycloalkyl —$Ar_4$, and —$NR_{44}R_{45}$;
- A is selected from —$(CH_2)_n$—Y—$(CH_2)_m$—, —(C=O)—, —(C=S)—, —(C=N)—$R_{49}$—, —($SO_2$)—, —$SO_2$—$NR_5$—, —(C=O)—$NR_5$—, —(C=S)—$NR_5$—, —$NR_5$—(C=O)—$NR_7$—, —$NR_5$—(C=S)—$NR_7$—, —$NR_6$—, —$NR_5$—(C=O)—O—, —$NR_5$—(C=S)—O—, and —$CHR_8$—;
- $X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$alkyl-$NR_3$—, —$NR_3$—, —(C=O)—, —$NR_3$—

(C=O)—NR$_{48}$—, —NR$_3$—C$_{1-6}$alkyl-, —NR$_3$—SO$_2$—, —NR$_3$—(C=O)—C$_{1-6}$alkyl-, —(C=O)—NR$_3$—C$_{1-6}$alkyl-, —O—C$_{1-6}$alkyl-O—C$_{1-6}$alkyl- and —C$_{1-6}$alky-NR$_3$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl, and —NR$_{37}$R$_{38}$;

X$_2$ is selected from —C$_{1-6}$alkyl-, —O—C$_{1-6}$alkyl-, —S—C$_{1-6}$alkyl-, —(C=O)—, —NR$_2$—(C=O)—, —C$_{1-6}$alkyl-NR$_2$—, —NR$_2$—, —(C=O)—, —NR$_2$—(C=O)—NR$_{50}$—, —NR$_2$—C$_{1-6}$alkyl-, —NR$_2$—SO$_2$—, —NR$_2$—(C=O)—C$_{1-6}$alkyl-, —(C=O)—NR$_2$—C$_{1-6}$alkyl-, —O—C$_{1-6}$alkyl-O—C$_{1-6}$alkyl- and —C$_{1-6}$alkyl-NR$_2$—C$_{1-6}$alkyl-; wherein each of said —C$_{1-6}$alkyl- is optionally and independently substituted with from 1 to 3 substituents selected from -halo, —OH, —C$_{1-6}$alkyl, —O—C$_{1-6}$alkyl, —S—C$_{1-6}$alkyl, -phenyl and —NR$_{39}$R$_{40}$;

Y is selected from a direct bond, —CHR$_{42}$—, —O—, —S—, and —NR$_{43}$—;

Ar$_1$, Ar$_2$, Ar$_3$, Ar$_4$, Ar$_5$, Ar$_6$, Ar$_7$, Ar$_8$, Ar$_9$, Ar$_{10}$ and Ar$_{11}$ are each independently a 5- to 10-membered aromatic heterocycle optionally comprising 1 or 2 heteroatoms selected from O, N and S; each of said Ar$_1$, Ar$_2$, Ar$_3$, Ar$_4$, Ar$_5$, Ar$_6$, Ar$_7$, Ar$_8$, Ar$_9$, and Ar$_{10}$ being optionally and independently substituted with from 1 to 3 substituents selected from -halo, —OH, —C$_{1-6}$alkyl, —O—C$_{1-6}$alkyl, —S—C$_{1-6}$alkyl, and —NR$_{19}$R$_{20}$; wherein each of said —C$_{1-6}$alkyl is optionally and independently substituted with from 1 to 3 -halo;

Het$_1$, Het$_2$, Het$_3$, Het$_4$, Het$_5$, Het$_6$, Het$_7$, Het$_8$, Het$_9$, Het$_{10}$, and Het$_{12}$ are each independently a 4- to 10-membered heterocycle having from 1 to 3 heteroatoms selected from O, N and S, wherein each of said Het$_1$, Het$_2$, Het$_3$, Het$_4$, Het$_5$, Het$_6$, Het$_7$, Het$_8$, Het$_9$, Het$_{10}$, and Het$_{12}$ is optionally and independently substituted with from 1 to 3 substituents selected from -halo, —OH, —C$_{1-6}$alkyl, —OC$_{1-6}$alkyl, —SC$_{1-6}$alkyl, =O, —(C=O)—C$_{1-6}$alkyl, and —NR$_{21}$R$_{22}$; wherein each of said —C$_{1-6}$alkyl is optionally and independently substituted with from 1 to 3 -halo;

Z$_1$, Z$_2$, Z$_3$, Z$_4$ and Z$_5$ are each independently selected from C and N; and m and n are each independently 1, 2, 3, or 4.

* * * * *